US008486990B2

(12) United States Patent
Napper et al.

(10) Patent No.: US 8,486,990 B2
(45) Date of Patent: Jul. 16, 2013

(54) SIRT INHIBITORS THAT BIND TO NAD

(75) Inventors: Andrew Napper, Salem, MA (US); Peter DiStefano, Southboro, MA (US); Rory A. Curtis, Ashland, MA (US); Jeffrey Hixon, Salisbury, MA (US); Thomas McDonagh, Acton, MA (US); L. Julie Huber, Newton, MA (US); Jonathan M. Solomon, Somerville, MA (US); Russell J. Thomas, Siena (IT); Jean-Francois Pons, Oxford (GB)

(73) Assignee: Elixir Pharmaceuticals, Inc., Cambridge, MA (US)

( * ) Notice: Subject to any disclaimer, the term of this patent is extended or adjusted under 35 U.S.C. 154(b) by 68 days.

(21) Appl. No.: 12/423,751

(22) Filed: Apr. 14, 2009

(65) Prior Publication Data

US 2009/0306168 A1    Dec. 10, 2009

Related U.S. Application Data

(60) Division of application No. 11/077,664, filed on Mar. 11, 2005, now abandoned, which is a continuation-in-part of application No. 10/940,269, filed on Sep. 13, 2004, now abandoned.

(60) Provisional application No. 60/560,509, filed on Apr. 7, 2004, provisional application No. 60/502,811, filed on Sep. 12, 2003, provisional application No. 60/531,443, filed on Dec. 19, 2003.

(51) Int. Cl.
*A61K 31/403* (2006.01)
*C07D 209/56* (2006.01)

(52) U.S. Cl.
USPC .......................................... 514/411; 548/448

(58) Field of Classification Search
USPC ............................................ 514/411; 548/448
See application file for complete search history.

(56) References Cited

U.S. PATENT DOCUMENTS

| 3,769,298 | A | 10/1973 | McManus et al. |
|---|---|---|---|
| 3,859,304 | A | 1/1975 | Dostert et al. |
| 4,009,181 | A | 2/1977 | Berger et al. |
| 4,057,640 | A | 11/1977 | Biere et al. |
| 5,830,911 | A | 11/1998 | Failli et al. |
| 2001/0039012 | A1 | 11/2001 | Lapidus |
| 2003/0124101 | A1 | 7/2003 | Gu |

FOREIGN PATENT DOCUMENTS

| DE | 24 31 292 A1 | 1/1976 |
|---|---|---|
| GB | 1436893 | 5/1976 |
| WO | 9603377 A1 | 2/1996 |
| WO | 9737658 | 10/1997 |
| WO | 0002878 | 1/2000 |
| WO | 03/051837 | 6/2003 |
| WO | 03/062392 | 7/2003 |
| WO | 2004055169 A2 | 7/2004 |
| WO | 2005009370 | 2/2005 |
| WO | 2005026112 | 2/2005 |
| WO | 2005026112 A2 | 3/2005 |
| WO | 2005060711 A2 | 7/2005 |
| WO | 2005072408 A2 | 8/2005 |
| WO | 2006031894 A2 | 3/2006 |

OTHER PUBLICATIONS

Tang et al. "SIRT1 and neuronal diseases" Molecular Aspects of Medicine, 2008, pp. 187-200.*
Pallas et al. "Modulation of SIRT1 expression in different neurodegenerative models and human pathologies" Neuroscience, 2008, pp. 1388-1397.*
Mai et al., Design Synthesis, and Biological Evaluation of Sirtinol Alanlogues as Class III Histone/Protein Deacetylase (Sirtuin) Inhibitors, J. Med. Chem. 2005, 7789-7795.
Andrew Napper D. et al. "Discovery of Indoles As Potent and Selective Inhibitors of the Deacetylase SIRTI," Journal of Medicinal Chemistry, American Chemical Society, Washington, US, vol. 48 No. 25, Dec. 15, 2005, pp. 8045-8054, XP002414402, D ISSN: 0022-2623.
Davies Shelly L et al: "Targeting SIRTI-A Multitasker," Drugs of the Future, Barcelona, ES vol. 31, No. 5, May 2006, pp. 461-465, XP002459855, ISSN: 0377-8282.
Grozinger Christina M et al:" Identification of a Class of Small Molecule Inhibitors of the Sirtuin Family of NAD-Dependent Deacetylases by Phenotypic Screening," Journal of Biological Chemistry, vol. 276 No. 42, Oct. 19, 2001, pp. 3887-38843, XP002463628 abstract* p. D 38839; figure c compound A3*.
Supplemental European Search Report for European Application No. EP 05 80 3803.
Examination Report from corresponding European Application No. EP05803803.5.
Beher et al., "Resveratrol is Not a Direct Activator of SIRT1 Enzyme Activity", Chem Biol Drug Des 2009; 74:619-624.
Parshin, V.A., et al., "Synthesis and Pharmacological Activity of 1,2,3,4 Tetrahydrocarbazole 1-Carboxiami Des" Voprosy Biologichekoi, Meditsinskoi, I Farmatsevticheskoikhimii—Problems of Biological Medical and Pharmacological, Izdatel' Stvo Meditsina, Moscow, RU, No. 4, Jan. 1, 2001, pp. 40-45.
Howitz Konrad T. et al., "Small Molecule Activators of Sirtuins Extend *Saccharomyces cerevisiae* Lifespan", Nature, vol. 425(6954), Sep. 1, 2003, pp. 191-196.
Supplementary European Search Report for related application EP 04 78 8727, dated Apr. 12, 2010.
Bodai, L., "Altered Protein Acetylation in Polyglutamine Diseases", Current Medicinal Chemistry, 2003, 10, 2577-2587.

*Primary Examiner* — Joseph Kosack
(74) *Attorney, Agent, or Firm* — Lando & Anastasi LLP

(57) ABSTRACT

Compound of formula (I)

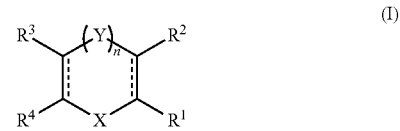

and methods of treating disorders by administering a compound of formula (I) are described herein. Examples of disorders include neoplastic disorders, fat-cell related disorders, neurodegenerative disorders, and metabolic disorders.

5 Claims, 15 Drawing Sheets

OTHER PUBLICATIONS

Green, K.N., "Nicotinamide Restores Cognition in Alzheimer's Disease Transgenic Mice via a Mechanism Involving Sirtuin Inhibition and Selective Reduction of Thr231-Phosphotau", The Journal of Neuroscience, 2008, 28(45), 11500-11510.

International Search Report from International Application No. PCT/US2004/29942 dated Oct. 3, 2005.

International Search Report from International Application No. PCT/US2005/32760 dated Sep. 15, 2006.

Jeong, H., "Acetylation Targets Mutant Huntingtin to Autophagosomes for Degradation", Cell, 2009, 137, 60-72.

Mangiarini, L, "Exon 1 of the HD Gene with an Expanded CAG Repeat Is Sufficient to Cause a Progressive Neurological Phenotype in Transgenic Mice", Cell, 1996, 87, 493-506.

Orlando, L.R., "Sirtuins as Targets for HD Treatment", Workshop, Jan. 27-28, 2007, Cambridge, Massachusetts.

Pacholec, M., "SRT1720, SRT2183, SRT1460, and Resveratrol Are Not Direct Activators of SIRT1", The Journal of Biological Chemistry, 2010, 285(11), 8340-8351.

Pallos, J., "Inhibition of specific HDACs and sirtuins suppresses pathogenesis in a *Drosophila* model of Huntington's disease", Human Molecular Genetics, 2008, 17(23), 3767-3775.

* cited by examiner

|  |  |  |  |  |  | Selectivity | |
|---|---|---|---|---|---|---|---|
| Compound Number | SirT1 | SirT2 | SirT3 | HDAC | NaDase | SirT2/ SirT1 | SirT3/ SirT1 |
| 8 | 0.038 | 3.96 | 27.6 | >50 | >50 | 104 | 726 |
| 4 | 0.357 | 5.99 | >50 | >50 | >50 | 17 | >140 |
| 5 | 0.639 | 14.44 | >50 | >50 | >50 | 23 | >78 |
| 15 | >50 | >50 |  |  |  |  |  |
| 16 | >50 | >50 |  |  |  |  |  |

FIG. 1

1-21-04 Acetylation of p53 in response to active and inactive SIRT1 inhinbitors

NCI-H460 cells were treated for 6 hours with 20μM etoposide, 25 nM TSA, and 1μM of SIRT1 inhibitor compounds. Acetylated p53 was visualized by Western blot.

SEQUENCE LISTING

```
<160> NUMBER OF SEQ ID NOS: 7

<210> SEQ ID NO 1
<211> LENGTH: 747
<212> TYPE: PRT
<213> ORGANISM: Homo sapiens

<400> SEQUENCE: 1

Met Ala Asp Glu Ala Ala Leu Ala Leu Gln Pro Gly Gly Ser Pro Ser
1               5                   10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Leu Trp Arg Glu Ala Glu
65                  70                  75                  80

Ala Glu Ala Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110
```

```
Glu Pro Pro Leu Ala Asp Asn Leu Tyr Asp Glu Asp Asp Asp Glu
            115                 120                 125

Gly Glu Glu Glu Glu Ala Ala Ala Ala Ile Gly Tyr Arg Asp
        130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
                180                 185                 190

Met Ile Gly Thr Asp Pro Arg Thr Ile Leu Lys Asp Leu Leu Pro Glu
            195                 200                 205

Thr Ile Pro Pro Pro Glu Leu Asp Asp Met Thr Leu Trp Gln Ile Val
        210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
                260                 265                 270

Phe Arg Ser Arg Asp Gly Ile Tyr Ala Arg Leu Ala Val Asp Phe Pro
            275                 280                 285

Asp Leu Pro Asp Pro Gln Ala Met Phe Asp Ile Glu Tyr Phe Arg Lys
        290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
                340                 345                 350

Val Ala Gly Ile Gln Arg Ile Ile Gln Cys His Gly Ser Phe Ala Thr
            355                 360                 365

Ala Ser Cys Leu Ile Cys Lys Tyr Lys Val Asp Cys Glu Ala Val Arg
        370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
                405                 410                 415

Asn Leu Pro Glu Gln Phe His Arg Ala Met Lys Tyr Asp Lys Asp Glu
                420                 425                 430

Val Asp Leu Leu Ile Val Ile Gly Ser Ser Leu Lys Val Arg Pro Val
            435                 440                 445

Ala Leu Ile Pro Ser Ser Ile Pro His Glu Val Pro Gln Ile Leu Ile
        450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Ser Pro Glu Arg Thr
```

```
                   530                 535                 540
Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
                595                 600                 605

Glu Lys Asn Glu Arg Thr Ser Val Ala Gly Thr Val Arg Lys Cys Trp
            610                 615                 620

Pro Asn Arg Val Ala Lys Glu Gln Ile Ser Arg Arg Leu Asp Gly Asn
625                 630                 635                 640

Gln Tyr Leu Phe Leu Pro Asn Arg Tyr Ile Phe His Gly Ala Glu
                    645                 650                 655

Val Tyr Ser Asp Ser Glu Asp Val Leu Ser Ser Ser Cys Gly
                660                 665                 670

Ser Asn Ser Asp Ser Gly Thr Cys Gln Ser Pro Ser Leu Glu Glu Pro
            675                 680                 685

Met Glu Asp Glu Ser Glu Ile Glu Glu Phe Tyr Asn Gly Leu Glu Asp
            690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                    725                 730                 735

Val Thr Asp Met Asn Tyr Pro Ser Asn Lys Ser
                740                 745

<210> SEQ ID NO 2
<211> LENGTH: 389
<212> TYPE: PRT
<213> ORGANISM: Homo sapiens

<400> SEQUENCE: 2

Met Ala Glu Pro Asp Pro Ser His Pro Leu Glu Thr Gln Ala Gly Lys
1               5                   10                  15

Val Gln Glu Ala Gln Asp Ser Asp Ser Asp Ser Glu Gly Gly Ala Ala
            20                  25                  30

Gly Gly Glu Ala Asp Met Asp Phe Leu Arg Asn Leu Phe Ser Gln Thr
        35                  40                  45

Leu Ser Leu Gly Ser Gln Lys Glu Arg Leu Leu Asp Glu Leu Thr Leu
50                  55                  60

Glu Gly Val Ala Arg Tyr Met Gln Ser Glu Arg Cys Arg Arg Val Ile
65                  70                  75                  80

Cys Leu Val Gly Ala Gly Ile Ser Thr Ser Ala Gly Ile Pro Asp Phe
                85                  90                  95

Arg Ser Pro Ser Thr Gly Leu Tyr Asp Asn Leu Glu Lys Tyr His Leu
            100                 105                 110

Pro Tyr Pro Glu Ala Ile Phe Glu Ile Ser Tyr Phe Lys Lys His Pro
        115                 120                 125

Glu Pro Phe Phe Ala Leu Ala Lys Glu Leu Tyr Pro Gly Gln Phe Lys
    130                 135                 140

Pro Thr Ile Cys His Tyr Phe Met Arg Leu Leu Lys Asp Lys Gly Leu
145                 150                 155                 160

Leu Leu Arg Cys Tyr Thr Gln Asn Ile Asp Thr Leu Glu Arg Ile Ala
```

-continued

```
                165                 170                 175
Gly Leu Glu Gln Glu Asp Leu Val Glu Ala His Gly Thr Phe Tyr Thr
            180                 185                 190

Ser His Cys Val Ser Ala Ser Cys Arg His Glu Tyr Pro Leu Ser Trp
        195                 200                 205

Met Lys Glu Lys Ile Phe Ser Glu Val Thr Pro Lys Cys Glu Asp Cys
    210                 215                 220

Gln Ser Leu Val Lys Pro Asp Ile Val Phe Phe Gly Glu Ser Leu Pro
225                 230                 235                 240

Ala Arg Phe Phe Ser Cys Met Gln Ser Asp Phe Leu Lys Val Asp Leu
                245                 250                 255

Leu Leu Val Met Gly Thr Ser Leu Gln Val Gln Pro Phe Ala Ser Leu
            260                 265                 270

Ile Ser Lys Ala Pro Leu Ser Thr Pro Arg Leu Leu Ile Asn Lys Glu
        275                 280                 285

Lys Ala Gly Gln Ser Asp Pro Phe Leu Gly Met Ile Met Gly Leu Gly
    290                 295                 300

Gly Gly Met Asp Phe Asp Ser Lys Lys Ala Tyr Arg Asp Val Ala Trp
305                 310                 315                 320

Leu Gly Glu Cys Asp Gln Gly Cys Leu Ala Leu Ala Glu Leu Leu Gly
                325                 330                 335

Trp Lys Lys Glu Leu Glu Asp Leu Val Arg Arg Glu His Ala Ser Ile
            340                 345                 350

Asp Ala Gln Ser Gly Ala Gly Val Pro Asn Pro Ser Thr Ser Ala Ser
        355                 360                 365

Pro Lys Lys Ser Pro Pro Pro Ala Lys Asp Glu Ala Arg Thr Thr Glu
    370                 375                 380

Arg Glu Lys Pro Gln
385
```

<210> SEQ ID NO 3
<211> LENGTH: 399
<212> TYPE: PRT
<213> ORGANISM: Homo sapiens

<400> SEQUENCE: 3

```
Met Ala Phe Trp Gly Trp Arg Ala Ala Ala Leu Arg Leu Trp Gly
  1               5                  10                  15

Arg Val Val Glu Arg Val Glu Ala Gly Gly Val Gly Pro Phe Gln
             20                  25                  30

Ala Cys Gly Cys Arg Leu Val Leu Gly Gly Arg Asp Asp Val Ser Ala
             35                  40                  45

Gly Leu Arg Gly Ser His Gly Ala Arg Gly Glu Pro Leu Asp Pro Ala
         50                  55                  60

Arg Pro Leu Gln Arg Pro Pro Arg Pro Glu Val Pro Arg Ala Phe Arg
 65                  70                  75                  80

Arg Gln Pro Arg Ala Ala Ala Pro Ser Phe Phe Phe Ser Ser Ile Lys
                 85                  90                  95

Gly Gly Arg Arg Ser Ile Ser Phe Ser Val Gly Ala Ser Ser Val Val
            100                 105                 110

Gly Ser Gly Gly Ser Ser Asp Lys Gly Lys Leu Ser Leu Gln Asp Val
        115                 120                 125

Ala Glu Leu Ile Arg Ala Arg Ala Cys Gln Arg Val Val Val Met Val
    130                 135                 140

Gly Ala Gly Ile Ser Thr Pro Ser Gly Ile Pro Asp Phe Arg Ser Pro
```

```
                145                 150                 155                 160
Gly Ser Gly Leu Tyr Ser Asn Leu Gln Gln Tyr Asp Leu Pro Tyr Pro
                165                 170                 175

Glu Ala Ile Phe Glu Leu Pro Phe Phe His Asn Pro Lys Pro Phe
        180                 185                 190

Phe Thr Leu Ala Lys Glu Leu Tyr Pro Gly Asn Tyr Lys Pro Asn Val
        195                 200                 205

Thr His Tyr Phe Leu Arg Leu His Asp Lys Gly Leu Leu Leu Arg
210                 215                 220

Leu Tyr Thr Gln Asn Ile Asp Gly Leu Glu Arg Val Ser Gly Ile Pro
225                 230                 235                 240

Ala Ser Lys Leu Val Glu Ala His Gly Thr Phe Ala Ser Ala Thr Cys
                245                 250                 255

Thr Val Cys Gln Arg Pro Phe Pro Gly Glu Asp Ile Arg Ala Asp Val
                260                 265                 270

Met Ala Asp Arg Val Pro Arg Cys Pro Val Cys Thr Gly Val Val Lys
        275                 280                 285

Pro Asp Ile Val Phe Phe Gly Glu Pro Leu Pro Gln Arg Phe Leu Leu
290                 295                 300

His Val Val Asp Phe Pro Met Ala Asp Leu Leu Leu Ile Leu Gly Thr
305                 310                 315                 320

Ser Leu Glu Val Glu Pro Phe Ala Ser Leu Thr Glu Ala Val Arg Ser
                325                 330                 335

Ser Val Pro Arg Leu Leu Ile Asn Arg Asp Leu Val Gly Pro Leu Ala
                340                 345                 350

Trp His Pro Arg Ser Arg Asp Val Ala Gln Leu Gly Asp Val Val His
                355                 360                 365

Gly Val Glu Ser Leu Val Glu Leu Leu Gly Trp Thr Glu Glu Met Arg
370                 375                 380

Asp Leu Val Gln Arg Glu Thr Gly Lys Leu Asp Gly Pro Asp Lys
385                 390                 395

<210> SEQ ID NO 4
<211> LENGTH: 314
<212> TYPE: PRT
<213> ORGANISM: Homo sapiens

<400> SEQUENCE: 4

Met Lys Met Ser Phe Ala Leu Thr Phe Arg Ser Ala Lys Gly Arg Trp
1               5                   10                  15

Ile Ala Asn Pro Ser Gln Pro Cys Ser Lys Ala Ser Ile Gly Leu Phe
                20                  25                  30

Val Pro Ala Ser Pro Pro Leu Asp Pro Glu Lys Val Lys Glu Leu Gln
        35                  40                  45

Arg Phe Ile Thr Leu Ser Lys Arg Leu Leu Val Met Thr Gly Ala Gly
50                  55                  60

Ile Ser Thr Glu Ser Gly Ile Pro Asp Tyr Arg Ser Glu Lys Val Gly
65                  70                  75                  80

Leu Tyr Ala Arg Thr Asp Arg Arg Pro Ile Gln His Gly Asp Phe Val
                85                  90                  95

Arg Ser Ala Pro Ile Arg Gln Arg Tyr Trp Ala Arg Asn Phe Val Gly
            100                 105                 110

Trp Pro Gln Phe Ser Ser His Gln Pro Asn Pro Ala His Trp Ala Leu
        115                 120                 125

Ser Thr Trp Glu Lys Leu Gly Lys Leu Tyr Trp Leu Val Thr Gln Asn
```

```
                130                 135                 140
Val Asp Ala Leu His Thr Lys Ala Gly Ser Arg Arg Leu Thr Glu Leu
145                 150                 155                 160

His Gly Cys Met Asp Arg Val Leu Cys Leu Asp Cys Gly Glu Gln Thr
                165                 170                 175

Pro Arg Gly Val Leu Gln Glu Arg Phe Gln Val Leu Asn Pro Thr Trp
            180                 185                 190

Ser Ala Glu Ala His Gly Leu Ala Pro Asp Gly Asp Val Phe Leu Ser
        195                 200                 205

Glu Glu Gln Val Arg Ser Phe Gln Val Pro Thr Cys Val Gln Cys Gly
210                 215                 220

Gly His Leu Lys Pro Asp Val Val Phe Phe Gly Asp Thr Val Asn Pro
225                 230                 235                 240

Asp Lys Val Asp Phe Val His Lys Arg Val Lys Glu Ala Asp Ser Leu
                245                 250                 255

Leu Val Val Gly Ser Ser Leu Gln Val Tyr Ser Gly Tyr Arg Phe Ile
                260                 265                 270

Leu Thr Ala Trp Glu Lys Lys Leu Pro Ile Ala Ile Leu Asn Ile Gly
            275                 280                 285

Pro Thr Arg Ser Asp Asp Leu Ala Cys Leu Lys Leu Asn Ser Arg Cys
        290                 295                 300

Gly Glu Leu Leu Pro Leu Ile Asp Pro Cys
305                 310

<210> SEQ ID NO 5
<211> LENGTH: 310
<212> TYPE: PRT
<213> ORGANISM: Homo sapiens

<400> SEQUENCE: 5

Met Arg Pro Leu Gln Ile Val Pro Ser Arg Leu Ile Ser Gln Leu Tyr
1               5                   10                  15

Cys Gly Leu Lys Pro Pro Ala Ser Thr Arg Asn Gln Ile Cys Leu Lys
            20                  25                  30

Met Ala Arg Pro Ser Ser Ser Met Ala Asp Phe Arg Lys Phe Phe Ala
        35                  40                  45

Lys Ala Lys His Ile Val Ile Ser Gly Ala Gly Val Ser Ala Glu
    50                  55                  60

Ser Gly Val Pro Thr Phe Arg Gly Ala Gly Gly Tyr Trp Arg Lys Trp
65                  70                  75                  80

Gln Ala Gln Asp Leu Ala Thr Pro Leu Ala Phe Ala His Asn Pro Ser
                85                  90                  95

Arg Val Trp Glu Phe Tyr His Tyr Arg Arg Glu Val Met Gly Ser Lys
            100                 105                 110

Glu Pro Asn Ala Gly His Arg Ala Ile Ala Glu Cys Glu Thr Arg Leu
        115                 120                 125

Gly Lys Gln Gly Arg Arg Val Val Val Ile Thr Gln Asn Ile Asp Glu
    130                 135                 140

Leu His Arg Lys Ala Gly Thr Lys Asn Leu Leu Glu Ile His Gly Ser
145                 150                 155                 160

Leu Phe Lys Thr Arg Cys Thr Ser Cys Gly Val Val Ala Glu Asn Tyr
                165                 170                 175

Lys Ser Pro Ile Cys Pro Ala Leu Ser Gly Lys Gly Ala Pro Glu Pro
            180                 185                 190

Gly Thr Gln Asp Ala Ser Ile Pro Val Glu Lys Leu Pro Arg Cys Glu
```

```
                195                 200                 205
Glu Ala Gly Cys Gly Gly Leu Leu Arg Pro His Val Val Trp Phe Gly
210                 215                 220

Glu Asn Leu Asp Pro Ala Ile Leu Glu Glu Val Asp Arg Glu Leu Ala
225                 230                 235                 240

His Cys Asp Leu Cys Leu Val Val Gly Thr Ser Ser Val Val Tyr Pro
                245                 250                 255

Ala Ala Met Phe Ala Pro Gln Val Ala Arg Gly Val Pro Val Ala
                260                 265                 270

Glu Phe Asn Thr Glu Thr Thr Pro Ala Thr Asn Arg Phe Arg Phe His
                275                 280                 285

Phe Gln Gly Pro Cys Gly Thr Thr Leu Pro Glu Ala Leu Ala Cys His
                290                 295                 300

Glu Asn Glu Thr Val Ser
305                 310

<210> SEQ ID NO 6
<211> LENGTH: 355
<212> TYPE: PRT
<213> ORGANISM: Homo sapiens

<400> SEQUENCE: 6

Met Ser Val Asn Tyr Ala Ala Gly Leu Ser Pro Tyr Ala Asp Lys Gly
 1               5                  10                  15

Lys Cys Gly Leu Pro Glu Ile Phe Asp Pro Pro Glu Glu Leu Glu Arg
                20                  25                  30

Lys Val Trp Glu Leu Ala Arg Leu Val Trp Gln Ser Ser Ser Val Val
            35                  40                  45

Phe His Thr Gly Ala Gly Ile Ser Thr Ala Ser Gly Ile Pro Asp Phe
        50                  55                  60

Arg Gly Pro His Gly Val Trp Thr Met Glu Glu Arg Gly Leu Ala Pro
65                  70                  75                  80

Lys Phe Asp Thr Thr Phe Glu Ser Ala Arg Pro Thr Gln Thr His Met
                85                  90                  95

Ala Leu Val Gln Leu Glu Arg Val Gly Leu Leu Arg Phe Leu Val Ser
                100                 105                 110

Gln Asn Val Asp Gly Leu His Val Arg Ser Gly Phe Pro Arg Asp Lys
            115                 120                 125

Leu Ala Glu Leu His Gly Asn Met Phe Val Glu Glu Cys Ala Lys Cys
        130                 135                 140

Lys Thr Gln Tyr Val Arg Asp Thr Val Val Gly Thr Met Gly Leu Lys
145                 150                 155                 160

Ala Thr Gly Arg Leu Cys Thr Val Ala Lys Ala Arg Gly Leu Arg Ala
                165                 170                 175

Cys Arg Gly Glu Leu Arg Asp Thr Ile Leu Asp Trp Glu Asp Ser Leu
                180                 185                 190

Pro Asp Arg Asp Leu Ala Leu Ala Asp Glu Ala Ser Arg Asn Ala Asp
            195                 200                 205

Leu Ser Ile Thr Leu Gly Thr Ser Leu Gln Ile Arg Pro Ser Gly Asn
        210                 215                 220

Leu Pro Leu Ala Thr Lys Arg Arg Gly Gly Arg Leu Val Ile Val Asn
225                 230                 235                 240

Leu Gln Pro Thr Lys His Asp Arg His Ala Asp Leu Arg Ile His Gly
                245                 250                 255

Tyr Val Asp Glu Val Met Thr Arg Leu Met Lys His Leu Gly Leu Glu
```

-continued

```
                    260                 265                 270
Ile Pro Ala Trp Asp Gly Pro Arg Val Leu Glu Arg Ala Leu Pro Pro
            275                 280                 285

Leu Pro Arg Pro Pro Thr Pro Lys Leu Glu Pro Lys Glu Glu Ser Pro
        290                 295                 300

Thr Arg Ile Asn Gly Ser Ile Pro Ala Gly Pro Lys Gln Glu Pro Cys
305                 310                 315                 320

Ala Gln His Asn Gly Ser Glu Pro Ala Ser Pro Lys Arg Glu Arg Pro
                325                 330                 335

Thr Ser Pro Ala Pro His Arg Pro Pro Lys Arg Val Lys Ala Lys Ala
            340                 345                 350

Val Pro Ser
        355

<210> SEQ ID NO 7
<211> LENGTH: 400
<212> TYPE: PRT
<213> ORGANISM: Homo sapiens

<400> SEQUENCE: 7

Met Ala Ala Gly Gly Leu Ser Arg Ser Glu Arg Lys Ala Glu Arg
  1               5                  10                  15

Val Arg Arg Leu Arg Glu Glu Gln Arg Glu Arg Leu Arg Gln Val
                20                  25                  30

Ser Arg Ile Leu Arg Lys Ala Ala Glu Arg Ser Ala Glu Glu Gly
            35                  40                  45

Arg Leu Leu Ala Glu Ser Ala Asp Leu Val Thr Glu Leu Gln Gly Arg
 50                  55                  60

Ser Arg Arg Arg Glu Gly Leu Lys Arg Gln Glu Glu Val Cys Asp
65                  70                  75                  80

Asp Pro Glu Glu Leu Arg Gly Lys Val Arg Glu Leu Ala Ser Ala Val
                85                  90                  95

Arg Asn Ala Lys Tyr Leu Val Val Tyr Thr Gly Ala Gly Ile Ser Thr
            100                 105                 110

Ala Ala Ser Ile Pro Asp Tyr Arg Gly Pro Asn Gly Val Trp Thr Leu
        115                 120                 125

Leu Gln Lys Gly Arg Ser Val Ser Ala Ala Asp Leu Ser Glu Ala Glu
130                 135                 140

Pro Thr Leu Thr His Met Ser Ile Thr Arg Leu His Glu Gln Lys Leu
145                 150                 155                 160

Val Gln His Val Val Ser Gln Asn Cys Asp Gly Leu His Leu Arg Ser
                165                 170                 175

Gly Leu Pro Arg Thr Ala Ile Ser Glu Leu His Gly Asn Met Tyr Ile
            180                 185                 190

Glu Val Cys Thr Ser Cys Val Pro Asn Arg Glu Tyr Val Arg Val Phe
        195                 200                 205

Asp Val Thr Glu Arg Thr Ala Leu His Arg His Gln Thr Gly Arg Thr
    210                 215                 220

Cys His Lys Cys Gly Thr Gln Leu Arg Asp Thr Ile Val His Phe Gly
225                 230                 235                 240

Glu Arg Gly Thr Leu Gly Gln Pro Leu Asn Trp Glu Ala Ala Thr Glu
                245                 250                 255

Ala Ala Ser Arg Ala Asp Thr Ile Leu Cys Leu Gly Ser Ser Leu Lys
            260                 265                 270

Val Leu Lys Lys Tyr Pro Arg Leu Trp Cys Met Thr Lys Pro Pro Ser
```

-continued

|  |  |  | 275 |  |  |  | 280 |  |  |  | 285 |  |  |  |
|---|---|---|---|---|---|---|---|---|---|---|---|---|---|---|
| Arg | Arg | Pro | Lys | Leu | Tyr | Ile | Val | Asn | Leu | Gln | Trp | Thr | Pro | Lys | Asp |
|  | 290 |  |  |  | 295 |  |  |  |  | 300 |  |  |  |  |
| Asp | Trp | Ala | Ala | Leu | Lys | Leu | His | Gly | Lys | Cys | Asp | Asp | Val | Met | Arg |
| 305 |  |  |  | 310 |  |  |  |  | 315 |  |  |  |  | 320 |
| Leu | Leu | Met | Ala | Glu | Leu | Gly | Leu | Glu | Ile | Pro | Ala | Tyr | Ser | Arg | Trp |
|  |  |  | 325 |  |  |  | 330 |  |  |  |  | 335 |  |  |
| Gln | Asp | Pro | Ile | Phe | Ser | Leu | Ala | Thr | Pro | Leu | Arg | Ala | Gly | Glu | Glu |
|  |  | 340 |  |  |  | 345 |  |  |  |  | 350 |  |  |  |
| Gly | Ser | His | Ser | Arg | Lys | Ser | Leu | Cys | Arg | Ser | Arg | Glu | Glu | Ala | Pro |
|  | 355 |  |  |  | 360 |  |  |  |  | 365 |  |  |  |  |
| Pro | Gly | Asp | Arg | Gly | Ala | Pro | Leu | Ser | Ser | Ala | Pro | Ile | Leu | Gly | Gly |
|  | 370 |  |  |  | 375 |  |  |  |  | 380 |  |  |  |  |
| Trp | Phe | Gly | Arg | Gly | Cys | Thr | Lys | Arg | Thr | Lys | Arg | Lys | Lys | Val | Thr |
| 385 |  |  |  | 390 |  |  |  |  | 395 |  |  |  |  | 400 |

SIRT INHIBITORS THAT BIND TO NAD

CLAIM OF PRIORITY

This application is a divisional of U.S. Ser. No. 11/077,664 filed on Mar. 11, 2005 now abandoned, which claims priority under 35 USC §119(e) to U.S. Patent Application Ser. No. 60/502,811, filed on Sep. 12, 2003, U.S. Patent Application Ser. No. 60/531,443, filed on Dec. 19, 2003, and U.S. Patent Application Ser. No. 60/560,509, filed on Apr. 7, 2004, and is a continuation-in-part of U.S. patent application Ser. No. 10/940,269, filed Sep. 13, 2004 now abandoned, the entire contents of each of which are hereby incorporated by reference.

BACKGROUND

The Sir2 protein is a deacetylase which uses NAD as a cofactor (Imai et al., 2000; Moazed, 2001; Smith et al., 2000; Tanner et al., 2000; Tanny and Moazed, 2001). Unlike other deacetylases, many of which are involved in gene silencing, Sir2 is insensitive to histone deacetylase inhibitors like trichostatin A (TSA) (Imai et al., 2000; Landry et al., 2000a; Smith et al., 2000).

SUMMARY

The invention relates to substituted heterocyclic compounds, compositions comprising the compounds, and methods of using the compounds and compound compositions. The compounds and compositions comprising them are useful for treating disease or disease symptoms, including those mediated by sirtuin, e.g., SIRT1, mediated deacetylation.

In one aspect, this invention relates to a method for treating or preventing a disorder in a subject, e.g., a disorder described herein. The method includes administering to the subject an effective amount of a compound having a formula (I):

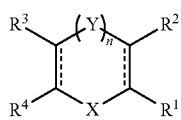

wherein, $R^1$ and $R^2$, together with the carbons to which they are attached, form $C_5$-$C_{10}$cycloalkyl, $C_5$-$C_{10}$heterocyclyl, $C_5$-$C_{10}$cycloalkenyl, $C_5$-$C_{10}$heterocycloalkenyl, $C_6$-$C_{10}$aryl, or $C_5$-$C_{10}$heteroaryl, each of which may be optionally substituted with 1-5 $R^5$; or $R^1$ is H, S-alkyl, or S-aryl, and $R^2$ is amidoalkyl wherein the nitrogen is substituted with alkyl, aryl, or arylalkyl, each of which is optionally further substituted with alkyl, halo, hydroxy, or alkoxy;

$R^3$ and $R^4$, together with the carbons to which they are attached, form $C_5$-$C_{10}$cycloalkyl, $C_5$-$C_{10}$heterocyclyl, $C_5$-$C_{10}$cycloalkenyl, $C_5$-$C_{10}$heterocycloalkenyl, $C_6$-$C_{10}$aryl, or $C_5$-$C_{10}$heteroaryl, each of which may be optionally substituted with 1-5 $R^6$;

each of $R^5$ and $R^6$ is, independently, halo, hydroxy, $C_1$-$C_{10}$alkyl, $C_1$-$C_6$haloalkyl, $C_1$-$C_{10}$alkoxy, $C_1$-$C_6$haloalkoxy, $C_6$-$C_{10}$aryl, $C_5$-$C_{10}$heteroaryl, $C_7$-$C_{12}$aralkyl, $C_7$-$C_{12}$heteroaralkyl, $C_3$-$C_8$heterocyclyl, $C_2$-$C_{12}$alkenyl, $C_2$-$C_{12}$alkynyl, $C_5$-$C_{10}$cycloalkenyl, $C_5$-$C_{10}$heterocycloalkenyl, carboxy, carboxylate, cyano, nitro, amino, $C_1$-$C_6$alkyl amino, $C_1$-$C_6$ dialkyl amino, mercapto, $SO_3H$, sulfate, $S(O)NH_2$, $S(O)_2NH_2$, phosphate, $C_1$-$C_4$alkylenedioxy, oxo, acyl, aminocarbonyl, $C_1$-$C_6$alkyl aminocarbonyl, $C_1$-$C_6$ dialkyl aminocarbonyl, $C_1$-$C_{10}$alkoxycarbonyl, $C_1$-$C_{10}$thioalkoxycarbonyl, hydrazinocarbonyl, $C_1$-$C_6$alkyl hydrazinocarbonyl, $C_1$-$C_6$ dialkyl hydrazinocarbonyl, hydroxyaminocarbonyl; alkoxyaminocarbonyl; or one of $R^5$ or $R^6$ and $R^7$ form a cyclic moiety containing 4-6 carbons, 1-3 nitrogens, 0-2 oxygens and 0-2 sulfurs, which may be optionally substituted with oxo or $C_1$-$C_6$alkyl;

X is $NR^7$, O or S; Y is $NR^{7'}$, O or S;

—— represent optional double bonds;

each of $R^7$ and $R^{7'}$ is, independently, hydrogen, $C_1$-$C_6$alkyl, $C_7$-$C_{12}$arylalkyl, $C_7$-$C_{12}$heteroarylalkyl; or $R^7$ and one of $R^5$ or $R^6$ form a cyclic moiety containing 4-6 carbons, 1-3 nitrogens, 0-2 oxygens and 0-2 sulfurs, which may be optionally substituted with oxo or $C_1$-$C_6$alkyl; and n is 0 or 1.

Embodiments can include one or more of the following.

In certain embodiments, n can be 1.

X can be $NR^7$ and Y can be $NR^{7'}$. $R^7$ and $R^{7'}$ can each be, e.g., hydrogen or $CH_3$. One of $R^7$ and $R^{7'}$ can be hydrogen and the other can be $CH_3$.

$R^1$ and $R^2$ can form $C_5$-$C_{10}$cycloalkenyl.

$R^1$ and $R^2$ can form $C_6$-$C_{10}$aryl.

$R^1$ and $R^2$ can form $C_5$-$C_{10}$cycloalkenyl, which may be substituted with $R^5$, and $R^3$ and $R^4$ can form $C_6$-$C_{10}$aryl, which may be substituted with $R^6$.

In certain embodiments, the cycloalkenyl double bond can be between the carbon attached to $R^1$ and the carbon attached to $R^2$. $C_5$-$C_{10}$cycloalkenyl, e.g., $C_6$ or $C_7$cycloalkenyl, can be substituted with $R^5$ and $C_6$-$C_{10}$aryl can be substituted with $R^6$.

$R^6$ can be halo (e.g., chloro or bromo), $C_1$-$C_6$alkyl (e.g., $CH_3$), $C_1$-$C_6$haloalkyl (e.g., $CF_3$) or $C_1$-$C_6$haloalkoxy (e.g., $OCF_3$). $R^5$ can be for example, $C_1$-$C_6$alkyl substituted with a substituent such as an amino substituent, or aminocarbonyl (for example a substituted aminocarbonyl, substituted with substituents such an aryl, heteroaryl, cycloalkyl, heterocyloalkyl, aminocarbonyl, alkylaminocarbonyl, alkoxycarbonyl or other substituents. In each instances, the substituents can be further substituted with other substituents).

n can be 0.

$R^1$ and $R^2$ can form $C_5$-$C_{10}$cycloalkenyl.

$R^1$ and $R^2$ can form $C_6$-$C_{10}$aryl.

X can be $NR^7$, and $R^7$ can be, e.g., hydrogen or $CH_3$.

$R^1$ and $R^2$ can form $C_5$-$C_{10}$cycloalkenyl, which may be substituted with $R^5$, and $R^3$ and $R^4$ can form $C_6$-$C_{10}$aryl, which may be substituted with $R^6$.

In certain embodiments, the cycloalkenyl double bond can be between the carbon attached to $R^1$ and the carbon attached to $R^2$. $C_5$-$C_{10}$cycloalkenyl, e.g., $C_6$ or $C_7$cycloalkenyl, can be substituted with $R^5$ and $C_6$-$C_{10}$aryl can be substituted with $R^6$.

$R^6$ can be halo (e.g., chloro), $C_1$-$C_6$alkyl (e.g., $CH_3$), $C_1$-$C_6$haloalkyl (e.g., $CF_3$) or $C_1$-$C_6$haloalkoxy (e.g., $OCF_3$). $R^5$ can be aminocarbonyl.

n can be 0.

$R^1$ and $R^2$ can form $C_5$-$C_{10}$cycloalkenyl.

$R^1$ and $R^2$ can form $C_6$-$C_{10}$aryl.

X can be $NR^7$, and $R^7$ can be, e.g., hydrogen or $CH_3$.

$R^1$ and $R^2$ can form $C_5$-$C_{10}$cycloalkenyl, which may be substituted with $R^5$, and $R^3$ and $R^4$ can form $C_6$-$C_{10}$aryl, which may be substituted with $R^6$.

In certain embodiments, the cycloalkenyl double bond can be between the carbon attached to $R^1$ and the carbon attached to $R^2$. $C_5$-$C_{10}$cycloalkenyl, e.g., $C_6$ or $C_7$cycloalkenyl, can be substituted with $R^5$ and $C_6$-$C_{10}$aryl can be substituted with R. These compounds may have formula (II) or formula (III):

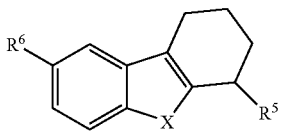

(II)

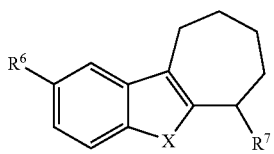

(III)

$R^6$ can be halo (e.g., chloro or bromo), $C_1$-$C_6$alkyl (e.g., $CH_3$), $C_1$-$C_6$haloalkyl (e.g., $CF_3$) or $C_1$-$C_6$haloalkoxy (e.g., $OCF_3$). $R^5$ can be aminocarbonyl. The compound may be a compound selected from FIG. 1 or compounds (IV), (V), (VI), or (VII).

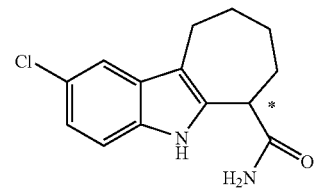

(IV)

(V)

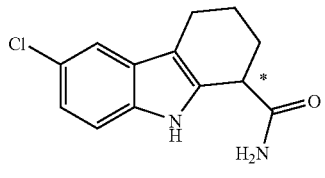

(VI)

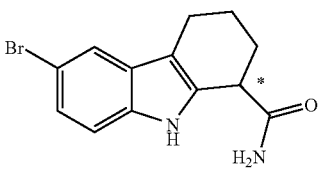

(VII)

In one instance, the compound can be a compound of formula (VI) having a high enantiomeric excess of a single isomer, wherein the optical rotation of the predominant isomer is negative, for example, −14.1 (c=0.33, DCM) or, for example, $[\alpha]_D^{25}$ −41.2° (c 0.96, $CH_3OH$). In a second instance, the compound can be a compound of formula (IV) having a high enantiomeric excess of a single isomer, wherein the optical rotation of the predominant isomer is negative. In some instances, a compound of formula (IV), (V), or (VII) is administered having a high enantiomeric excess of a single isomer, where the predominant isomer has the same absolute configuration as the negative isomer of the compound of formula (VI) as corresponds to the asterisk carbon shown above.

The compound can preferentially inhibit SIRT1 relative to a non-SIRT1 sirtuin, e.g., at least a 1.5, 2, 5, or 10 fold preference. The compound can have a Ki for SIRT1 that is less than 500, 100, 50, or 40 nM.

In some instances, the compound reduces the activity of a FOXO transcription factor such as FoxO1 or FoxO3.

The amount can be effective to ameliorate at least one symptom of the disorder. The disease or disorder can be, e.g., an age-associated disorder, a geriatric disorder, a disorder having an age-associated susceptibility factor, a neoplastic disorder, a non-neoplastic disorder, a neurological disorder, a cardiovascular disorder, a metabolic disorder, a dermatological disorder, or a dermatological tissue condition. In one embodiment, the disease or disorder can be a neurodegenerative disease or disorder in which the neurodegenerative disorder can be mediated at least in part by polyglutamine aggregation, e.g., Huntington's disease, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12). The neurodegenerative disorder can be Parkinson's or Alzheimer's.

The disease or disorder can be associated with or mediated at least in part by a sirtuin, e.g., the disease or disorder can be associated with or mediated at least in part by sirtuin-mediated deacetylation, e.g., excessive sirtuin activity or excessive levels of deacetylated p53, FoxO1, or FoxO3. The sirtuin can be SIRT1, e.g., human SIRT1.

The disease or disorder can be cancer. The amount can be, e.g., effective to reduce cancer or tumor cell mass, risk of metastasis, or rate of tumor cell growth. The amount can be effective to modulate (e.g., increase) apoptosis.

The disease or disorder can be a metabolic disease, such as metabolic syndrome or diabetes (e.g., type I diabetes or type II diabetes). The amount can be, for example, effective to increase insulin sensitivity, increase insulin secretion, or otherwise or lower levels of glucose. In some instances, the disease or disorder is related to a metabolic disease, such as cardiac disorder related diabetes.

The disease or disorder can be a fat related disorder such as obesity or dislipidemia or hyperlipidemia. The amount can be, for example, effective to reduce weight in a subject or to prevent weight gain in a subject.

The disease or disorder can be a neurological disorder such as Alzheimer's disease or Parkinson's disease. The amount can be, for example, effective to reduce one or more symptoms of the neurological disorder.

The method can include administering the compound more than once, e.g., repeatedly administering the compound. The compound can be administered in one or more boluses or continuous. The compound can be administered from without (e.g., by injection, ingestion, inhalation, etc), or from within, e.g., by an implanted device.

The method can include administering the compound locally.

The amount can be effective to increase acetylation of a sirtuin substrate (e.g., a nuclear protein, e.g., a histone or a transcription factor, e.g., p53, FoxO1, or FoxO3) in at least some cells of the subject.

The subject can be a mammal, e.g., a human.

The subject can be identified as being in need of such treatment or prevention.

The method further can further include identifying a subject in need of such treatment, e.g., by evaluating sirtuin activity in a cell of the subject, evaluating nucleotide identity in a nucleic acid of the subject that encodes a sirtuin, evaluating the subject for neoplastic cells or a neoplastic growth (e.g., a tumor), evaluating the genetic composition or expression of genes in a cell of the subject, e.g., a tumor biopsy.

The method can further include monitoring the subject, e.g., imaging the subject, evaluating tumor size in the subject, evaluating sirtuin activity in a cell of the subject, evaluating the subject for side effects, e.g., renal function.

In another aspect, this invention relates to a method of inhibiting sirtuin-mediated deacetylation of a substrate, such as a FoxO transcription factor. The method includes contacting a sirtuin with a compound of formula (I). The inhibiting can occur in vitro, in cell-free medium, in cell culture, or in an organism, e.g., a mammal, preferably a human.

In a further aspect, this invention relates to a method for evaluating a plurality of compounds, the method includes: a) providing library of compound that comprises a plurality of compounds, each having a formula (I); and b) for each of a plurality of compounds from the library, i) contacting the compound to a sirtuin test protein that comprises a functional deacetylase domain of a sirtuin; and ii) evaluating interaction between the compound and the sirtuin test protein in the presence of the compound.

Embodiments can include one or more of the following.

In one embodiment, evaluating the interaction between the compound and the sirtuin test protein includes evaluating enzymatic activity of the sirtuin test protein.

In one embodiment, evaluating the interaction between the compound and the sirtuin test protein includes evaluating a binding interaction between the compound and the sirtuin test protein The method can further include selecting, based on results of the evaluating, a compound that modulates deacetylase activity for a substrate. The substrate can be an acetylated lysine amino acid, an acetylated transcription factor (e.g., p53, FoxO1, or FoxO3) or an acetylated peptide thereof, an acetylated histone or an acetylated peptide thereof.

The method may also further include selecting, based on results of the evaluating, a compound that modulates sirtuin deacetylase activity of a substrate.

The method may also further include selecting, based on results of the evaluating, a compound that modulates the sirtuin.

In one aspect, this invention relates to a conjugate that includes: a targeting agent and a compound, wherein the targeting agent and the compound are covalently linked, and the compound has a formula (I).

Embodiments can include one or more of the following.

The targeting agent can be an antibody, e.g., specific for a cell surface protein, e.g., a cancer-specific antigen.

The targeting agent can be a synthetic peptide.

The targeting agent can be a domain of a naturally occurring protein.

In another aspect, this invention relates to a kit which includes: a compound described herein, and instructions for use for treating a disease described herein. The kit may further include a printed material comprising a rendering of the structure of the name of the compound.

In another aspect, this invention relates to a method of analyzing or designing structures, the method includes: providing a computer-generated image or structure (preferably a three dimensional image or structure) for a compound described herein, e.g., a compound of formula I, providing a computer-generated image or structure (preferably a three dimensional image or structure) for a second compound, e.g., another compound described herein, (e.g., a compound of formula I, NAD) or a target, e.g., e.g., a sirtuin (e.g., a human sirtuin, e.g., SIRT1, SIRT2, SIRT3, SIRT4, SIRT5, SIRT6, or SIRT7), or an off-target molecule, e.g., a sirtuin other than SIRT1, e.g., SIRT2 or SIRT3, or non-sirtuin histone deacetylase; and comparing the structure of the first and second compound, e.g., comparing the structure, e.g., a parameter related to bond angle, inter- or intra-molecular distance, position of an atom or moiety; e.g., a first or second generation compound—the predicted ability of compound to interact or inhibit a target or off-target molecule.

In a preferred embodiment, the structure is further evaluated in vitro, in vivo, or in silico with target or off-target molecule.

In a further aspect, this invention relates to a database, which includes: information about or identifying the structure, information about activity of the structure, e.g., in vitro, in vivo or in silico, e.g., at least 5, 10, 50, or 100 records.

In one aspect, this invention relates to a database, which includes a plurality of records, each record having: a) information about or identifying a compound that has a structure described herein, e.g., a structure of formula I; and b) information about a parameter of a patient, the parameter relating to a neoplastic disorder or a neurodegenerative disorder, e.g. a patient parameter.

In one aspect, this invention relates to a method of evaluating a compound, the method includes: providing a first compound that has a structure of formula I, or a data record having information about the structure; providing a second compound that has a structure of formula I or not having formula I, or a data record having information about the structure; evaluating a first compound and the second compound, e.g., in vivo, in vitro, or in silico; and comparing the ability of a second compound to interact, e.g., inhibit a sirtuin, e.g., SIRT1, with a first compound, thereby evaluating ability of the second compound to interact with SIRT1.

In other aspects, the invention relates to a composition comprising a compound of any of the formulae herein, and a pharmaceutically acceptable carrier. The composition may contain an additional therapeutic agent, e.g., an anti-tumor agent or a neurodegenerative disease agent. Also within the scope of this invention is the use of such a composition for the manufacture of a medicament for the just-mentioned use.

In another aspect, the invention is a method for treating or preventing a disease characterized by unwanted cell proliferation, e.g., cancer, e.g., a p53 dependent cancer or a p53 independent cancer, in a subject. The method includes administering a SIRT1 antagonist. For example, the SIRT1 antagonist can be one or more of: antisense of SIRT1, RNAi, an antibody, an intrabody, and other compounds identified by a method described herein, e.g., compounds that induce apoptosis in a SIRT1 expressing cell.

In a preferred embodiment, the method includes administering a SIRT1 antagonist in combination with one or more therapeutic agents, e.g., a therapeutic agent or agent for treating unwanted cell proliferation. The therapeutic agents include, for example, one or more of a chemotherapeutic agent, a radioisotope, and a cytotoxin. Examples of chemotherapeutic agents include taxol, cytochalasin B, gramicidin D, mitomycin, etoposide, tenoposide, vincristine, vinblastine, colchicin, busulfan, cisplatin, doxorubicin, daunorubicin, dihydroxy anthracin dione, mitoxantrone, mithramycin, chlorambucil, gemcitabine, actinomycin, procaine, tetracaine, lidocaine, propranolol, puromycin, maytansinoids and analogs or homologs thereof. Additional therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioisotopes can include alpha, beta and/or gamma emitters. Examples of radioisotopes include $^{212}$Bi, $^{213}$Bi, $^{131}$I, $^{211}$At, $^{186}$Re, $^{90}$Y and $^{117}$Lu.

The SIRT1 antagonist and the therapeutic agents can be administered simultaneously or sequentially.

Also within the scope of this invention is a packaged product. The packaged product includes a container, one of the aforementioned compounds in the container, and a legend (e.g., a label or insert) associated with the container and indicating administration of the compound for treating a disorder described herein (e.g., cancer or neurodegenerative disorders), diseases, or disease symptoms, including any of those delineated herein.

The subject can be a mammal, preferably a human. The subject can also be a non-human subject, e.g., an animal model. In certain embodiments the method can further include identifying a subject. Identifying a subject in need of such treatment can be in the judgment of a subject or a health care professional and can be subjective (e.g., opinion) or objective (e.g., measurable by a test or diagnostic method).

The term "mammal" includes organisms, which include mice, rats, cows, sheep, pigs, rabbits, goats, and horses, monkeys, dogs, cats, and preferably humans.

The term "treating" or "treated" refers to administering a compound described herein to a subject with the purpose to cure, heal, alleviate, relieve, alter, remedy, ameliorate, improve, or affect a disease, e.g., an infection, the symptoms of the disease or the predisposition toward the disease.

An effective amount of the compound described above may range from about 0.1 mg/Kg to about 500 mg/Kg, alternatively from about 1 to about 50 mg/Kg. Effective doses will also vary depending on route of administration, as well as the possibility of co-usage with other agents.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —CH$_2$—, —CH$_2$CH$_2$—, and —CH$_2$CH$_2$CH$_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively. The term "aralkylamino" refers to a —NH(aralkyl) radical. The term alkylaminoalkyl refers to a (alkyl)NH-alkyl-radical; the term dialkylaminoalkyl refers to a (alkyl)$_2$N-alkyl-radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Any ring atom can be substituted (e.g., by one or more substituents). The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, quinolinyl, and pyrrolidinyl.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon may optionally be the point of attachment of the cycloalkenyl substituent. Any ring atom can be substituted (e.g., by one or more substituents). The cycloalkenyl groups can contain fused rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The unsaturated carbon or the heteroatom may optionally be the point of attachment of the heterocycloalkenyl substituent. Any ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents).

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The terms "aminocarbonyl," alkoxycarbonyl," hydrazinocarbonyl, and hydroxyaminocarbonyl refer to the radicals —C(O)NH$_2$, —C(O)O(alkyl), —C(O)NH$_2$NH$_2$, and —C(O)NH$_2$NH$_2$, respectively.

The term "amindo" refers to a —NHC(O)— radical, wherein N is the point of attachment.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as CF$_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as OCF$_3$), halo, hydroxy, carboxy, carboxylate, cyano, nitro, amino, alkyl amino, SO$_3$H, sulfate, phosphate, methylenedioxy (—O—CH$_2$—O— wherein oxygens are attached to vicinal atoms), ethylenedioxy, oxo, thioxo (e.g., C=S), imino (alkyl, aryl, aralkyl), S(O)$_n$ alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The details of one or more embodiments of the invention are set forth in the accompanying drawings and the description below. Other features, objects, and advantages of the invention will be apparent from the description and drawings, and from the claims.

All references cited herein, whether in print, electronic, computer readable storage media or other form, are expressly incorporated by reference in their entirety, including but not limited to, abstracts, articles, journals, publications, texts, treatises, internet web sites, databases, patents, patent applications and patent publications. U.S. Ser. No. 60/502,811, filed Sep. 12, 2003, is also incorporated by reference in its entirety.

DESCRIPTION OF DRAWINGS

FIG. 1 is a table of representative compounds and data.

DETAILED DESCRIPTION

Structure of Compounds

Figure 2:
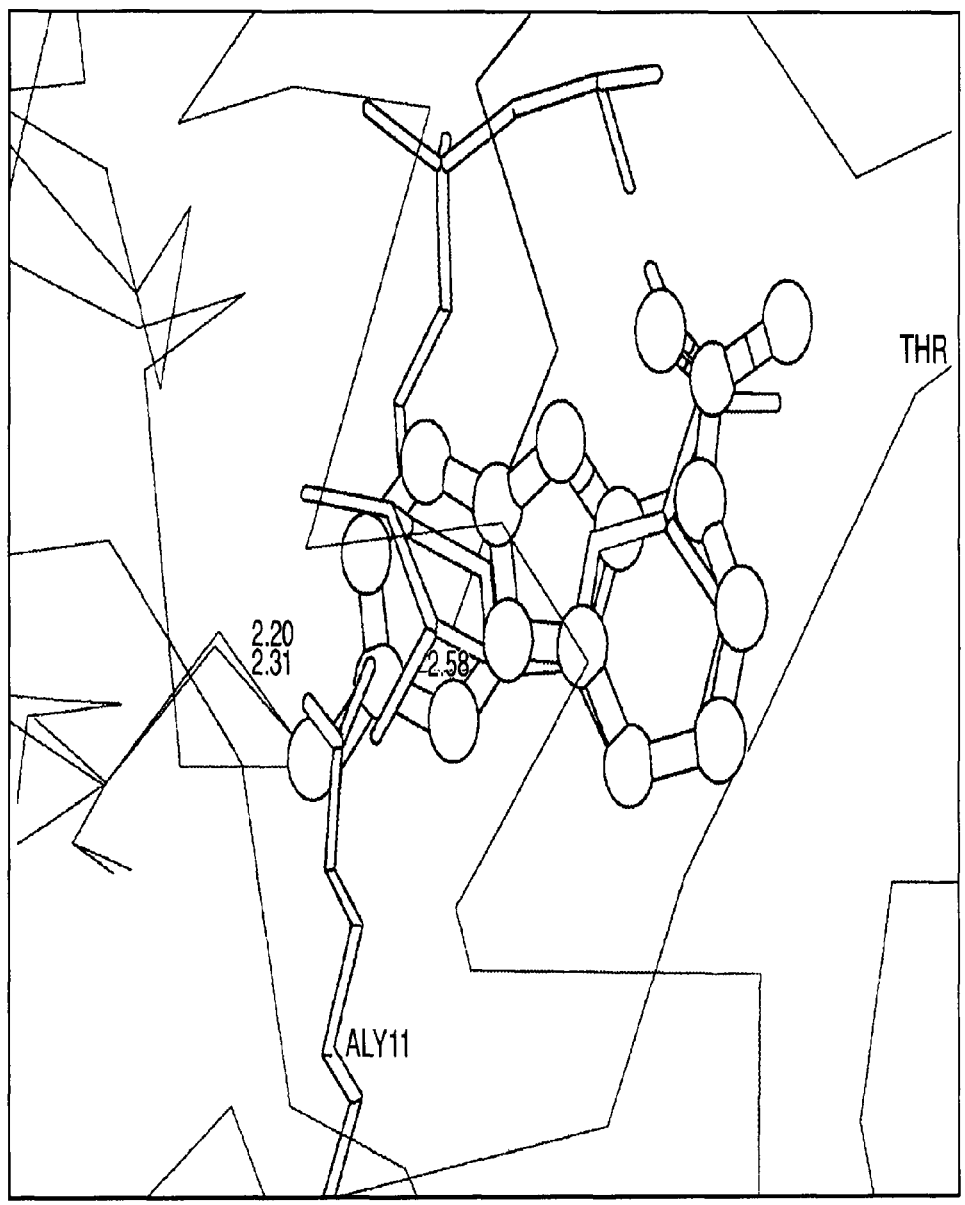
FIG. 2 is a computer-generated model showing one possible orientation of compound 8 bound in the active site of SIRT.

Compounds that can be used in practicing the invention have a general formula (I) and contain a substituted five or six membered ring core containing one or two, respectively, oxygen, nitrogen, or sulfur atoms as a constituent atom of the ring, e.g., X and Y in formula (I) below.

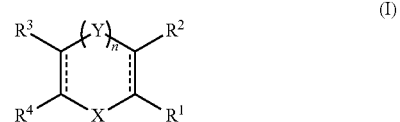

(I)

Any ring carbon atom can be substituted. For example, $R^1$, $R^2$, $R^3$, and $R^4$ may include without limitation substituted or unsubstituted alkyl, cycloalkyl, alkenyl, alkynyl, heterocyclyl, heterocycloalkenyl, cycloalkenyl, aryl, heteroaryl, etc. The five or six membered ring core may be saturated, i.e. containing no double bonds, or partially or fully saturated, i.e. one or two double bonds respectively. When n=0, "X" may be oxygen, sulfur, or nitrogen, e.g., $NR^7$. The substituent $R^7$ can be without limitation hydrogen, alkyl, e.g., C1, C2, C3, C4 alkyl, SO$_2$(aryl), acyl, or the ring nitrogen may form part of a carbamate, or urea group. When n=1, X can be $NR^7$, O, or S; and Y can be $NR^7$, O or S. X and Y can be any combination of heteroatoms, e.g., N, N, N, O, N, S, etc.

A preferred subset of compounds of formula (I) includes those having one, or preferably, two rings that are fused to the five or six membered ring core, e.g., $R^1$ and $R^2$, together with the carbons to which they are attached, and/or $R^3$ and $R^4$, together with the carbons to which they are attached, can form, e.g., $C_5$-$C_{10}$cycloalkyl (e.g., C5, C6, or C7), $C_5$-$C_{10}$heterocyclyl (e.g., C5, C6, or C7), $C_5$-$C_{10}$cycloalkenyl (e.g., C5, C6, or C7), $C_5$-$C_{10}$heterocycloalkenyl (e.g., C5, C6, or C7), $C_6$-$C_{10}$aryl (e.g., C6, C8 or C10), or $C_6$-$C_{10}$heteroaryl (e.g., C5 or C6). Fused ring combinations may include without limitation one or more of the following:

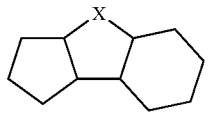
A

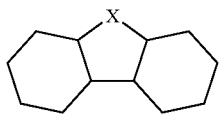
B

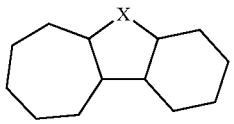
C

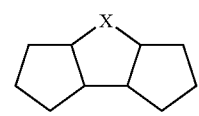
D

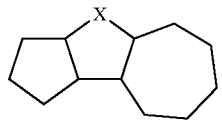
E

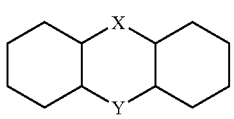
F

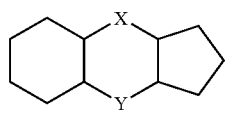
G

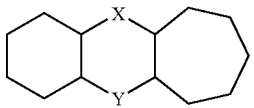
H

Preferred combinations include B, e.g. having $C_6$aryl and $C_6$cycloalkenyl (B1), and C, e.g. having $C_6$aryl and $C_7$cycloalkenyl (C1):

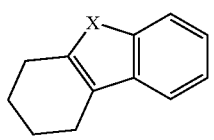
B1

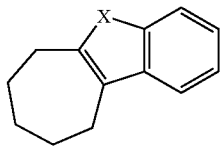
C1

Each of these fused ring systems may be optionally substituted with substituents, which may include without limitation halo, hydroxy, $C_1$-$C_{10}$alkyl (C1, C2,C3,C4,C5,C6,C7, C8,C9,C10), $C_1$-$C_6$haloalkyl (C1,C2,C3,C4,C5,C6), $C_1$-$C_{10}$alkoxy (C1, C2,C3,C4,C5,C6,C7,C8,C9,C10), $C_1$-$C_6$haloalkoxy (C1,C2,C3,C4,C5,C6), $C_6$-$C_{10}$aryl (C6, C7,C8,C9,C10), $C_5$-$C_{10}$heteroaryl (C5,C6,C7,C8,C9,C10), $C_7$-$C_{12}$ aralkyl (C7,C8,C9,C10,C11,C12), $C_7$-$C_{12}$heteroaralkyl (C7,C8,C9,C10,C11,C12), $C_3$-$C_8$heterocyclyl (C3,C4,C5,C6,C7,C8), $C_2$-$C_{12}$alkenyl (C2,C3,C4,C5,C6,C7,C8,C9,C10,C11, C12), $C_2$-$C_{12}$alkynyl (C2,C3,C4,C5,C6,C7,C8,C9,C10,C11, C12), $C_5$-$C_{10}$cycloalkenyl (C5,C6,C7,C8,C9,C10), $C_5$-$C_{10}$heterocycloalkenyl (C5,C6,C7,C8,C9,C10), carboxy, carboxylate, cyano, nitro, amino, $C_1$-$C_6$alkyl amino (C1,C2, C3,C4,C5,C6), $C_1$-$C_6$ dialkyl amino (C1,C2,C3,C4,C5,C6), mercapto, $SO_3H$, sulfate, $S(O)NH_2$, $S(O)_2NH_2$, phosphate, $C_1$-$C_4$alkylenedioxy (C1, C2,C3,C4), oxo, acyl, aminocarbonyl, $C_1$-$C_6$alkyl aminocarbonyl (C1,C2,C3,C4,C5,C6), $C_1$-$C_6$ dialkyl aminocarbonyl (C1, C2,C3,C4,C5,C6), $C_1$-$C_{10}$alkoxycarbonyl (C1, C2,C3,C4,C5,C6,C7,C8,C9, C10), $C_1$-$C_{10}$ thioalkoxycarbonyl (C1, C2,C3,C4,C5,C6,C7, C8,C9,C10), hydrazinocarbonyl, $C_1$-$C_6$alkyl hydrazinocarbonyl (C1,C2,C3,C4,C5,C6), $C_1$-$C_6$ dialkyl hydrazinocarbonyl (C1,C2,C3,C4,C5,C6), hydroxyaminocarbonyl, etc. Preferred substituents include halo (e.g., fluoro, chloro, bromo), $C_1$-$C_{10}$alkyl (e.g., C1, C2, C3, C4, C5, C6, C7, C8, C9, C10), $C_1$-$C_6$haloalkyl (e.g., C1, C2, C3, C4, C5, C6, e.g., $CF_3$), $C_1$-$C_6$haloalkoxyl (e.g., C1, C2, C3, C4, C5, C6, e.g., $OCF_3$), or aminocarbonyl. The substitution pattern on the two fused rings may be selected as desired, e.g., one ring may be substituted and the other is not, or both rings may be substituted with 1-5 substitutents (1, 2, 3, 4, 5 substitutents). The number of substituents on each ring may be the same or different. Preferred substitution patterns are shown below:

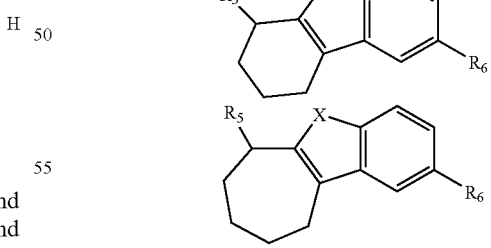

In certain embodiments, when n is 0 and X is $NR^7$, the nitrogen substituent $R^7$ can form a cyclic structure with one of the fused rings containing, e.g., 4-6 carbons, 1-3 nitrogens, 0-2 oxygens and 0-2 sulfurs. This cyclic structure may optionally be substituted with oxo or $C_1$-$C_6$alkyl.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Exemplary compounds include those depicted in Table 1 below*:

*Compounds having activity designated with an A have an $IC_{50}$ of less than 1.0 µM. Compounds having activity designated with a B have an $IC_{50}$ between 1.0 µM and 10.0 pM. Compounds having activity designated with a C have an $IC_{50}$ greater than 10.0 µM. Compounds designated with a D were not tested in this assay.

TABLE 1

Exemplary compounds

| Compound number | Chemical name | Ave. SirT1 p53-382 IC50 (µM) |
|---|---|---|
| 1 | 7-Chloro-1,2,3,4-tetrahydro-cyclopenta[b]indole-3-carboxylic acid amide | A |
| 2 | 2,3,4,9-Tetrahydro-1H-b-carboline-3-carboxylic acid amide | C |
| 3 | 6-Bromo-2,3,4,9-tetrahydro-1H-carbazole-2-carboxylic acid amide | B |
| 4 | 6-Methyl-2,3,4,9-tetrahydro-1H-carbazole-1-carboxylic acid amide | A |
| 5 | 2,3,4,9-Tetrahydro-1H-carbazole-1-carboxylic acid amide | B |
| 6 | 2-Chloro-5,6,7,8,9,10-hexahydro-cyclohepta[b]indole-6-carboxylic acid amide | A |
| 7 | 6-Chloro-2,3,4,9-tetrahydro-1H-carbazole-1-carboxylic acid hydroxyamide | C |
| 8 | 6-Chloro-2,3,4,9-tetrahydro-1H-carbazole-1-carboxylic acid amide | A |
| 9 | 6-Chloro-2,3,4,9-tetrahydro-1H-carbazole-2-carboxylic acid amide | C |
| 10 | 1,2,3,4-Tetrahydro-cyclopenta[b]indole-3-carboxylic acid amide | B |
| 11 | 6-Chloro-2,3,4,9-tetrahydro-1H-carbazole-1-carboxylic acid (5-chloro-pyridin-2-yl)-amide | B |
| 12 | 1,6-Dimethyl-2,3,4,9-tetrahydro-1H-carbazole-1-carboxylic acid amide | C |
| 13 | 6-Trifluoromethoxy-2,3,4,9-tetrahydro-1H-carbazole-2-carboxylic acid amide | C |
| 14 | 6-Chloro-2,3,4,9-tetrahydro-1H-carbazole-1-carboxylic acid diethylamide | D |
| 15 | 6-Chloro-2,3,4,9-tetrahydro-1H-carbazole-1-carboxylic acid carbamoylmethyl-amide | D |
| 16 | 8-Carbamoyl-6,7,8,9-tetrahydro-5H-carbazole-1-carboxylic acid | D |
| 17 | 6-Methyl-2,3,4,9-tetrahydro-1H-carbazole-1-carboxylic acid | D |
| 18 | 8-Carbamoyl-2,3,4,9-tetrahydro-1H-carbazole-1-carboxylic acid ethyl ester | D |
| 19 | [(6-Chloro-2,3,4,9-tetrahydro-1H-carbazole-1-carbonyl)-amino]-acetic acid ethyl ester | D |
| 20 | 9-Benzyl-2,3,4,9-tetrahydro-1H-carbazole-1-carboxylic acid amide | D |
| 21 | 6-Chloro-2,3,4,9-tetrahydro-1H-carbazole-1-carboxylic acid methyl ester | D |
| 22 | 6-Chloro-2,3,4,9-tetrahydro-1H-carbazole-1-carboxylic acid | D |
| 23 | C-(6-Methyl-2,3,4,9-tetrahydro-1H-carbazol-1-yl)-methylamine | D |
| 24 | 6,9-Dimethyl-2,3,4,9-tetrahydro-1H-carbazole-1-carboxylic acid amide | D |
| 25 | 7-Methyl-1,2,3,4-tetrahydro-cyclopenta[b]indole-3-carboxylic acid amide | D |
| 26 | 6-Chloro-2,3,4,9-tetrahydro-1H-carbazole-1-carboxylic acid ethylamide | D |
| 27 | 2-(1-Benzyl-3-methylsulfanyl-1H-indol-2-yl)-N-p-tolyl-acetamide | D |
| 28 | N-Benzyl-2-(1-methyl-3-phenylsulfanyl-1H-indol-2-yl)-acetamide | D |

TABLE 1-continued

Exemplary compounds

| Compound number | Chemical name | Ave. SirT1 p53-382 IC50 (µM) |
|---|---|---|
| 29 | N-(4-Chloro-phenyl)-2-(1-methyl-3-phenylsulfanyl-1H-indol-2-yl)-acetamide | D |
| 30 | N-(3-Hydroxy-propyl)-2-(1-methyl-3-phenylsulfanyl-1H-indol-2-yl)-acetamide | D |
| 31 | 2-(1-Benzyl-3-phenylsulfanyl-1H-indol-2-yl)-N-(3-hydroxy-propyl)-acetamide | D |
| 32 | 2-(1-Benzyl-3-methylsulfanyl-1H-indol-2-yl)-N-(4-methoxy-phenyl)-acetamide | D |
| 33 | 2-(1-Benzyl-1H-indol-2-yl)-N-(4-methoxy-phenyl)-acetamide | D |
| 34 | 2-(1-Methyl-3-methylsulfanyl-1H-indol-2-yl)-N-p-tolyl-acetamide | D |
| 35 | 2-(1-Benzyl-3-methylsulfanyl-1H-indol-2-yl)-N-(2-chloro-phenyl)-acetamide | D |
| 36 | 2-(1,5-Dimethyl-3-methylsulfanyl-1H-indol-2-yl)-N-(2-hydroxy-ethyl)-acetamide | D |
| 37 | (6-Chloro-2,3,4,9-tetrahydro-1H-carbazol-1-yl)-[4-(furan-2-carbonyl)-piperazin-1-yl]-methanone | D |
| 38 | 2-(1-Benzyl-1H-indol-2-yl)-N-(2-chloro-phenyl)-acetamide | D |
| 39 | 6-Chloro-2,3,4,9-tetrahydro-1H-carbazole-1-carboxylic acid ethyl ester | D |
| 40 | 6-Chloro-9-methyl-2,3,4,9-tetrahydro-1H-carbazole-4-carboxylic acid ethyl ester | D |
| 41 | 5,7-Dichloro-2,3,4,9-tetrahydro-1H-carbazole-1-carboxylic acid ethyl ester | D |
| 42 | 7-Chloro-2,3,4,9-tetrahydro-1H-carbazole-1-carboxylic acid ethyl ester | D |
| 43 | 5,7-Dichloro-2,3,4,9-tetrahydro-1H-carbazole-1-carboxylic acid | D |
| 44 | 6-Chloro-9-methyl-2,3,4,9-tetrahydro-1H-carbazole-4-carboxylic acid | D |
| 45 | 6-Chloro-9-methyl-2,3,4,9-tetrahydro-1H-carbazole-4-carboxylic acid amide | D |
| 46 | 6-Morpholin-4-yl-2,3,4,9-tetrahydro-1H-carbazole-1-carboxylic acid ethyl ester | D |
| 47 | 6-Morpholin-4-yl-2,3,4,9-tetrahydro-1H-carbazole-1-carboxylic acid amide | D |
| 48 | 6-Bromo-2,3,4,9-tetrahydro-1H-carbazole-1-carboxylic acid ethyl ester | D |
| 49 | 6-Fluoro-2,3,4,9-tetrahydro-1H-carbazole-1-carboxylic acid ethyl ester | D |
| 50 | 3-Carbamoyl-1,3,4,9-tetrahydro-b-carboline-2-carboxylic acid tert-butyl ester | D |
| 51 | 6-Chloro-2,3,4,9-tetrahydro-1H-carbazole-1-carboxylic acid (1-phenyl-ethyl)-amide | D |
| 52 | 7,8-Difluoro-2,3,4,9-tetrahydro-1H-carbazole-1-carboxylic acid amide | D |
| 53 | 6-bromo-2,3,4,9-tetrahydro-1H-carbazole-1-carboxylic acid | D |
| 54 | 6-hydroxy-2,3,4,9-tetrahydro-1H-carbazole-1-carboxylic acid | C |
| 55 | 6-bromo-2,3,4,9-tetrahydro-1H-carbazole-2-carboxamide | B |
| 56 | 6-chloro-2,3,4,9-tetrahydro-1H-pyrido[3,4-b]indole-1-carboxamide | C |
| 57 | 6-bromo-2,3,4,9-tetrahydro-1H-pyrido[3,4-b]indole-1-carboxamide | D |
| 58 | 2-acetyl-6-chloro-2,3,4,9-tetrahydro-1H-pyrido[3,4-b]indole-1-carboxamide | C |

Compounds that can be useful in practicing this invention can be identified through both in vitro (cell and non-cell based) and in vivo methods. A description of these methods is described in the Examples.

Synthesis of Compounds

The compounds described herein can be obtained from commercial sources (e.g., Asinex, Moscow, Russia; Bionet, Camelford, England; ChemDiv, SanDiego, Calif.; Comgenex, Budapest, Hungary; Enamine, Kiev, Ukraine; IF Lab, Ukraine; Interbioscreen, Moscow, Russia; Maybridge, Tintagel, UK; Specs, The Netherlands; Timtec, Newark, Del.; Vitas-M Lab, Moscow, Russia) or synthesized by conventional methods as shown below using commercially available starting materials and reagents. For example, exemplary compound 4 can be synthesized as shown in Scheme 1 below.

*Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may contain one or more asymmetric centers and thus occur as racemates and racemic

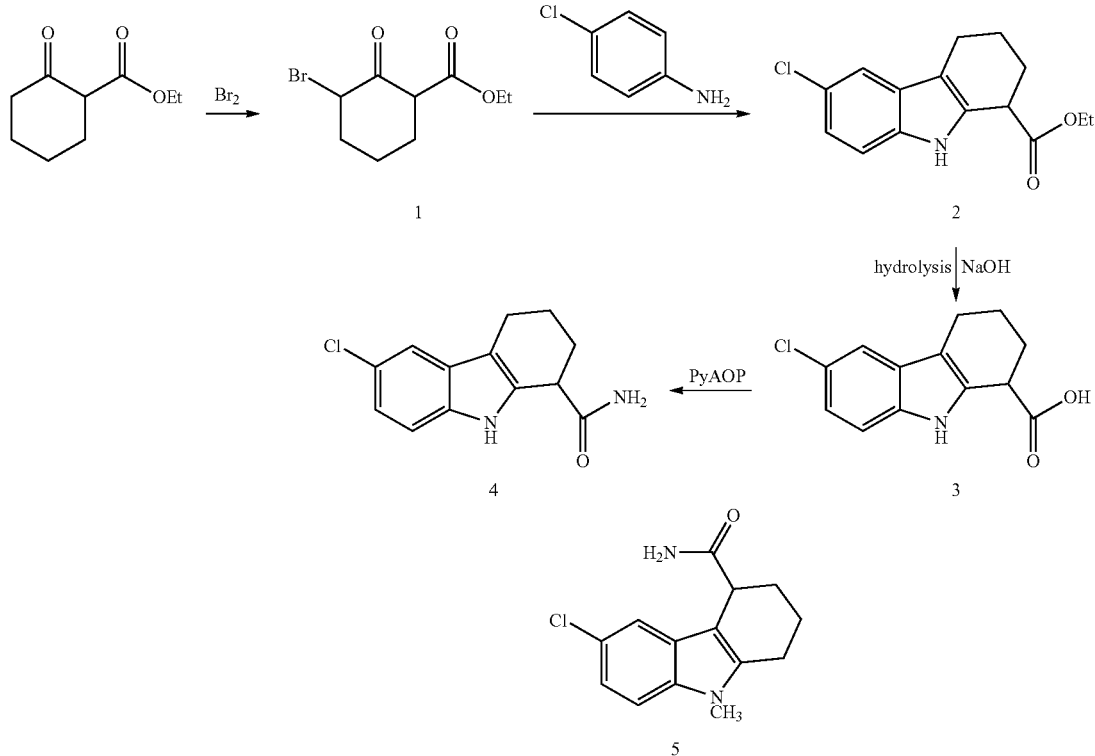

Scheme 1

Brominated β-keto ester 1 can be condensed with 4-chloroaniline followed by cyclization can afford indole 2. Ester saponification can afford acid 3. Finally amination with PyAOP can yield the amide 4. Other methods are known in the art, see, e.g., U.S. Pat. No. 3,859,304, U.S. Pat. No. 3,769,298, *J. Am. Chem. Soc.* 1974, 74, 5495. The synthesis above can be extended to other anilines, e.g., 3,5-dichloroaniline, 3-chloroaniline, and 4-bromoaniline. Regioisomeric products, e.g., 5, may be obtained using N-substituted anilines, e.g., 4-chloro-N-methylaniline.

The compounds described herein can be separated from a reaction mixture and further purified by a method such as column chromatography, high-pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and* mixtures, single enantiomers, individual diastereomers and diastereomeric mixtures. All such isomeric forms of these compounds are expressly included in the present invention. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Techniques useful for the separation of isomers, e.g., stereoisomers are within skill of the art and are described in Eliel, E. L.; Wilen, S. H.; Mander, L. N. *Stereochemistry of Organic Compounds*, Wiley Interscience, NY, 1994. For example compound 3 or 4 can be resolved to a high enantiomeric excess (e.g., 60%, 70%, 80%, 85%, 90%, 95%, 99% or greater) via formation of diasteromeric salts, e.g. with a chiral base, e.g., (+) or (−) α-methylbenzylamine, or via high performance liquid chromatography using a chiral column. In some embodiments, the crude product 4, is purified directly on a chiral column to provide enantiomerically enriched compound.

For purposes of illustration, enantiomers of compound 4 are shown below.

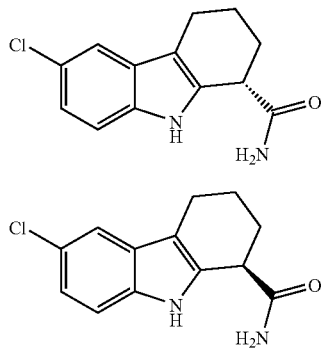

In some instances, the compounds disclosed herein are administered where one isomer (e.g., the R isomer or S isomer) is present in high enantiomeric excess. In general, the isomer of compound 4 having a negative optical rotation, e.g., −14.1 (c=0.33, DCM) or $[\alpha]_D^{25}$ −41.180 (c 0.960, $CH_3OH$) has greater activity against the SirT1 enzyme than the enantiomer that has a positive optical rotation of +32.8 (c=0.38, DCM) or $[\alpha]_D^{25}$ +22.720 (c 0.910, $CH_3OH$). Accordingly, in some instances, it is beneficial to administer to a subject a compound 4 having a high enantiomeric excess of the isomer having a negative optical rotation to treat a disease.

While the enantiomers of compound 4 provide one example of a stereoisomer, other stereoisomers are also envisioned, for example as depicted in compounds 6 and 7 below.

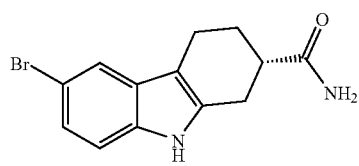

6

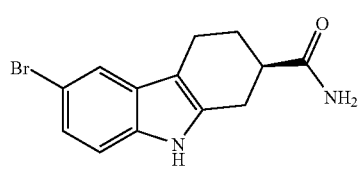

6

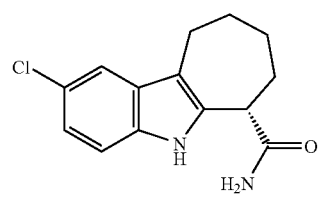

7

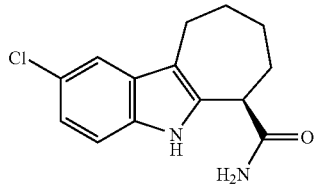

7

As with the compound of formula 4, in some instances it is beneficial to administer to a subject an isomer of compounds 6 or 7 that has a greater affinity for SirT1 than its enantiomer. For example, in some instances, it is beneficial to administer a compound 7, enriched with the (−) optical rotamer, wherein the amide (or other substituent) has the same configuration as the negative isomer of compound 4.

In some instances, it is beneficial to administer a compound having the one of the following structures where the stereochemical structure of the amide (or other substituent) corresponds to the amide in compound 4 having a negative optical rotation.

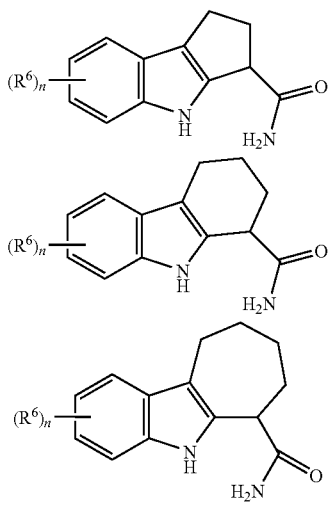

(n is an integer from 0 to 4.)

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds of this invention may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, A. W., *Curr. Opin. Chem. Bio.*, (1997) 1, 60. Thus, one embodiment relates to a method of using the compounds described herein for generating derivatives or chemical libraries comprising: 1) providing a body comprising a plurality of wells; 2) providing one or more compounds identified by methods described herein in each well; 3) providing an additional one or more chemicals in each well; 4) isolating the resulting one or more products from each well. An alternate embodiment relates to a method of using the compounds described herein for generating derivatives or chemical libraries comprising: 1) providing one or more compounds described herein attached to a solid support; 2) treating the one or more compounds identified by methods described herein attached to a solid support with one or more additional chemicals; 3) isolating the resulting one or more products from the solid support. In the methods described above, "tags" or identifier or labeling moieties may be attached to and/or detached from the compounds described herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

Sirtuins

Sirtuins are members of the Silent Information Regulator (SIR) family of genes.

Sirtuins are proteins that include a SIR2 domain as defined as amino acids sequences that are scored as hits in the Pfam family "SIR2"-PF02146. This family is referenced in the INTERPRO database as INTERPRO description (entry IPR003000). To identify the presence of a "SIR2" domain in a protein sequence, and make the determination that a polypeptide or protein of interest has a particular profile, the amino acid sequence of the protein can be searched against the Pfam database of HMMs (e.g., the Pfam database, release 9) using the default parameters (http://www.sanger.ac.uk/Software/Pfam/HMM_search). The SIR2 domain is indexed in Pfam as PF02146 and in INTERPRO as INTERPRO description (entry IPR003000). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in "The Pfam Protein Families Database" Bateman A, Birney E, Cerruti L, Durbin R, Etwiller L, Eddy S R, Griffiths-Jones S, Howe K L, Marshall M, Sonnhammer E L (2002) Nucleic Acids Research 30(1):276-280 and Sonhammer et al. (1997) *Proteins* 28(3): 405-420 and a detailed description of HMMs can be found, for example, in Gribskov et al.(1990) *Meth. Enzymol.* 183: 146-159; Gribskov et al. (1987) *Proc. Nat. Acad. Sci. USA* 84:4355-4358; Krogh et al. (1994) *J. Mol. Biol.* 235:1501-1531; and Stultz et al. (1993) *Protein Sci.* 2:305-314.

The proteins encoded by members of the SIR2 gene family may show high sequence conservation in a 250 amino acid core domain. A well-characterized gene in this family is *S. cerevisiae* SIR2, which is involved in silencing HM loci that contain information specifying yeast mating type, telomere position effects and cell aging (Guarente, 1999; Kaeberlein et al., 1999; Shore, 2000). The yeast Sir2 protein belongs to a family of histone deacetylases (reviewed in Guarente, 2000; Shore, 2000). The Sir2 protein is a deacetylase which can use NAD as a cofactor (Imai et al., 2000; Moazed, 2001; Smith et al., 2000; Tanner et al., 2000; Tanny and Moazed, 2001). Unlike other deacetylases, many of which are involved in gene silencing, Sir2 is relatively insensitive to histone deacetylase inhibitors like trichostatin A (TSA) (Imai et al., 2000; Landry et al., 2000a; Smith et al., 2000). Mammalian Sir2 homologs, such as SIRT1, have NAD-dependent deacetylase activity (Imai et al., 2000; Smith et al., 2000).

Exemplary mammalian sirtuins include SIRT1, SIRT2, and SIRT3, e.g., human SIRT1, SIRT2, and SIRT3. A compound described herein may inhibit one or more activities of a mammalian sirtuin, e.g., SIRT1, SIRT2, or SIRT3, e.g., with a Ki of less than 500, 200, 100, 50, or 40 nM. For example, the compound may inhibit deacetylase activity, e.g., with respect to a natural or artificial substrate, e.g., a substrate described herein, e.g., as follows.

Natural substrates for SIRT1 include histones, p53, and FoxO transcription factors such as FoxO1 and FoxO3. SIRT1 proteins bind to a number of other proteins, referred to as "SIRT1 binding partners." For example, SIRT1 binds to p53 and plays a role in the p53 pathway, e.g., K370, K371, K372, K381, and/or K382 of p53 or a peptide that include one or more of these lysines. For example, the peptide can be between 5 and 15 amino acids in length. SIRT1 proteins can also deacetylate histones. For example, SIRT1 can deacetylate lysines 9 or 14 of histone H3 or small peptides that include one or more of these lysines. Histone deacetylation alters local chromatin structure and consequently can regulate the transcription of a gene in that vicinity. Many of the SIRT1 binding partners are transcription factors, e.g., proteins that recognize specific DNA sites. For example, SirT1 deacetylates and downregulates forkhead proteins (i.e., FoxO proteins). Interaction between SIRT1 and SIRT1 binding partners can deliver SIRT1 to specific regions of a genome and can result in a local manifestation of substrates, e.g., histones and transcription factors localized to the specific region.

Natural substrates for SIRT2 include tubulin, e.g., alpha-tubulin. See, e.g., North et al. Mol. Cell. 2003 February; 11(2):437-44. Exemplary substrates include a peptide that includes lysine 40 of alpha-tubulin.

Still other exemplary sirtuin substrates include cytochrome c and acetylated peptides thereof.

The terms "SIRT1 protein" and "SIRT1 polypeptide" are used interchangeably herein and refer a polypeptide that is at least 25% identical to the 250 amino acid conserved SIRT1 catalytic domain, amino acid residues 258 to 451 of SEQ ID NO:1. SEQ ID NO:1 depicts the amino acid sequence of human SIRT1. In preferred embodiments, a SIRT1 polypeptide can be at least 30, 40, 50, 60, 70, 80, 85, 90, 95, 99% homologous to SEQ ID NO:1 or to the amino acid sequence between amino acid residues 258 and 451 of SEQ ID NO:1. In other embodiments, the SIRT1 polypeptide can be a fragment, e.g., a fragment of SIRT1 capable of one or more of: deacetylating a substrate in the presence of NAD and/or a NAD analog and capable of binding a target protein, e.g., a transcription factor. Such functions can be evaluated, e.g., by the methods described herein. In other embodiments, the SIRT1 polypeptide can be a "full length" SIRT1 polypeptide. The term "full length" as used herein refers to a polypeptide that has at least the length of a naturally-occurring SIRT1 polypeptide (or other protein described herein). A "full length" SIRT1 polypeptide or a fragment thereof can also include other sequences, e.g., a purification tag, or other attached compounds, e.g., an attached fluorophore, or cofactor. The term "SIRT1 polypeptides" can also include sequences or variants that include one or more substitutions, e.g., between one and ten substitutions, with respect to a naturally occurring Sir2 family member. A "SIRT1 activity" refers to one or more activity of SIRT1, e.g., deacetylation of a substrate (e.g., an amino acid, a peptide, or a protein), e.g., transcription factors (e.g., p53) or histone proteins, (e.g., in the presence of a cofactor such as NAD and/or an NAD analog) and binding to a target, e.g., a target protein, e.g., a transcription factor.

As used herein, a "biologically active portion" or a "functional domain" of a protein includes a fragment of a protein of interest which participates in an interaction, e.g., an intramolecular or an inter-molecular interaction, e.g., a binding or catalytic interaction. An inter-molecular interaction can be a specific binding interaction or an enzymatic interaction (e.g., the interaction can be transient and a covalent bond is formed or broken). An inter-molecular interaction can be between the protein and another protein, between the protein and another compound, or between a first molecule and a second molecule of the protein (e.g., a dimerization interaction). Biologically active portions/functional domains of a protein include peptides comprising amino acid sequences sufficiently homologous to or derived from the amino acid sequence of the protein which include fewer amino acids than the full length, natural protein, and exhibit at least one activity of the natural protein. Biological active portions/functional domains can be identified by a variety of techniques including truncation analysis, site-directed mutagenesis, and proteolysis. Mutants or proteolytic fragments can be assayed for activity by an appropriate biochemical or biological (e.g., genetic) assay. In some embodiments, a functional domain is independently folded. Typically, biologically active portions comprise a domain or motif with at least one activity of a protein, e.g., SIRT1. An exemplary domain is the SIRT1 core catalytic domain. A biologically active portion/functional domain of a protein can be a polypeptide which is, for example, 10, 25, 50, 100, 200 or more amino acids in length. Biologically active portions/functional domain of a protein can be used as targets for developing agents which modulate SIRT1.

The following are exemplary SIR sequences:

```
>sp|Q96EB6|SIR1_HUMAN NAD-dependent deacetylase sirtuin 1
(EC 3.5.1.-) (hSIRT1) (hSIR2) (SIR2-like protein 1)-Homo
sapiens (Human).
                                             (SEQ ID NO: 1)
MADEAALALQPGGSPSAAGADREAASSPAGEPLRKRPRRDGPGLERSPGEPGGAAPEREV

PAAARGCPGAAAAALWREAEAEAAAAGGEQEAQATAAAGEGDNGPGLQGPSREPPLADNL

YDEDDDDEGEEEEEAAAAAIGYRDNLLFGDEIITNGFHSCESDEEDRASHASSSDWTPRP

RIGPYTFVQQHLMIGTDPRTILKDLLPETIPPPELDDMTLWQIVINILSEPPKRKKRKDI

NTIEDAVKLLQECKKIIVLTGAGVSVSCGIPDFRSRDGIYARLAVDFPDLPDPQAMFDIE

YFRKDPRPFFKFAKEIYPGQFQPSLCHKFIALSDKEGKLLRNYTQNIDTLEQVAGIQRII

QCHGSFATASCLICKYKVDCEAVRGDIFNQVVPRCPRCPADEPLAIMKPEIVFFGENLPE

QFHRAMKYDKDEVDLLIVIGSSLKVRPVALIPSSIPHEVPQILINREPLPHLHFDVELLG

DCDVIINELCHRLGGEYAKLCCNPVKLSEITEKPPRTQKELAYLSELPPTPLHVSEDSSS

PERTSPPDSSVIVTLLDQAAKSNDDLDVSESKGCMEEKPQEVQTSRNVESIAEQMENPDL

KNVGSSTGEKNERTSVAGTVRKCWPNRVAKEQISRRLDGNQYLFLPPNRYIFHGAEVYSD

SEDDVLSSSSCGSNSDSGTCQSPSLEEPMEDESEIEEFYNGLEDEPDVPERAGGAGFGTD

GDDQEAINEAISVKQEVTDMNYPSNKS

>sp|Q8IXJ6|SIR2_HUMAN NAD-dependent deacetylase sirtuin 2
(EC 3.5.1.-) (SIR2-like) (SIR2-like protein 2)-Homo
sapiens (Human).
                                             (SEQ ID NO: 2)
MAEPDPSHPLETQAGKVQEAQDSDSDSEGGAAGGEADMDFLRNLFSQTLSLGSQKERLLD

ELTLEGVARYMQSERCRRVICLVGAGISTSAGIPDFRSPSTGLYDNLEKYHLPYPEAIFE

ISYFKKHPEPFFALAKELYPGQFKPTICHYFMRLLKDKGLLLRCYTQNIDTLERIAGLEQ

EDLVEAHGTFYTSHCVSASCRHEYPLSWMKEKIFSEVTPKCEDCQSLVKPDIVFFGESLP
```

-continued

ARFFSCMQSDFLKVDLLLVMGTSLQVQPFASLISKAPLSTPRLLINKEKAGQSDPFLGMI

MGLGGGMDFDSKKAYRDVAWLGECDQGCLALAELLGWKKELEDLVRREHASIDAQSGAGV

PNPSTSASPKKSPPPAKDEARTTEREKPQ

>sp|Q9NTG7|SIR3_HUMAN NAD-dependent deacetylase sirtuin 3,
mitochondrial precursor (EC 3.5.1.-) (SIR2-like protein 3)
(hSIRT3)-Homo sapiens (Human).
(SEQ ID NO: 3)
MAFWGWRAAAALRLWGRVVERVEAGGGVGPFQACGCRLVLGGRDDVSAGLRGSHGARGEP

LDPARPLQRPPRPEVPRAFRRQPRAAAPSFFFSSIKGGRRSISFSVGASSVVGSGGSSDK

GKLSLQDVAELIRARACQRVVVMVGAGISTPSGIPDFRSPGSGLYSNLQQYDLPYPEAIF

ELPFFFHNPKPFFTLAKELYPGNYKPNVTHYFLRLLHDKGLLLRLYTQNIDGLERVSGIP

ASKLVEAHGTFASATCTVCQRPFPGEDIRADVMADRVPRCPVCTGVVKPDIVFFGEPLPQ

RFLLHVVDFPMADLLLILGTSLEVEPFASLTEAVRSSVPRLLINRDLVGPLAWHPRSRDV

AQLGDVVHGVESLVELLGWTEEMRDLVQRETGKLDGPDK

>sp|Q9Y6E7|SIR4_HUMAN NAD-dependent deacetylase sirtuin 4
(EC 3.5.1.-) (SIR2-like protein 4)-Homo sapiens (Human).
(SEQ ID NO: 4)
MKMSFALTFRSAKGRWIANPSQPCSKASIGLFVPASPPLDPEKVKELQRFITLSKRLLVM

TGAGISTESGIPDYRSEKVGLYARTDRRPIQHGDFVRSAPIRQRYWARNFVGWPQFSSHQ

PNPAHWALSTWEKLGKLYWLVTQNVDALHTKAGSRRLTELHGCMDRVLCLDCGEQTPRGV

LQERFQVLNPTWSAEAHGLAPDGDVFLSEEQVRSFQVPTCVQCGGHLKPDVVFFGDTVNP

DKVDFVHKRVKEADSLLVVGSSLQVYSGYRFILTAWEKKLPIAILNIGPTRSDDLACLKL

NSRCGELLPLIDPC

>sp|Q9NXA8|SIR5_HUMAN NAD-dependent deacetylase sirtuin 5
(EC 3.5.1.-) (SIR2-like protein 5)-Homo sapiens (Human).
(SEQ ID NO: 5)
MRPLQIVPSRLISQLYCGLKPPASTRNQICLKMARPSSSMADFRKFFAKAKHIVIISGAG

VSAESGVPTFRGAGGYWRKWQAQDLATPLAFAHNPSRVWEFYHYRREVMGSKEPNAGHRA

IAECETRLGKQGRRVVVITQNIDELHRKAGTKNLLEIHGSLFKTRCTSCGVVAENYKSPI

CPALSGKGAPEPGTQDASIPVEKLPRCEEAGCGGLLRPHVVWFGENLDPAILEEVDRELA

HCDLCLVVGTSSVVYPAAMFAPQVAARGVPVAEFNTETTPATNRFRFHFQGPCGTTLPEA

LACHENETVS

>sp|Q8N6T7|SIR6_HUMAN NAD-dependent deacetylase sirtuin 6
(EC 3.5.1.-) (SIR2-like protein 6)-Homo sapiens (Human).
(SEQ ID NO: 6)
MSVNYAAGLSPYADKGKCGLPEIFDPPEELERKVWELARLVWQSSSVVFHTGAGISTASG

IPDFRGPHGVWTMEERGLAPKFDTTFESARPTQTHMALVQLERVGLLRFLVSQNVDGLHV

RSGFPRDKLAELHGNMFVEECAKCKTQYVRDTVVGTMGLKATGRLCTVAKARGLRACRGE

LRDTILDWEDSLPDRDLALADEASRNADLSITLGTSLQIRPSGNLPLATKRRGGRLVIVN

LQPTKHDRHADLRIHGYVDEVMTRLMKHLGLEIPAWDGPRVLERALPPLPRPPTPKLEPK

EESPTRINGSIPAGPKQEPCAQHNGSEPASPKRERPTSPAPHRPPKRVKAKAVPS

>sp|Q9NRC8|SIR7_HUMAN NAD-dependent deacetylase sirtuin 7
(EC 3.5.1.-) (SIR2-like protein 7)-Homo sapiens (Human).
(SEQ ID NO: 7)
MAAGGLSRSERKAAERVRRLREEQQRERLRQVSRILRKAAAERSAEEGRLLAESADLVTE

LQGRSRRREGLKRRQEEVCDDPEELRGKVRELASAVRNAKYLVVYTGAGISTAASIPDYR

GPNGVWTLLQKGRSVSAADLSEAEPTLTHMSITRLHEQKLVQHVVSQNCDGLHLRSGLPR

TAISELHGNMYIEVCTSCVPNREYVRVFDVTERTALHRHQTGRTCHKCGTQLRDTIVHFG

-continued

```
ERGTLGQPLNWEAATEAASRADTILCLGSSLKVLKKYPRLWCMTKPPSRRPKLYIVNLQW

TPKDDWAALKLHGKCDDVMRLLMAELGLEIPAYSRWQDPIFSLATPLRAGEEGSHSRKSL

CRSREEAPPGDRGAPLSSAPILGGWFGRGCTKRTKRKKVT
```

Exemplary compounds described herein may inhibit activity of SIRT1 or a functional domain thereof by at least 10, 20, 25, 30, 50, 80, or 90%, with respect to a natural or artificial substrate described herein. For example, the compounds may have a Ki of less than 500, 200, 100, or 50 nM.

A compound described herein may also modulate a complex between a sirtuin and a transcription factor, e.g., increase or decrease complex formation, deformation, and/or stability. Exemplary sirtuin-TF complexes include Sir2-PCAF, SIR2-MyoD, Sir2-PCAF-MyoD, Sir2-p53, Sir2-FoxO1, and Sir2-FoxO3. A compound described herein may also modulate expression of a Sir2 regulated gene, e.g., a gene described in Table 1 of Fulco et al. (2003) *Mol. Cell.* 12:51-62.

In Vitro Assays

In some embodiments, interaction with, e.g., binding of, SIRT1 can be assayed in vitro. The reaction mixture can include a SIRT1 co-factor such as NAD and/or a NAD analog.

In other embodiments, the reaction mixture can include a SIRT1 binding partner, e.g., a transcription factor, e.g., p53 or a transcription factor other than p53 such as FoxO1 or FoxO3, and compounds can be screened, e.g., in an in vitro assay, to evaluate the ability of a test compound to modulate interaction between SIRT1 and a SIRT1 binding partner, e.g., a transcription factor. This type of assay can be accomplished, for example, by coupling one of the components, with a radioisotope or enzymatic label such that binding of the labeled component to the other can be determined by detecting the labeled compound in a complex. A component can be labeled with $^{125}$I, $^{35}$S, $^{14}$C, or $^{3}$H, either directly or indirectly, and the radioisotope detected by direct counting of radioemmission or by scintillation counting. Alternatively, a component can be enzymatically labeled with, for example, horseradish peroxidase, alkaline phosphatase, or luciferase, and the enzymatic label detected by determination of conversion of an appropriate substrate to product. Competition assays can also be used to evaluate a physical interaction between a test compound and a target.

Cell-free assays involve preparing a reaction mixture of the target protein (e.g., SIRT1) and the test compound under conditions and for a time sufficient to allow the two components to interact and bind, thus forming a complex that can be removed and/or detected.

The interaction between two molecules can also be detected, e.g., using a fluorescence assay in which at least one molecule is fluorescently labeled. One example of such an assay includes fluorescence energy transfer (FET or FRET for fluorescence resonance energy transfer) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FET binding event can be conveniently measured through standard fluorometric detection means well known in the art (e.g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP. See, e.g., Nasir et al. (1999) *Comb Chem HTS* 2:177-190; Jameson et al. (1995) *Methods Enzymol* 246:283; Seethala et al. (1998) *Anal Biochem.* 255:257. Fluorescence polarization can be monitored in multiwell plates, e.g., using the Tecan Polarion™ reader. See, e.g., Parker et al. (2000) *Journal of Biomolecular Screening* 5:77-88; and Shoeman, et al. (1999) 38, 16802-16809.

In another embodiment, determining the ability of the SIRT1 protein to bind to a target molecule can be accomplished using real-time Biomolecular Interaction Analysis (BIA) (see, e.g., Sjolander, S, and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, SIRT1 is anchored onto a solid phase. The SIRT1/test compound complexes anchored on the solid phase can be detected at the end of the reaction, e.g., the binding reaction. For example, SIRT1 can be anchored onto a solid surface, and the test compound, (which is not anchored), can be labeled, either directly or indirectly, with detectable labels discussed herein.

It may be desirable to immobilize either the SIRT1 or an anti-SIRT1 antibody to facilitate separation of complexed from uncomplexed forms of one or both of the proteins, as well as to accommodate automation of the assay. Binding of a test compound to a SIRT1 protein, or interaction of a SIRT1 protein with a second component in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/SIRT1 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or SIRT1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of SIRT1 binding or activity determined using standard techniques.

Other techniques for immobilizing either a SIRT1 protein or a target molecule on matrices include using conjugation of biotin and streptavidin. Biotinylated SIRT1 protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways.

Where the previously non-immobilized component is pre-labeled, the detection of label immobilized on the surface indicates that complexes were formed. Where the previously non-immobilized component is not pre-labeled, an indirect label can be used to detect complexes anchored on the surface, e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with a SIRT1 protein or target molecules but which do not interfere with binding of the SIRT1 protein to its target molecule. Such antibodies can be derivatized to the wells of the plate, and unbound target or the SIRT1 protein trapped in the wells by antibody conjugation. Methods for detecting such complexes, in addition to those described above for the GST-immobilized complexes, include immunodetection of complexes using antibodies reactive with the SIRT1 protein or target molecule, as well as enzyme-linked assays which rely on detecting an enzymatic activity associated with the SIRT1 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the SIRT1 protein or biologically active portion thereof with a known compound which binds a SIRT1 to form an assay mixture, contacting the assay mixture with a test compound, and determining the ability of the test compound to interact with a SIRT1 protein, wherein determining the ability of the test compound to interact with the SIRT1 protein includes determining the ability of the test compound to preferentially bind to the SIRT1 or biologically active portion thereof, or to modulate the activity of a target molecule, as compared to the known compound.

An exemplary assay method includes a 1536 well format of the SirT1 enzymatic assay that is based on the commercial "Fluor-de-Lys" assay principle by Biomol, which is fluorogenic (www.biomol.com/store/Product_Data_PDFs/ak500.pdf). In this assay, deacetylation of the e-amino function of a lysyl residue is coupled to a fluorogenic "development step that is dependent on the unblocked e-amino functionality and generates fluorescent aminomethylcoumarin. Fluorescence can be read on a commercial macroscopic reader.

Additional Assays

A compound or library of compounds described herein can also be evaluated using one of the following model systems for a disease or disorder, or other known models of a disease or disorder described herein.

Models for evaluating the effect of a test compound on muscle atrophy include, e.g., 1) rat medial gastrocnemius muscle mass loss resulting from denervation, e.g., by severing the right sciatic nerve at mid-thigh; 2) rat medial gastrocnemius muscle mass loss resulting from immobilization, e.g., by fixed the right ankle joint at 90 degrees of flexion; 3) rat medial gastrocnemius muscle mass loss resulting from hind-limb suspension; (see, e.g., U.S. 2003-0129686); 4) skeletal muscle atrophy resulting from treatment with the cachectic cytokine, interleukin-1 (IL-1) (R. N. Cooney, S. R. Kimball, T. C. Vary, Shock 7, 1-16 (1997)); and 5) skeletal muscle atrophy resulting from treatment with the glucocorticoid, dexamethasone (A. L. Goldberg, J Biol Chem 244, 3223-9 (1969)). Models 1, 2, and 3 induce muscle atrophy by altering the neural activity and/or external load a muscle experiences to various degrees. Models 4 and 5 induce atrophy without directly affecting those parameters MS (experimental autoimmune encephalomyelitis (EAE)), e.g., as described by Goverman et al., Cell. 72:551-60 (1993), and primate models as reviewed by Brok et al., Immunol. Rev., 183:173-85 (2001).

Exemplary animal models for AMD (age-related macular degeneration) include: laser-induced mouse model simulating exudative (wet) macular degeneration Bora et al., Proc. Natl. Acad. Sci. USA., 100:2679-84 (2003); a transgenic mouse expressing a mutated form of cathepsin D resulting in features associated with the "geographic atrophy" form of AMD (Rakoczy et al., Am. J. Pathol., 161:1515-24 (2002)); and a transgenic mouse overexpressing VEGF in the retinal pigment epithelium resulting in CNV. Schwesinger et al., Am. J. Pathol. 158:1161-72 (2001).

Exemplary animal models of Parkinson's disease include primates rendered parkinsonian by treatment with the dopaminergic neurotoxin 1-methyl-4 phenyl 1,2,3,6-tetrahydropyridine (MPTP) (see, e.g., US Appl 20030055231 and Wichmann et al., Ann. N.Y. Acad. Sci., 991:199-213 (2003); 6-hydroxydopamine-lesioned rats (e.g., Lab. Anim. Sci., 49:363-71 (1999)); and transgenic invertebrate models (e.g., Lakso et al., J. Neurochem., 86:165-72 (2003) and Link, Mech. Ageing Dev., 122:1639-49 (2001)).

Exemplary molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., Diabetes, 50:1126-33 (2001); and a transgenic mouse with a dominant-negative IGF-I receptor (KR-IGF-IR) having Type 2 diabetes-like insulin resistance.

Exemplary animal and cellular models for neuropathy include: vincristine induced sensory-motor neuropathy in mice (US Appl 5420112) or rabbits (Ogawa et al., Neurotoxicology, 21:501-11 (2000)); a streptozotocin (STZ)-diabetic rat for study of autonomic neuropathy (Schmidt et al., Am. J. Pathol., 163:21-8 (2003)); and a progressive motor neuropathy (pmn) mouse (Martin et al., Genomics, 75:9-16 (2001)).

Structure-Activity Relationships and Structure-Based Design. It is also possible to use structure-activity relationships (SAR) and structure-based design principles to produce a compound that interact with a sirtuin, e.g., antagonizes or agonizes a sirtuin. SARs provide information about the activity of related compounds in at least one relevant assay. Correlations are made between structural features of a compound of interest and an activity. For example, it may be possible by evaluating SARs for a family of compounds related to a compound described herein to identify one or more structural features required for the agonist's activity. A library of compounds can then be chemically produced that vary these features. In another example, a single compound that is predicted to interact is produced and evaluated in vitro or in vivo.

Structure-based design can include determining a structural model of the physical interaction of a functional domain of a sirtuin and a compound. The structural model can indicate how the compound can be engineered, e.g., to improve interaction or reduce unfavorable interactions. The compound's interaction with the sirtuin can be identified, e.g., by solution of a crystal structure, NMR, or computer-based modeling, e.g., docking methods. See, e.g., Ewing et al. J Comput Aided Mol. Des. 2001 May; 15(5):411-28.

Both the SAR and the structure-based design approach, as well as other methods, can be used to identify a pharmacophore. A pharmacophore is defined as a distinct three dimensional (3D) arrangement of chemical groups. The selection of such groups may be favorable for biological activity. Since a pharmaceutically active molecule must interact with one or more molecular structures within the body of the subject in order to be effective, and the desired functional properties of the molecule are derived from these interactions, each active compound must contain a distinct arrangement of chemical groups which enable this interaction to occur. The chemical groups, commonly termed descriptor centers, can be represented by (a) an atom or group of atoms; (b) pseudo-atoms, for example a center of a ring, or the center of mass of a molecule; (c) vectors, for example atomic pairs, electron lone pair directions, or the normal to a plane. Once formulated a pharmacophore can be used to search a database of chemical compound, e.g., for those having a structure compatible with the pharmacophore. See, for example, U.S. Pat. No. 6,343, 257; Y. C. Martin, 3D Database Searching in Drug Design, J. Med. Chem. 35, 2145 (1992); and A. C. Good and J. S. Mason, Three Dimensional Structure Database Searches, Reviews in Comp. Chem. 7, 67 (1996). Database search queries are based not only on chemical property information but also on precise geometric information.

Computer-based approaches can use database searching to find matching templates; Y C. Martin, Database searching in drug design, J. Medicinal Chemistry, vol. 35, pp 2145-54 (1992), which is herein incorporated by reference. Existing methods for searching 2-D and 3-D databases of compounds are applicable. Lederle of American Cyanamid (Pearl River, N.Y.) has pioneered molecular shape-searching, 3D searching and trend-vectors of databases. Commercial vendors and other research groups also provide searching capabilities (MACSS-3D, Molecular Design Ltd. (San Leandro, Calif.); CAVEAT, Lauri, G. et al., University of California (Berkeley, Calif.); CHEM-X, Chemical Design, Inc. (Mahwah, N.J.)).

Software for these searches can be used to analyze databases of potential drug compounds indexed by their significant chemical and geometric structure (e.g., the Standard Drugs File (Derwent Publications Ltd., London, England), the Bielstein database (Bielstein Information, Frankfurt, Germany or Chicago), and the Chemical Registry database (CAS, Columbus, Ohio)).

Once a compound is identified that matches the pharmocophore, it can be tested for activity in vitro, in vivo, or in silico, e.g., for binding to a sirtuin or domain thereof.

In one embodiment, a compound that is an agonist or a candidate agonist, e.g., a compound described in Nature. 2003 Sep. 11; 425(6954):191-196 can be modified to identify an antagonist, e.g., using the method described herein. For example, a library of related compounds can be prepared and the library can be screened in an assay described herein.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The compositions delineated herein include the compounds of the formulae delineated herein, as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing) on the adhesive or device.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Neoplastic Disorders

The compounds of the invention can be used in the treatment of cancer. As used herein, the terms "cancer", "hyperproliferative", "malignant", and "neoplastic" are used interchangeably, and refer to those cells an abnormal state or condition characterized by rapid proliferation or neoplasm. The terms include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be benign, premalignant or malignant.

Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, prostate, ovary as well as adenocarcinomas which include malignancies such as most colon cancers, rectal cancer, renal-cell carcinoma, liver cancer, non-small cell carcinoma of the lung, cancer of the small intestine and so forth. Metastatic lesions of the aforementioned cancers can also be treated or prevented using a compound described herein.

The subject method can be useful in treating malignancies of the various organ systems, such as those affecting lung, breast, lymphoid, gastrointestinal (e.g., colon), and genitourinary tract, prostate, ovary, pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. Exemplary solid tumors that can be treated include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

The subject method can also be used to inhibit the proliferation of hyperplastic/neoplastic cells of hematopoietic origin, e.g., arising from myeloid, lymphoid or erythroid lineages, or precursor cells thereof. For instance, the invention contemplates the treatment of various myeloid disorders including, but not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97). Lymphoid malignancies which may be treated by the subject method include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

Alzheimer's Disease

Alzheimer's Disease (AD) is a complex neurodegenerative disease that results in the irreversible loss of neurons and is an example of a neurodegenerative disease that has symptoms caused at least in part by protein aggregation. A compound described herein can be used to ameliorate at least one symptom of a subject that has AD.

Clinical hallmarks of Alzheimer's Disease include progressive impairment in memory, judgment, orientation to physical surroundings, and language.

Neuropathological hallmarks of AD include region-specific neuronal loss, amyloid plaques, and neurofibrillary tangles. Amyloid plaques are extracellular plaques containing the β amyloid peptide (also known as Aβ, or Aβ42), which is a cleavage product of the β-amyloid precursor protein (also known as APP). Neurofibrillary tangles are insoluble intracellular aggregates composed of filaments of the abnormally hyperphosphorylated microtubule-associated protein, tau. Amyloid plaques and neurofibrillary tangles may contribute to secondary events that lead to neuronal loss by apoptosis (Clark and Karlawish, Ann. Intern. Med. 138(5):400-410 (2003). For example, β-amyloid induces caspase-2-dependent apoptosis in cultured neurons (Troy et al. J. Neurosci. 20(4):1386-1392). The deposition of plaques in vivo may trigger apoptosis of proximal neurons in a similar manner.

Mutations in genes encoding APP, presenilin-1, and presenilin-2 have been implicated in early-onset AD (Lendon et al. JAMA 227:825 (1997)). Mutations in these proteins have been shown to enhance proteolytic processing of APP via an intracellular pathway that produces Aβ. Aberrant regulation of Aβ processing may be central to the formation of amyloid plaques and the consequent neuronal damage associated with plaques.

A variety of criteria, including genetic, biochemical, physiological, and cognitive criteria, can be used to evaluate AD in a subject. Symptoms and diagnosis of AD are known to medical practitioners. Some exemplary symptoms and markers of AD are presented below. Information about these indications and other indications known to be associated with AD can be used as an "AD-related parameter." An AD-related parameter can include qualitative or quantitative information. An example of quantitative information is a numerical value of one or more dimensions, e.g., a concentration of a protein or a tomographic map. Qualitative information can include an assessment, e.g., a physician's comments or a binary ("yes"/"no") and so forth. An AD-related parameter includes information that indicates that the subject is not diagnosed with AD or does not have a particular indication of AD, e.g., a cognitive test result that is not typical of AD or a genetic APOE polymorphism not associated with AD.

Progressive cognitive impairment is a hallmark of AD. This impairment can present as decline in memory, judgment, decision making, orientation to physical surroundings, and language (Nussbaum and Ellis, New Eng. J. Med. 348(14): 1356-1364 (2003)). Exclusion of other forms of dementia can assist in making a diagnosis of AD.

Neuronal death leads to progressive cerebral atrophy in AD patients. Imaging techniques (e.g., magnetic resonance imaging, or computed tomography) can be used to detect AD-associated lesions in the brain and/or brain atrophy.

AD patients may exhibit biochemical abnormalities that result from the pathology of the disease. For example, levels of tau protein in the cerebrospinal fluid is elevated in AD patients (Andreasen, N. et al. Arch Neurol. 58:349-350 (2001)). Levels of amyloid beta 42 (Aβ42) peptide can be reduced in CSF of AD patients (Galasko, D., et al. Arch. Neurol. 55:937-945 (1998)). Levels of Aβ42 can be increased in the plasma of AD patients (Ertekein-Taner, N., et al. Science 290:2303-2304 (2000)). Techniques to detect biochemical abnormalities in a sample from a subject include cellular, immunological, and other biological methods known in the art. For general guidance, see, e.g., techniques described in Sambrook & Russell, Molecular Cloning: A Laboratory Manual, 3$^{rd}$ Edition, Cold Spring Harbor Laboratory, N.Y. (2001), Ausubel et al., Current Protocols in Molecular Biology (Greene Publishing Associates and Wiley Interscience, N.Y. (1989), (Harlow, E. and Lane, D. (1988) Antibodies: A Laboratory Manual, Cold Spring Harbor Laboratory Press, Cold Spring Harbor, N.Y.), and updated editions thereof.

For example, antibodies, other immunoglobulins, and other specific binding ligands can be used to detect a biomolecule, e.g., a protein or other antigen associated with AD. For example, one or more specific antibodies can be used to probe a sample. Various formats are possible, e.g., ELISAs, fluorescence-based assays, Western blots, and protein arrays. Methods of producing polypeptide arrays are described in the art, e.g., in De Wildt et al. (2000). Nature Biotech. 18, 989-994; Lueking et al. (1999). Anal. Biochem. 270, 103-111; Ge, H. (2000). Nucleic Acids Res. 28, e3, I-VII; MacBeath, G., and Schreiber, S. L. (2000). Science 289, 1760-1763; and WO 99/51773A1. Proteins can also be analyzed using mass spectroscopy, chromatography, electrophoresis, enzyme interaction or using probes that detect post-translational modification (e.g., a phosphorylation, ubiquitination, glycosylation, methylation, or acetylation).

Nucleic acid expression can be detected in cells from a subject, e.g., removed by surgery, extraction, post-mortem or other sampling (e.g., blood, CSF). Expression of one or more genes can be evaluated, e.g., by hybridization based techniques, e.g., Northern analysis, RT-PCR, SAGE, and nucleic acid arrays. Nucleic acid arrays are useful for profiling multiple mRNA species in a sample. A nucleic acid array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

Metabolites that are associated with AD can be detected by a variety of means, including enzyme-coupled assays, using labeled precursors, and nuclear magnetic resonance (NMR). For example, NMR can be used to determine the relative concentrations of phosphate-based compounds in a sample, e.g., creatine levels. Other metabolic parameters such as redox state, ion concentration (e.g., $Ca^{2+}$)(e.g., using ion-sensitive dyes), and membrane potential can also be detected (e.g., using patch-clamp technology).

Information about an AD-associated marker can be recorded and/or stored in a computer-readable format. Typically the information is linked to a reference about the subject and also is associated (directly or indirectly) with information about the identity of one or more nucleotides in a gene that encodes a sirtuin in the subject.

In one embodiment, a non-human animal model of AD (e.g., a mouse model) is used, e.g., to evaluate a compound or a therapeutic regimen, e.g., of a compound described herein. For example, U.S. Pat. No. 6,509,515 describes one such model animal which is naturally able to be used with learning and memory tests. The animal expresses an amyloid precursor protein (APP) sequence at a level in brain tissues such that the animal develops a progressive neurologic disorder within a short period of time from birth, generally within a year from birth, preferably within 2 to 6 months, from birth. The APP protein sequence is introduced into the animal, or an ancestor of the animal, at an embryonic stage, preferably the one cell, or fertilized oocyte, stage, and generally not later than about the 8-cell stage. The zygote or embryo is then developed to term in a pseudo-pregnant foster female. The amyloid precursor protein genes are introduced into an animal embryo so as to be chromosomally incorporated in a state which results in super-endogenous expression of the amyloid precursor protein and the development of a progressive neurologic disease in the cortico-limbic areas of the brain, areas of the brain which are prominently affected in progressive neurologic disease states such as AD. The gliosis and clinical manifestations in affected transgenic animals model neurologic disease. The progressive aspects of the neurologic disease are characterized by diminished exploratory and/or locomotor behavior and diminished 2-deoxyglucose uptake/utilization and hypertrophic gliosis in the cortico-limbic regions of the brain. Further, the changes that are seen are similar to those that are seen in some aging animals. Other animal models are also described in U.S. Pat. Nos. 5,387,742; 5,877,399; 6,358,752; and 6,187,992.

Parkinson's Disease

Parkinson's disease includes neurodegeneration of dopaminergic neurons in the substantia nigra resulting in the degeneration of the nigrostriatal dopamine system that regulates motor function. This pathology, in turn, leads to motor dysfunctions. (see, e.g., and Lotharius et al., Nat. Rev. Neurosci., 3:932-42 (2002).) Exemplary motor symptoms include: akinesia, stooped posture, gait difficulty, postural instability, catalepsy, muscle rigidity, and tremor. Exemplary non-motor symptoms include: depression, lack of motivation, passivity, dementia and gastrointestinal dysfunction (see, e.g., Fahn, Ann. N.Y. Acad. Sci., 991:1-14 (2003) and Pfeiffer, Lancet Neurol., 2:107-16 (2003)) Parkinson's has been observed in 0.5 to 1 percent of persons 65 to 69 years of age and 1 to 3 percent among persons 80 years of age and older. (see, e.g., Nussbaum et al., N. Engl. J. Med., 348:1356-64 (2003)).

A compound described herein can be used to ameliorate at least one symptom of a subject that has Parkinson's disease.

Molecular markers of Parkinson's disease include reduction in aromatic L-amino acid decarboxylase (AADC). (see, e.g., US Appl 20020172664); loss of dopamine content in the nigrostriatal neurons (see, e.g., Fahn, Ann. N.Y. Acad. Sci., 991:1-14 (2003) and Lotharius et al., Nat. Rev. Neurosci., 3:932-42 (2002)). In some familial cases, PD is linked to mutations in single genes encoding alpha-synuclein and parkin (an E3 ubiquitin ligase) proteins. (e.g., Riess et al., J. Neurol. 250 Suppl 1:I3-10 (2003) and Nussbaum et al., N. Engl. J. Med., 348:1356-64 (2003)). A missense mutation in a neuron-specific C-terminal ubiquitin hydrolase gene is also associated with Parkinson's. (e.g., Nussbaum et al., N. Engl. J. Med., 348:1356-64 (2003))

A compound or library of compounds described herein can be evaluated in a non-human animal model of Parkinson's disease. Exemplary animal models of Parkinson's disease include primates rendered parkinsonian by treatment with the dopaminergic neurotoxin 1-methyl-4 phenyl 1,2,3,6-tetrahydropyridine (MPTP) (see, e.g., US Appl 20030055231 and Wichmann et al., Ann. N.Y. Acad. Sci., 991:199-213 (2003); 6-hydroxydopamine-lesioned rats (e.g., Lab. Anim. Sci., 49:363-71 (1999)); and transgenic invertebrate models (e.g., Lakso et al., J. Neurochem., 86:165-72 (2003) and Link, Mech. Ageing Dev., 122:1639-49 (2001)).

Evaluating Polyglutamine Aggregation

A variety of cell free assays, cell based assays, and organismal assays are available for evaluating polyglutamine aggregation, e.g., Huntingtin polyglutamine aggregation. Some examples are described, e.g., in U.S. 2003-0109476.

Assays (e.g., cell free, cell-based, or organismal) can include a reporter protein that includes a polyglutamine repeat region which has at least 35 polyglutamines. The reporter protein can be easily detectable, e.g., by fluorescence. For example, the protein is conjugated to a fluorophore, for example, fluorescein isothiocyanate (FITC), allophycocyanin (APC), R-phycoerythrin (PE), peridinin chlorophyll protein (PerCP), Texas Red, Cy3, Cy5, Cy7, or a fluorescence resonance energy tandem fluorophore such as PerCP-Cy5.5, PE-Cy5, PE-Cy5.5, PE-Cy7, PE-Texas Red, and APC-Cy7. In another example the protein is "intrinsically fluorescent" in that it has a chromophore is entirely encoded by its amino acid sequence and can fluoresce without requirement for cofactor or substrate. For example, the protein can include a green fluorescent protein (GFP)-like chromophore. As used herein, "GFP-like chromophore" means an intrinsically fluorescent protein moiety comprising an 11-stranded β-barrel with a central α-helix, the central α-helix having a conjugated π-resonance system that includes two aromatic ring systems and the bridge between them.

The GFP-like chromophore can be selected from GFP-like chromophores found in naturally occurring proteins, such as *A. victoria* GFP (GenBank accession number AAA27721), *Renilla reniformis* GFP, FP583 (GenBank accession no. AF168419) (DsRed), FP593 (AF272711), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are known in the art. Li et al., J. Biol. Chem. 272:28545-28549 (1997).

Alternatively, the GFP-like chromophore can be selected from GFP-like chromophores modified from those found in nature. Typically, such modifications are made to improve recombinant production in heterologous expression systems (with or without change in protein sequence), to alter the excitation and/or emission spectra of the native protein, to facilitate purification, to facilitate or as a consequence of cloning, or are a fortuitous consequence of research investigation. The methods for engineering such modified GFP-like chromophores and testing them for fluorescence activity, both alone and as part of protein fusions, are well-known in the art.

A variety of such modified chromophores are now commercially available and can readily be used in the fusion proteins of the present invention. For example, EGFP ("enhanced GFP"), Cormack et al., Gene 173:33-38 (1996); U.S. Pat. Nos. 6,090,919 and 5,804,387, is a red-shifted, human codon-optimized variant of GFP that has been engineered for brighter fluorescence, higher expression in mammalian cells, and for an excitation spectrum optimized for use in flow cytometers. EGFP can usefully contribute a GFP-like chromophore to the fusion proteins that further include a polyglutamine region. A variety of EGFP vectors, both plasmid and viral, are available commercially (Clontech Labs, Palo Alto, Calif., USA). Still other engineered GFP proteins are known. See, e.g., Heim et al., Curr. Biol. 6:178-182 (1996); Cormack et al., Gene 173:33-38 (1996), BFP2, EYFP ("enhanced yellow fluorescent protein"), EBFP, Ormo et al., Science 273:1392-1395 (1996), Heikal et al., Proc. Natl. Acad. Sci. USA 97:11996-12001 (2000). ECFP ("enhanced cyan fluorescent protein") (Clontech Labs, Palo Alto, Calif., USA). The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048.

In one embodiment, a reporter protein that includes a polyglutamine repeat region which has at least 35 polyglutamines is used in a cell-based assay.

In one example, PC12 neuronal cell lines that have a construct engineered to express a protein encoded by HD gene exon 1 containing alternating, repeating codons fused to an enhanced GFP (green fluorescent protein) gene can be used. See, e.g., Boado et al. J. Pharmacol. and Experimental Therapeutics 295(1): 239-243 (2000) and Kazantsev et al. Proc. Natl. Acad. Sci. USA 96: 11404-09 (1999). Expression of this gene leads to the appearance of green fluorescence co-localized to the site of protein aggregates. The HD gene exon 1-GFP fusion gene is under the control of an inducible promoter regulated by muristerone. A particular construct has approximately 46 glutamine repeats (encoded by either CAA or CAG). Other constructs have, for example, 103 glutamine repeats. PC12 cells are grown in DMEM, 5% Horse serum (heat inactivated), 2.5% FBS and 1% Pen-Strep, and maintained in low amounts on Zeocin and G418. The cells are plated in 24-well plates coated with poly-L-lysine coverslips, at a density of $5 \cdot 10^5$ cells/ml in media without any selection. Muristerone is added after the overnight incubation to induce the expression of HD gene exon 1-GFP. The cells can be contacted with a test compound, e.g., before or after plating and before or after induction. The data can be acquired on a Zeiss inverted 100M Axioskop equipped with a Zeiss 510 LSM confocal microscope and a Coherent Krypton Argon laser and a Helium Neon laser. Samples can be loaded into Lab-Tek II chambered coverglass system for improved imaging. The number of Huntingtin-GFP aggregations within the field of view of the objective is counted in independent experiments (e.g., at least three or seven independent experiments).

Other exemplary means for evaluating samples include a high throughput apparatus, such as the Amersham Biosciences IN Cell Analysis System and Cellomics™ ArrayScan HCS System which permit the subcellular location and concentration of fluorescently tagged moieties to be detected and quantified, both statically and kinetically. See also, U.S. Pat. No. 5,989,835.

Other exemplary mammalian cell lines include: a CHO cell line and a 293 cell line. For example, CHO cells with integrated copies of HD gene exon 1 with approximately 103Q repeats fused to GFP as a fusion construct encoding HD gene exon 1 Q103-GFP produce a visible GFP aggregation at the nuclear membrane, detectable by microscopy, whereas CHO cells with integrated copies of fusion constructs encoding HD gene exon 1 Q24-GFP in CHO cells do not produce a visible GFP aggregation at the nuclear membrane. In another example, 293 cells with integrated copies of the HD gene exon 1 containing 84 CAG repeats are used.

A number of animal model system for Huntington's disease are available. See, e.g., Brouillet, Functional Neurology 15(4): 239-251 (2000); Ona et al. Nature 399: 263-267 (1999), Bates et al. Hum Mol. Genet. 6(10):1633-7 (1997); Hansson et al. J. of Neurochemistry 78: 694-703; and Rubinsztein, D.C., Trends in Genetics, Vol. 18, No. 4, pp. 202-209 (a review on various animal and non-human models of HD).

In one embodiment, the animal is a transgenic mouse that can express (in at least one cell) a human Huntingtin protein, a portion thereof, or fusion protein comprising human Huntingtin protein, or a portion thereof, with, for example, at least 36 glutamines (e.g., encoded by CAG repeats (alternatively, any number of the CAG repeats may be CAA) in the CAG repeat segment of exon 1 encoding the polyglutamine tract).

An example of such a transgenic mouse strain is the R6/2 line (Mangiarini et al. Cell 87: 493-506 (1996)). The R6/2 mice are transgenic Huntington's disease mice, which overexpress exon one of the human HD gene (under the control of the endogenous promoter). The exon 1 of the R6/2 human HD gene has an expanded CAG/polyglutamine repeat lengths (150 CAG repeats on average). These mice develop a progressive, ultimately fatal neurological disease with many features of human Huntington's disease. Abnormal aggregates, constituted in part by the N-terminal part of Huntingtin (encoded by HD exon 1), are observed in R6/2 mice, both in the cytoplasm and nuclei of cells (Davies et al. Cell 90: 537-548 (1997)). For example, the human Huntingtin protein in the transgenic animal is encoded by a gene that includes at least 55 CAG repeats and more preferably about 150 CAG repeats.

These transgenic animals can develop a Huntington's disease-like phenotype.

These transgenic mice are characterized by reduced weight gain, reduced lifespan and motor impairment characterized by abnormal gait, resting tremor, hindlimb clasping and hyperactivity from 8 to 10 weeks after birth (for example the R6/2 strain; see Mangiarini et al. Cell 87: 493-506 (1996)). The phenotype worsens progressively toward hypokinesia. The brains of these transgenic mice also demonstrate neurochemical and histological abnormalities, such as changes in neurotransmitter receptors (glutamate, dopaminergic), decreased concentration of N-acetylaspartate (a marker of neuronal integrity) and reduced striatum and brain size. Accordingly, evaluating can include assessing parameters related to neurotransmitter levels, neurotransmitter receptor levels, brain size and striatum size. In addition, abnormal aggregates containing the transgenic part of or full-length human Huntingtin protein are present in the brain tissue of these animals (e.g., the R6/2 transgenic mouse strain). See, e.g., Mangiarini et al. Cell 87: 493-506 (1996), Davies et al. Cell 90: 537-548 (1997), Brouillet, Functional Neurology 15(4): 239-251 (2000) and Cha et al. Proc. Natl. Acad. Sci. USA 95: 6480-6485 (1998).

To test the effect of the test compound, e.g., a compound described herein or present in a library described herein, in an animal model, different concentrations of test compound are administered to the transgenic animal, for example by injecting the test compound into circulation of the animal. In one embodiment, a Huntington's disease-like symptom is evaluated in the animal. For example, the progression of the Huntington's disease-like symptoms, e.g. as described above for the mouse model, is then monitored to determine whether treatment with the test compound results in reduction or delay of symptoms. In another embodiment, disaggregation of the Huntingtin protein aggregates in these animals is monitored. The animal can then be sacrificed and brain slices are obtained. The brain slices are then analyzed for the presence of aggregates containing the transgenic human Huntingtin protein, a portion thereof, or a fusion protein comprising human Huntingtin protein, or a portion thereof. This analysis can includes, for example, staining the slices of brain tissue with anti-Huntingtin antibody and adding a secondary antibody conjugated with FITC which recognizes the anti-Huntingtin's antibody (for example, the anti-Huntingtin antibody is mouse anti-human antibody and the secondary antibody is specific for human antibody) and visualizing the protein aggregates by fluorescent microscopy. Alternatively, the anti-Huntingtin antibody can be directly conjugated with FITC. The levels of Huntingtin's protein aggregates are then visualized by fluorescent microscopy.

A *Drosophila melanogaster* model system for Huntington's disease is also available. See, e.g., Steffan et al., Nature, 413: 739-743 (2001) and Marsh et al., Human Molecular Genetics 9: 13-25 (2000). For example, a transgenic *Drosophila* can be engineered to express human Huntingtin protein, a portion thereof (such as exon 1), or fusion protein comprising human Huntingtin protein, or a portion thereof, with, for example, a polyglutamine region that includes at least 36 glutamines (e.g., encoded by CAG repeats (preferably 51 repeats or more) (alternatively, any number of the CAG repeats may be CAA)) The polyglutamine region can be encoded by the CAG repeat segment of exon 1 encoding the poly Q tract. These transgenic flies can also engineered to express human Huntingtin protein, a portion thereof (such as exon 1), or fusion protein comprising human Huntingtin protein, or a portion thereof, in neurons, e.g., in the *Drosophila* eye.

The test compound (e.g., different concentrations of the test compound) or a compound described herein can be administered to the transgenic *Drosophila*, for example, by applying the pharmaceutical compositions that include the compound into to the animal or feeding the compound as part of food. Administration of the compound can occur at various stages of the *Drosophila* life cycle. The animal can be monitored to determine whether treatment with the compound results in reduction or delay of Huntington's disease-like symptoms, disaggregation of the Huntingtin protein aggregates, or reduced lethality and/or degeneration of photoreceptor neurons are monitored.

Neurodegeneration due to expression of human Huntingtin protein, a portion thereof (such as exon 1), or fusion protein comprising human Huntingtin protein, or a portion thereof, is readily observed in the fly compound eye, which is composed of a regular trapezoidal arrangement of seven visible rhabdomeres (subcellular light-gathering structures) produced by the photoreceptor neurons of each *Drosophila ommatidium*. Expression of human Huntingtin protein, a portion thereof (such as exon 1), or fusion protein comprising human Huntingtin protein, or a portion thereof, leads to a progressive loss of rhabdomeres. Thus, an animal to which a test compound is administered can be evaluated for neuronal degeneration.

Morely et al. (2002) Proc. Nat. Acad. USA Vol. 99:10417 describes a *C. elegans* system for evaluating Huntington's disease related protein aggregation.

Evaluating Huntington's Disease

A compound described herein can be used to ameliorate at least one symptom of Huntington's disease in a subject.

A variety of methods are available to evaluate and/or monitor Huntington's disease. A variety of clinical symptoms and indicia for the disease are known. Huntington's disease causes a movement disorder, psychiatric difficulties and cognitive changes. The degree, age of onset, and manifestation of these symptoms can vary. The movement disorder can include quick, random, dance-like movements called chorea.

One method for evaluating Huntington's disease uses the Unified Huntington's disease Rating Scale (UNDRS). It is also possible to use individual tests alone or in combination to evaluate if at least one symptom of Huntington's disease is ameliorated. The UNDRS is described in *Movement Disorders* (vol. 11:136-142, 1996) and Marder et al. Neurology (54:452-458, 2000). The UNDRS quantifies the severity of Huntington's Disease. It is divided into multiple subsections: motor, cognitive, behavioral, functional. In one embodiment, a single subsection is used to evaluate a subject. These scores can be calculated by summing the various questions of each section. Some sections (such as chorea and dystonia) can include grading each extremity, face, bucco-oral-ligual, and trunk separately.

Exemplary motor evaluations include: ocular pursuit, saccade initiation, saccade velocity, dysarthria, tongue protrusion, finger tap ability, pronate/supinate, a first-hand-palm sequence, rigidity of arms, bradykinesia, maximal dystonia (trunk, upper and lower extremities), maximal chorea (e.g., trunk, face, upper and lower extremities), gait, tandem walking, and retropulsion. An exemplary treatment can cause a change in the Total Motor Score 4 (TMS-4), a subscale of the UHDRS, e.g., over a one-year period.

Diabetes

The invention provides methods of treating and preventing diabetes. Examples of diabetes include insulin dependent diabetes mellitus and non-insulin dependent diabetes. For example the method includes administering to a patient having diabetes or at risk of diabetes a compound described herein. In some instances, a patient can be identified as being at risk of developing diabetes by having impaired glucose tolerance (IGT), or fasting hyperglycemia.

For example, a compound described herein can be administered to a subject in a therapeutically effective amount to decrease gluconeogenesis, improve glycemic control (i.e., lower fasting blood glucose), or normalize insulin sensitivity. The compound can be administered to a subject suffering from diabetes or obesity.

Insulin dependent diabetes mellitus (Type 1 diabetes) is an autoimmune disease, where insulitis leads to the destruction of pancreatic J-cells. At the time of clinical onset of type 1 diabetes mellitus, significant number of insulin producing b cells are destroyed and only 15% to 40% are still capable of insulin production (McCulloch et al. (1991) Diabetes 40:673-679). b-cell failure results in a life long dependence on daily insulin injections and exposure to the acute and late complication of the disease.

Type 2 diabetes mellitus is a metabolic disease of impaired glucose homeostasis characterized by hyperglycemia, or high blood sugar, as a result of defective insulin action which manifests as insulin resistance, defective insulin secretion, or both. A patient with Type 2 diabetes mellitus has abnormal carbohydrate, lipid, and protein metabolism associated with insulin resistance and/or impaired insulin secretion. The disease leads to pancreatic beta cell destruction and eventually absolute insulin deficiency. Without insulin, high glucose levels remain in the blood. The long term effects of high blood glucose include blindness, renal failure, and poor blood circulation to these areas, which can lead to foot and ankle amputations. Early detection is critical in preventing patients from reaching this severity. The majority of patients with diabetes have the non-insulin dependent form of diabetes, currently referred to as Type 2 diabetes mellitus.

The invention also includes methods of treating disorders related to or resulting from diabetes, for example end organ damage, diabetic gastroparesis, diabetic neuropathy, cardiac dysrythmia, etc.

Exemplary molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., Diabetes, 50:1126-33 (2001); and a transgenic mouse with a dominant-negative IGF-I receptor (KR-IGF-IR) having Type 2 diabetes-like insulin resistance.

Metabolic Syndrome

The invention provides a method of treating metabolic syndrome, including administering to a subject an effective amount of a compound described herein.

The metabolic syndrome (e.g., Syndrome X) is characterized by a group of metabolic risk factors in one person. They include: central obesity (excessive fat tissue in and around the abdomen), atherogenic dyslipidemia (blood fat disorders—mainly high triglycerides and low HDL cholesterol—that foster plaque buildups in artery walls); insulin resistance or glucose intolerance (the body can't properly use insulin or blood sugar); prothrombotic state (e.g., high fibrinogen or plasminogen activator inhibitor [–1] in the blood); raised blood pressure (i.e., hypertension) (130/85 mmHg or higher); and proinflammatory state (e.g., elevated high-sensitivity C-reactive protein in the blood).

The underlying causes of this syndrome are overweight/obesity, physical inactivity and genetic factors. People with metabolic syndrome are at increased risk of coronary heart disease, other diseases related to plaque buildups in artery walls (e.g., stroke and peripheral vascular disease) and type 2 diabetes. Metabolic syndrome is closely associated with a generalized metabolic disorder called insulin resistance, in which the body can't use insulin efficiently.

Fat-Cell Related Disorders

The invention provides a method of enhancing adipogenesis comprising administering to a subject a compound described herein. For example, the subject can be underweight, have reduced fat content, or require additional fat cells, either locally (e.g., at a topical location such as the skin of the face) or systemically The compounds may also be used to modulate a fat cell, e.g., an adipocyte, e.g., differentiation of the adipocyte. For example, a compound described herein can be administered in an amount effective to prevent fat accumulation in a normal or a pathological state. Disorders relating to adipocytes include obesity. "Obesity" refers to a condition in which a subject has a body mass index of greater than or equal to 30. "Over-weight" refers to a condition in which a subject has a body mass index of greater or equal to 25.0. The body mass index and other definitions are according to the "NIH Clinical Guidelines on the Identification and Evaluation, and Treatment of Overweight and Obesity in Adults" (1998). In particular, obesity can lead to type II diabetes in successive phases. Clinically, these phases can be characterized as normal glucose tolerance, impaired glucose tolerance, hyperinsulinemic diabetes, and hypoinsulinemic diabetes. Such a progressive impairment of glucose storage correlates with a rise in basal glycemia.

Examples of other fat-cell related disorders include) dislipidemia, and hyperlipidemia (including high triglycerides, high LDL, high fatty acid levels).

Exemplary models for the treatment of obesity include two primary animal model systems: 1) diet-induced obesity (DIO) caused by feeding rodents ~60% fat content of caloric intake. Animals treated for up to 12-16 weeks on this type of diet gain substantial body weight (>50% increase), accumulate excessive fat mass, become hyperglycemic, hyperinsulinemic and insulin resistant. In this model compounds can be tested prior to the initiation of the diet or at any time during development of obesity. 2) db/db mutant mice (leptin receptor spontaneous mutant). These animals exhibit a similar phenotype as the DIO animals only more severe with regard to various readouts. Animals can be treated similar to the DIO model. As a surrogate readout of SirT1 inhibitor activity, sister animals can be sacrificed along the treatment regimen and assessed biochemically for increased acetylation status of FoxO1 proteins in various tissues, such as liver, muscle and white adipose tissue.

Compound described herein can be used to treat AMD. Macular degeneration includes a variety of diseases characterized by a progressive loss of central vision associated with abnormalities of Bruch's membrane and the retinal pigment epithelium. (see, e.g., US Appl 20030138798). AMD occurs in 1.2% of the population between 52 and 64 years of age and 20% of patients over the age of 75. (see, e.g., US Appl 20030087889) Macular degeneration occurs in two forms, "atrophic" ("non-exudative" or "dry" form) and "exudative" ("wet" form). A less common form of AMD is "atrophic AMD," which is due to dead RPE cells. (US Application 20030093064).

Symptoms of AMD include: straight lines in the field of vision appear wavy; type in books, magazines and newspapers appears blurry; and dark or empty spaces block the center of vision. (see, e.g., US Appl 20030065020)

Exemplary molecular markers that can be used to evaluate an AMD status include: the nucleic acid sequence of a gene encoding FBNL or the amino acid sequence of the FBNL protein: 345Arg>Trp and 362 Arg>Gln; (see, e.g., US Appl 20030138798); increases in the pigment A2E, N-retinyl-N-retinylidene ethanolamine, ultimately leading to release of cytochrome c into the cytoplasm (US Appl 20030050283); auto-antibodies against various macular degeneration-associated molecules including fibulin-3, vitronectin, β-crystallin A2, β-crystallin A3, β-crystallin A4, β-crystallin S, calreticulin, 14-3-3 protein epsilon, serotransferrin, albumin, keratin, pyruvate carboxylase, or villin 2 (see, e.g., U.S. Appl 20030017501); abnormal activity or level of complement pathway molecules including clusterin, C6 or C5b-9 complex (see, e.g., US Appl 20020015957); and accumulation of the pigment lipofuscin in lysosomes of retinal pigment epithelial (RPE) cells (Suter et al., J Biol. Chem. 275:39625-30 (2000)).

Tissue Repair

A compound described herein may also be used to modulate tissue repair or tissue state. Exemplary implementations for tissue repair include wound healing, burns, ulcers (e.g., ulcers in a diabetic, e.g., diabetic foot ulcers), surgical wounds, sores, and abrasions. The method can decrease at least one symptom of the tissue. For example, the method includes administering (e.g., locally or systemically) an effective amount of a compound described herein.

A compound may be used for a dermatological disease or disorder.

Skeletal Muscle Atrophy

Muscle atrophy includes numerous neuromuscular, metabolic, immunological and neurological disorders and diseases as well as starvation, nutritional deficiency, metabolic stress, diabetes, aging, muscular dystrophy, or myopathy. Muscle atrophy occurs during the aging process. Muscle atrophy also results from reduced use or disuse of the muscle. Symptoms include a decline in skeletal muscle tissue mass. In human males, muscle mass declines by one-third between the ages of 50 and 80.

Some molecular features of muscle atrophy include the upregulation of ubiquitin ligases, and the loss of myofibrillar proteins (Furuno et al., J. Biol. Chem., 265:8550-8557, 1990). The breakdown of these proteins can be followed, e.g., by measuring 3-methyl-histidine production, which is a specific constituent of actin, and in certain muscles of myosin (Goodman, Biochem. J, 241:121-12, 1987 and Lowell, et al., Metabolism, 35:1121-112, 1986; Stein and Schluter, Am. J. Physiol. Endocrinol. Metab. 272: E688-E696, 1997). Release of creatine kinase (a cell damage marker) (Jackson, et al., Neurology, 41: 101104, 1991) can also be indicative.

Multiple Sclerosis

Multiple sclerosis (MS) is a neuromuscular disease characterized by focal inflammatory and autoimmune degeneration of cerebral white matter. White matter becomes inflamed, and inflammation is followed by destruction of myelin (forming "lesions" which are marked by an infiltration of numerous immune cells, especially T-cell lymphocytes and macrophages. MS can cause a slowing or complete block of nerve impulse transmission and, thus, diminished or lost bodily function. A patient who has MS may have one of a variety of grade of MS (e.g., relapsing-remitting MS, primary progressive MS, secondary progressive, and Marburg's variant MS).

Symptoms can include vision problems such as blurred or double vision, red-green color distortion, or even blindness in one eye, muscle weakness in the extremities, coordination and balance problems, muscle spasticity, muscle fatigue, paresthesias, fleeting abnormal sensory feelings such as numbness, prickling, or "pins and needles" sensations, and in the worst cases, partial or complete paralysis. About half of the people suffering from MS also experience cognitive impairments, such as for example, poor concentration, attention, memory and/or judgment. (see, e.g., US 2003-0130357 and 2003-0092089)

Molecular markers of MS include a number of genetic factors, e.g., Caucasian haplotype DRB*1501-DQA1*0102-DQB1*0602 (US Appl 20030113752), a point mutation in the protein tyrosine phosphatase receptor-type C. (US Appl 20030113752), absence of wild-type SARG-1-protein, presence of mutated SARG-1-protein, or absence or mutation in the nucleic acids encoding wild-type SARG-1. (see, e.g., US Appl 20030113752) and protein indicators, e.g., Myelin Basic Protein auto-antibody in cerebrospinal fluid. (see, e.g., US Appl 20030092089)

Cellular and animal models of MS include transgenic mouse model for chronic MS (experimental autoimmune encephalomyelitis (EAE)), e.g., as described by Goverman et al., Cell. 72:551-60 (1993), and primate models as reviewed by Brok et al., Immunol. Rev., 183:173-85 (2001).

Amyotrophic Lateral Sclerosis (ALS; Lou Gehrig's Disease)

A compound described herein can be used to modulate ALS. ALS refers to a class of disorders that comprise upper and lower motor neurons. The incidence of ALS increases substantially in older adults. These disorders are characterized by major pathological abnormalities include selective and progressive degeneration of the lower motor neurons in the spinal cord and the upper motor neurons in the cerebral cortex resulting in motor neuron death, which causes the muscles under their control to weaken and waste away leading to paralysis. Examples of ALS disorders include classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) or familial ALS (a genetic version of ALS), or a combination of these conditions. (see, e.g., US Appl 20020198236 and US Appl 20030130357).

The ALS status of an individual may be evaluated by neurological examination or other means, such as MRI, FVC, MUNE etc. (see, e.g., US Appl 20030130357). Symptoms include muscle weakness in the hands, arms, legs; swallowing or breathing difficulty; twitching (fasciculation) and cramping of muscles; and reduced use of the limbs. The invention includes administering an agent that modulates the IGF-1/GH axis in an amount effective to relieve one or more ALS symptoms, e.g., in an individual having, at risk to.

Methods for evaluating ALS status of an individual can include evaluating the "excitatory amino acid transporter type 2" (EAAT2) protein or gene, the Copper-Zinc Superoxide Dismutase (SOD1) protein or gene, mitochondrial Complex I activity, levels of polyamines, such as putraceine, spermine and spermidine, ornithine decarboxylase activity, and a gene that encodes a putative GTPase regulator (see Nat. Genet., 29(2): 166-73 (2001)).

Cells and animals for evaluating the effect of a compound on ALS status include a mouse which has an altered SOD gene, e.g., a SOD1-G93A transgenic mouse which carries a variable number of copies of the human G93A SOD mutation driven by the endogenous promoter, a SOD1-G37R transgenic mouse (Wong et al., Neuron, 14(6):1105-16 (1995)); SOD1-G85R transgenic mouse (Bruijn et al., Neuron, 18(2): 327-38 (1997)); *C. elegans* strains expressing mutant human SOD1 (Oeda et al., Hum Mol. Genet., 10:2013-23 (2001)); and a *Drosophila* expressing mutations in Cu/Zn superoxide dismutase (SOD). (Phillips et al., Proc. Natl. Acad. Sci. U.S.A., 92:8574-78 (1995) and McCabe, Proc. Natl. Acad. Sci. U.S.A., 92:8533-34 (1995)).

Neuropathy

A compound described herein can be used to modulate a neuropathy. A neuropathy can include a central and/or peripheral nerve dysfunction caused by systemic disease, hereditary condition or toxic agent affecting motor, sensory, sensorimotor or autonomic nerves. (see, e.g., US App 20030013771).

Symptoms can vary depending upon the cause of the nerve damage and the particular types of nerves affected. For example, symptoms of motor neuropathy include clumsiness in performing physical tasks or as muscular weakness, exhaustion after minor exertion, difficulty in standing or walking and attenuation or absence of a neuromuscular reflex. (US App 20030013771) symptoms of autonomic neuropathy include constipation, cardiac irregularities and attenuation of the postural hypotensive reflex. (US App 20030013771), symptoms of sensory neuropathy include pain and numbness; tingling in the hands, legs or feet; and extreme sensitivity to touch, and symptoms of retinopathy include blurred vision, sudden loss of vision, black spots, and flashing lights.

Guillain-Barr syndrome is a type of motor neuropathy that usually occurs two to three weeks after a flu-like disease or other infection. Symptoms include ascending weakness wherein weakness begins in the lower extremities and ascends to the upper extremities. An elevation of the protein level in the spinal fluid without an increase in the number of white cells also results. (US Appl 20030083242)

Disorders

Additional disorders for which the compounds described herein may be useful and definitions therefore include the following:

An "age-associated disorder" or "age-related disorder" is a disease or disorder whose incidence is at least 1.5 fold higher among human individuals greater than 60 years of age relative to human individuals between the ages of 30-40, at the time of filing of this application and in a selected population of greater than 100,000 individuals. A preferred population is a United States population. A population can be restricted by gender and/or ethnicity.

A "geriatric disorder" is a disease or disorder whose incidence, at the time of filing of this application and in a selected population of greater than 100,000 individuals, is at least 70% among human individuals that are greater than 70 years of age. In one embodiment, the geriatric disorder is a disorder other than cancer or a cardio-pulmonary disorder. A preferred population is a United States population. A population can be restricted by gender and/or ethnicity.

A disorder having an "age-associated susceptibility factor" refers to a disease or disorder whose causation is mediated by an externality, but whose severity or symptoms are substantially increased in human individuals over the age of 60 relative to human individuals between the ages of 30-40, at the time of filing of this application and in the United States population. For example, pneumonia is caused by pathogens, but the severity of the disease is greater in humans over the age of 60 relative to human individuals between the ages of 30-40.

A "neoplastic disorder" is a disease or disorder characterized by cells that have the capacity for autonomous growth or replication, e.g., an abnormal state or condition characterized by proliferative cell growth. An "age-associated neoplastic disorder" is a neoplastic disorder that is also an age-associated disorder.

A "non-neoplastic disorder" is a disease or disorder that is not characterized by cells that have the capacity for autonomous growth or replication. An "age-associated non-neoplastic disorder" is a non-neoplastic disorder that is also an age-associated disorder.

A "neurological disorder" is a disease or disorder characterized by an abnormality or malfunction of neuronal cells or neuronal support cells (e.g., glia or muscle). The disease or disorder can affect the central and/or peripheral nervous system. Exemplary neurological disorders include neuropathies, skeletal muscle atrophy, and neurodegenerative diseases, e.g., a neurodegenerative disease caused at least in part by polyglutamine aggregation or a neurodegenerative disease other than one caused at least in part by polyglutamine aggregation. Exemplary neurodegenerative diseases include: Alzheimer's, Amyotrophic Lateral Sclerosis (ALS), and Parkinson's disease. An "age-associated neurological disorder is a neurological disorder that is also an age-associated disorder.

A "cardiovascular disorder" is a disease or disorder characterized by an abnormality or malfunction of the cardiovascular system, e.g., heart, lung, or blood vessels. Exemplary cardiovascular disorders include: cardiac dysrhythmias, chronic congestive heart failure, ischemic stroke, coronary artery disease, elevated blood pressure (i.e., hypertension), and cardiomyopathy. An "age-associated cardiovascular disorder" is a cardiovascular disorder that is also an age-associated disorder.

A "metabolic disorder" is a disease or disorder characterized by an abnormality or malfunction of metabolism. One category of metabolic disorders are disorders of glucose or insulin metabolism An "age-associated metabolic disorder is a metabolic disorder that is also an age-associated disorder.

A "dermatological disorder" is a disease or disorder characterized by an abnormality or malfunction of the skin. A "dermatological tissue condition" refers to the skin and any underlying tissue (e.g., support tissue) which contributes to the skins function and/or appearance, e.g., cosmetic appearance.

Exemplary diseases and disorders that are relevant to certain implementations include: cancer (e.g., breast cancer, colorectal cancer, CCL, CML, prostate cancer); skeletal muscle atrophy; adult-onset diabetes; diabetic nephropathy, neuropathy (e.g., sensory neuropathy, autonomic neuropathy, motor neuropathy, retinopathy); obesity; bone resorption; age-related macular degeneration, ALS, Alzheimer's, Bell's Palsy, atherosclerosis, cardiovascular disorders (e.g., cardiac dysrhythmias, chronic congestive heart failure, ischemic stroke, coronary artery disease, high blood pressure (i.e., hypertension), and cardiomyopathy), chronic renal failure, type 2 diabetes, ulceration, cataract, presbiopia, glomerulonephritis, Guillan-Barre syndrome, hemorrhagic stroke, short-term and long-term memory loss, rheumatoid arthritis, inflammatory bowel disease, multiple sclerosis, SLE, Crohn's disease, osteoarthritis, Parkinson's disease, pneumonia, and urinary incontinence. In addition, many neurodegenerative disorders and disorders associated with protein aggregation (e.g., other than polyglutamine aggregation) or protein misfolding can also be age-related. Symptoms and diagnosis of diseases are well known to medical practitioners. The compositions may also be administered to individuals being treated by other means for such diseases, for example, individuals being treated with a chemotherapeutic (e.g., and having neutropenia, atrophy, cachexia, nephropathy, neuropathy) or an elective surgery.

Kits

A compound described herein described herein can be provided in a kit. The kit includes (a) a compound described herein, e.g., a composition that includes a compound described herein, and, optionally (b) informational material. The informational material can be descriptive, instructional, marketing or other material that relates to the methods described herein and/or the use of a compound described herein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to methods for administering the compound.

In one embodiment, the informational material can include instructions to administer a compound described herein in a suitable manner to perform the methods described herein, e.g., in a suitable dose, dosage form, or mode of administration (e.g., a dose, dosage form, or mode of administration described herein). In another embodiment, the informational material can include instructions to administer a compound described herein to a suitable subject, e.g., a human, e.g., a human having or at risk for a disorder described herein.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, a flavoring agent (e.g., a bitter antagonist or a sweetener), a fragrance or other cosmetic ingredient, and/or a second agent for treating a condition or disorder described herein. Alternatively, the other ingredients can be included in the kit, but in different compositions or containers than a compound described herein. In such embodiments, the kit can include instructions for admixing a compound described herein and the other ingredients, or for using a compound described herein together with the other ingredients.

A compound described herein can be provided in any form, e.g., liquid, dried or lyophilized form. It is preferred that a compound described herein be substantially pure and/or sterile. When a compound described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The kit can include one or more containers for the composition containing a compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

Genetic Information

SIRT1 genetic information can be obtained, e.g., by evaluating genetic material (e.g., DNA or RNA) from a subject (e.g., as described below). Genetic information refers to any indication about nucleic acid sequence content at one or more nucleotides. Genetic information can include, for example, an indication about the presence or absence of a particular polymorphism, e.g., one or more nucleotide variations. Exemplary polymorphisms include a single nucleotide polymorphism (SNP), a restriction site or restriction fragment length, an insertion, an inversion, a deletion, a repeat (e.g., trinucleotide repeat, a retroviral repeat), and so forth.

Exemplary SIRT1 SNPs are listed in Table 2.

TABLE 2

Exemplary SIRT1 SNPs

| start | stop | dbSNP rs# | local loci | transID | avg.het | s.e.het |
|---|---|---|---|---|---|---|
| 69520160 | 69520160 | rs730821 | | | | 0 |
| 69520607 | 69520607 | rs3084650 | | | | 0 |
| 69530733 | 69530733 | rs4746715 | | | | 0 |
| 69531621 | 69531621 | rs4745944 | | | | 0 |
| 69535743 | 69535743 | rs3758391 | SIRT1: locus; | | 0.267438 | 0.153425 |
| 69536360 | 69536360 | rs3740051 | SIRT1: locus; | | 0.424806 | 0.114325 |
| 69536618 | 69536618 | rs932658 | SIRT1: locus; | | | 0 |
| 69536736 | 69536736 | rs3740053 | SIRT1: locus; | | | 0 |
| 69536742 | 69536742 | rs2394443 | SIRT1: locus; | | | 0 |
| 69539733 | 69539733 | rs932657 | SIRT1: intron; | | | 0 |
| 69540006 | 69540006 | rs737477 | SIRT1: intron; | | 0.118187 | 0.201473 |
| 69540390 | 69540390 | rs911738 | SIRT1: intron; | | | 0 |
| 69540762 | 69540762 | rs4351720 | SIRT1: intron; | | | 0 |
| 69540970 | 69540970 | rs2236318 | SIRT1: intron; | | 0.222189 | 0.135429 |
| 69541621 | 69541621 | rs2236319 | SIRT1: intron; | | 0.455538 | 0.102018 |
| 69544136 | 69544136 | rs768471 | SIRT1: intron; | | 0 | 0.01 |
| 69547213 | 69547213 | rs1885472 | SIRT1: intron; | | | 0 |
| 69549191 | 69549191 | rs2894057 | SIRT1: intron; | | | 0 |
| 69551326 | 69551326 | rs4746717 | SIRT1: intron; | | | 0 |
| 69557788 | 69557788 | rs2224573 | SIRT1: intron; | | | 0 |
| 69558999 | 69558999 | rs2273773 | SIRT1; | NM_012238; | 0.430062 | 0.135492 |
| 69559302 | 69559302 | rs3818292 | SIRT1: intron; | | 0.456782 | 0.10598 |
| 69564725 | 69564725 | rs1063111 | SIRT1; | NM_012238; | | 0 |
| 69564728 | 69564728 | rs1063112 | SIRT1; | NM_012238; | | 0 |
| 69564741 | 69564741 | rs1063113 | SIRT1; | NM_012238; | | 0 |
| 69564744 | 69564744 | rs1063114 | SIRT1; | NM_012238; | | 0 |
| 69565400 | 69565400 | rs3818291 | SIRT1: intron; | | 0.179039 | 0.132983 |
| 69566230 | 69566237 | rs5785840 | SIRT1: intron; | | | 0 |
| 69566318 | 69566318 | rs2394444 | SIRT1: intron; | | | 0 |
| 69567559 | 69567559 | rs1467568 | SIRT1: intron; | | | 0 |
| 69567728 | 69567728 | rs1966188 | SIRT1: intron; | | | 0 |
| 69568961 | 69568961 | rs2394445 | SIRT1; | NM_012238: UTR; | | 0 |
| 69568962 | 69568962 | rs2394446 | SIRT1; | NM_012238: UTR; | | 0 |
| 69569231 | 69569231 | rs4746720 | SIRT1; | NM_012238: UTR; | | 0 |

TABLE 2-continued

Exemplary SIRT1 SNPs

| start | stop | dbSNP rs# | local loci | transID | avg.het | s.e.het |
|---|---|---|---|---|---|---|
| 69569461 | 69569461 | rs752578 | SIRT1; | NM_012238: UTR; | | 0 |
| 69570479 | 69570479 | rs2234975 | SIRT1; | NM_012238: UTR; | | 0 |
| 69570580 | 69570580 | rs1022764 | SIRT1: locus; | | | 0 |
| 69570983 | 69570983 | rs1570290 | SIRT1: locus; | | 0.0392 | 0.167405 |
| 69572334 | 69572334 | rs2025162 | | | | 0 |
| 69573968 | 69573968 | rs4141919 | DKFZP564G092: locus; | | | 0 |
| 69574252 | 69574252 | rs14819 | DKFZP564G092: locus; | | | 0 |
| 69575032 | 69575032 | rs14840 | DKFZP564G092: locus; | | | |

It is possible to digitally record or communicate genetic information in a variety of ways. Typical representations include one or more bits, or a text string. For example, a biallelic marker can be described using two bits. In one embodiment, the first bit indicates whether the first allele (e.g., the minor allele) is present, and the second bit indicates whether the other allele (e.g., the major allele) is present. For markers that are multi-allelic, e.g., where greater than two alleles are possible, additional bits can be used as well as other forms of encoding (e.g., binary, hexadecimal text, e.g., ASCII or Unicode, and so forth). In some embodiments, the genetic information describes a haplotype, e.g., a plurality of polymorphisms on the same chromosome. However, in many embodiments, the genetic information is unphased.

A decision about whether to administer a compound described herein can be made depending on the genetic information about SIRT1. For example, a method for administering a compound described herein can include evaluating nucleic acid from a subject to obtain genetic information about SIRT1 or another sirtuin, and administering a compound described herein.

Databases

The invention also features a database that associates information about or identifying one or more of the compounds described herein with a parameter about a patient, e.g., a patient being treated with a disorder herein. The parameter can be a general parameter, e.g., blood pressure, core body temperature, etc., or a parameter related to a specific disease or disorder, e.g., as described herein.

EXAMPLES

In all of the Examples below, compounds are referred to as they correspond to their designation in Table 1 (i.e., exemplified compounds).

Example 1

HeLa Apoptosis Assay

The following exemplary compounds were evaluated for their effect on a HeLa cell apoptosis assay using the Cell Death Detection ELISA plus kit from Roche Applied Science.

| Compound | dose | average | SD |
|---|---|---|---|
| 8 | 0 | 1.12 | 0.15 |
| 8 | 0.5 | 1.23 | 0.04 |
| 8 | 2.5 | 1.85 | 0.24 |
| 8 | 10 | 2.11 | 0.25 |
| 8 | 25 | 2.27 | 0.20 |
| 5 | 0 | 0.92 | 0.07 |
| 5 | 0.5 | 1.00 | 0.08 |
| 5 | 2.5 | 0.97 | 0.11 |
| 5 | 10 | 1.07 | 0.02 |
| 5 | 25 | 0.91 | 0.07 |
| Resveratol | 0 | 0.73 | 0.08 |
| Resveratol | 0.5 | 0.83 | 0.05 |
| Resveratol | 2.5 | 0.84 | 0.02 |
| Resveratol | 10 | 1.01 | 0.07 |
| Resveratol | 25 | 0.56 | 0.08 |
| DMSO | 0 | 0.72 | 0.09 |
| DMSO | 0.5 | 0.79 | 0.12 |
| DMSO | 2.5 | 0.91 | 0.13 |
| DMSO | 10 | 0.76 | 0.09 |
| DMSO | 25 | 1.18 | 0.20 |

Example 2

List of Reagents:

| | Name of Reagent | Supplied As | Source | Catalog Number | Storage |
|---|---|---|---|---|---|
| 1 | human SirT1 | 2.5 or 3.5 U/ul | Biomol | SE-239 | −20 C. |
| 2 | Fluor de Lys Substrate | 50 mM in DMSO | Biomol | KI-104 | −20 C. |
| 3 | Fluor de Lys Developer | 20x concentrate | Biomol | KI-105 | −20 C. |
| 4 | NAD | solid | Sigma | N-1636 | −20 C. |
| 5 | Nicotinamide | solid | Calbiochem | 481907 | RT |
| 6 | Trizma-HCl | solid | Sigma | T-5941 | RT |
| 7 | Sodium Chloride | solid | Sigma | S-9888 | RT |
| 8 | Magnesium Chloride | solid | Sigma | M-2393 | RT |
| 9 | Potassium Chloride | solid | Sigma | P-3911 | RT |
| 10 | Polyoxyethylene sorbitan monolaurate (Tween-20) | 100% | Sigma | P-7949 | RT |
| 11 | Fluor de Lys Deacetylated Standard | 10 mM in DMSO | Biomol | KI-142 | −20 C. |

List of Equipment:

|   | Tool Name | Tool Source | Catalog Number |
|---|---|---|---|
| 1 | Fluorescence Plate Reader Synergy HT | BIO-TEK | SIAFR |
| 2 | Matrix Impact2 16 Channel pipet | Apogent Discoveries | 2069 |
| 3 | 37C Incubator | VWR | 1540 |

List of Disposables:

|   | Disposable | Source | Catalog Number |
|---|---|---|---|
| 1 | 384 white low volume plates | Greiner/Bellco | 4507-84075 |
| 2 | Tips for matrix 16 chan pipet | Apogent Discoveries | 7421 |
| 3 | 25 ml divided reagent reservoirs | Apogent Discoveries | 8095 |
| 4 | Plate Sealing Films | Apogent Discoveries | 4418 |

Standard Reagent Formulations:

|   | Prepared Reagent Name | Component Name | M.W. | Component Quantity (in water) | Final Component Concentration | Storage |
|---|---|---|---|---|---|---|
| 1 | Tris-HCl, pH 8.0 | Trizma-HCl HCl | 157.6 | 157.6 g/L to pH 8.0 | 1M pH 8.0 | RT |
| 2 | Sodium Chloride | NaCl | 58.44 | 292 g/L | 5M | RT |
| 3 | Magnesium Chloride | $MgCl_2$ | 203.3 | 20.33 g/L | 100 mM | RT |
| 4 | Potassium Chloride | KCl | 74.55 | 20.13 g/L | 270 mM | RT |
| 5 | Polyoxyethylene sorbitan monolaurate | Tween-20 |  | 1 ml/10 ml | 10% | RT |
| 6 | NAD | NAD | 717 | 0.0717 g/ml | 100 mM | −20 C. |
| 7 | Nicotinamide | Nicotinamide | 122 | 0.0061 g/ml | 50 mM | −20 C. |
| 8 | Assay Buffer | Tris-HCl, pH 8.0 |  | 25 ml of 1M stock/L | 25 mM | 4 C. |
|   |   | NaCl |  | 27.4 ml of 5M stock/L | 137 mM |   |
|   |   | KCl |  | 10 ml of 270 mM stock/L | 2.7 mM |   |
|   |   | $MgCl_2$ |  | 10 ml of 100 mM stock/L | 1 mM |   |
|   |   | Tween-20 |  | 5 ml of 10% stock/L | 0.05% |   |
| **Prepare working stocks below just before use |   |   |   | The following are prepared in assay buffer |   |   |
| 9 | 2x Substrates | Flour de Lys substrate |  | 6 ul/ml | 300 uM | ice |
|   |   | NAD |  | 20 ul of 100 mM stock/ml | 2 mM |   |
| 10 | Enzyme Mix | Biomol SirT1 |  | **depends upon specific activity of lot. Ex: 3.5 U/ul, 35.71 ul/ml | 0.125 U/ul (0.5 U/well) | ice |
| 11 | Developer/stop reagent | 20x developer concentrate nicotinamide |  | 50 ul/ml | 1× in assay buffer | ice |
|   |   |   |   | 20 ul of 50 mM stock/ml | 1 mM |   |

Example 3

In order to determine if the mammalian enzyme is inhibited by compound 8, 293T cells were transfected with a construct designed to express human SIRT1 fused to glutathione-S-transferase to allow for rapid purification from cell extracts. Following lysis cell extracts were incubated with glutathione-Sepharose beads followed by several washes in lysis buffer and a final wash in SIRT1 enzyme assay buffer. Beads with bound GST-SIRT1 were added to the Fleur-de-lys assay (Biomol) in the presence of a range of concentrations of compound 8. As can be seen in FIG. 2a, the $EC_{50}$ value of compound 8 for mammalian SIRT1 is comparable to that obtained for the recombinant bacterially produced human enzyme.

As can be seen in FIG. 2B, compound 8 enters cells and increases p53 acetylation (at lysine 382) after etoposide treatment. In the experiment depicted in FIG. 2B, NCI-H460 cells were treated with 20 uM etoposide (a DNA damaging agent) in the presence or absence of SIRT1 inhibitors, either compound 8 or nicotinamde and the amount of acetylated p53 (at lysine 382) was visualized by Western blot. Compound 8 is able to increase p53 acetylation significantly relative to DMSO alone and 1 uM and 10 uM is equally effective.

Example 4

Figure 3A:
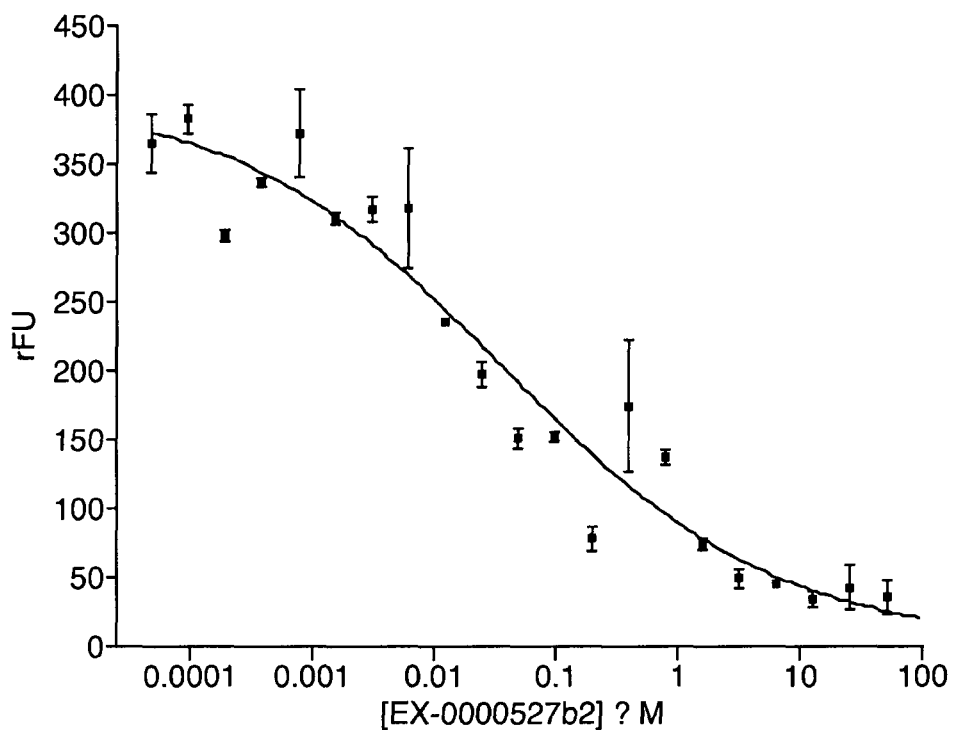
FIG. 3a is a graph depicting the inhibition of mammalia SirT1 by compound 8.
Figure 3B:
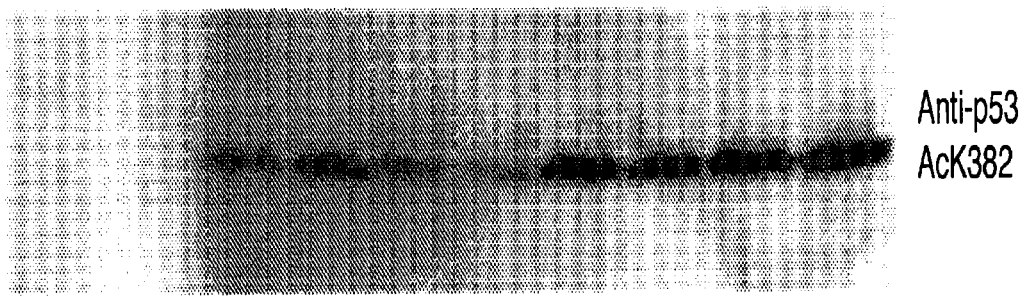
FIG. 3b is a Western blot of NCI-H460 cells treated with etoposide only or etoposide and compound 8.

Enantiomers of compound 8 were tested, where each enantiomer had a purity of greater than 90% enantiomeric excess, to determine if a single enantiomer was more potent than a mixture of enantiomers. NCI-H460 cells were treated for 6 hours with compounds 8(+) and 8(−) in the presence of 20 micromolar etoposide followed by lysis and immunoprecipitaion of p53 using Ab-6 (Oncogene Science). Extracts were probed with an antibody that recognizes acetylated lysine 382 of p53 (Cell Signaling). FIG. 3 demonstrates that there are active and inactive enantiomers of compound 8. Specifically the inactive enantiomer, compound 8(+), does not lead to increased acetylation of p53 in the presence of etoposide whereas compound 8(−) leads to a significant increase in acetylation and stabilization of p53 protein.

Example 5

Figure 4:
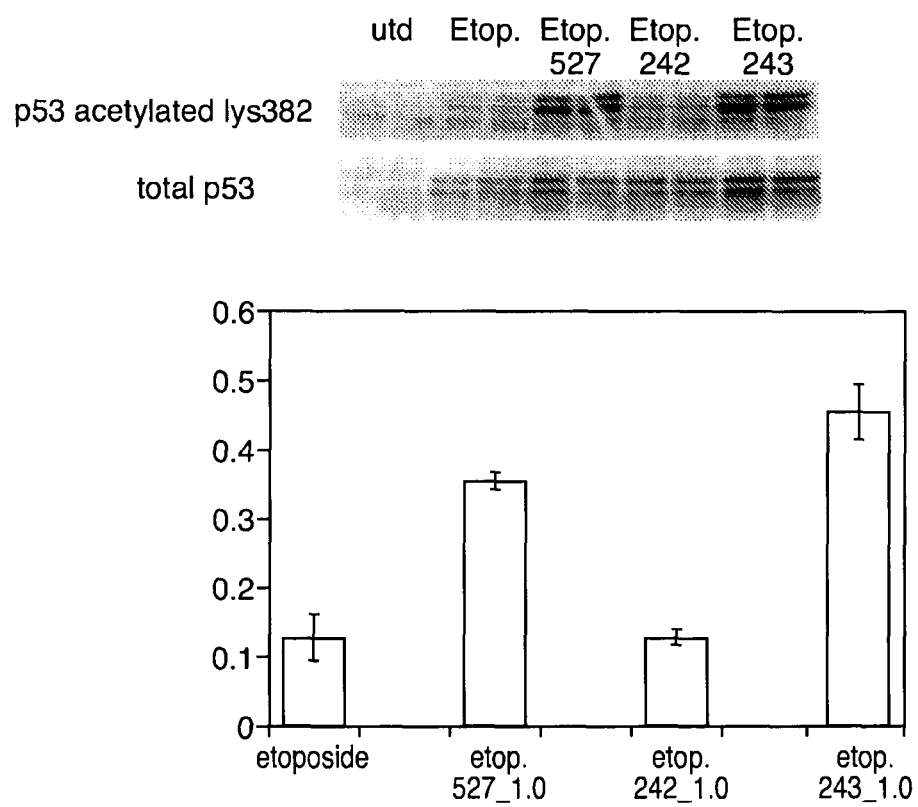
FIG. 4 is a bar graph depicting that enantiomer 8(−) of compound 8 leads to an increase in p53 acetylation.

In the results of the experiment below, which is depicted in FIG. 4, we show that a compound's ability to increase p53 acetylation correlates with its in vitro potency against SIRT1. A series of structurally similar compounds were added to cells at 1 uM concentration. Only those compounds that inhibit SIRT1 with IC50s below 1 uM increased p53 acetylation, whereas compounds with IC50s above 1 uM did not.

Example 6

Figure 5:
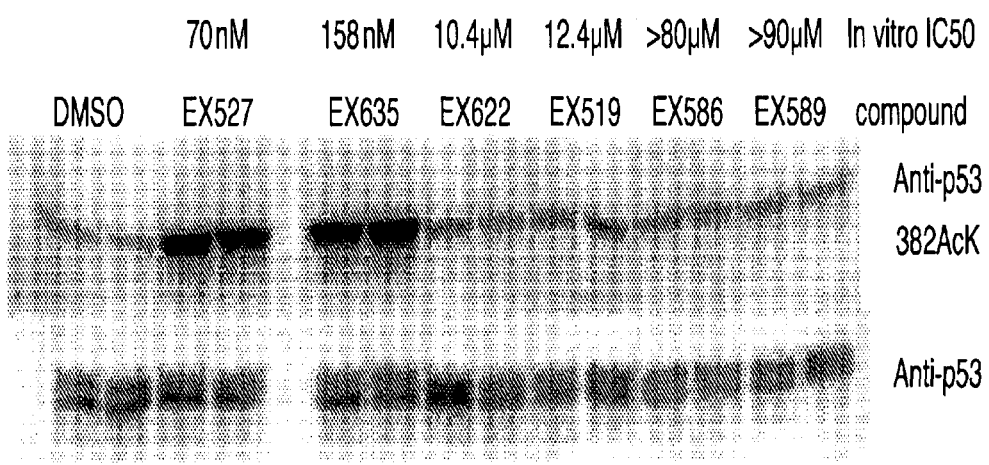
FIG. 5 is a Western blot depicting that compounds which inhibit SirT catalytic activity also effect p53 acetylation.

The experiment depicted in FIG. 5 demonstrates that in a yeast silencing assay dependent on SIRT1 activity, the inactive enantiomer of compound 8, compound 8(+), has no effect on cell growth whereas the active enantiomer, 8(−), inhibits SIRT1 and allows for expression of URA3 which blocks growth in the presence of 5-fluorouracil. Strain SL8c (URA at the telomere) was used for yeast based assay to screen compounds. Cells were grown in -URA media to select de-silenced cells. The next day cells were diluted 1:20 into fresh YPD with 2% glucose then grow for 5 hrs. Cells were then diluted OD=0.01 in both SD and SD+0.1% 5FOA media. The compounds were then serially diluted into 10 ul of SD or SD+0.1% 5FOA medium. 140 ul of cells were pipetted into a 96 well plate and grown at 30° C. for 18-24 hrs.

Example 7

Figure 6:
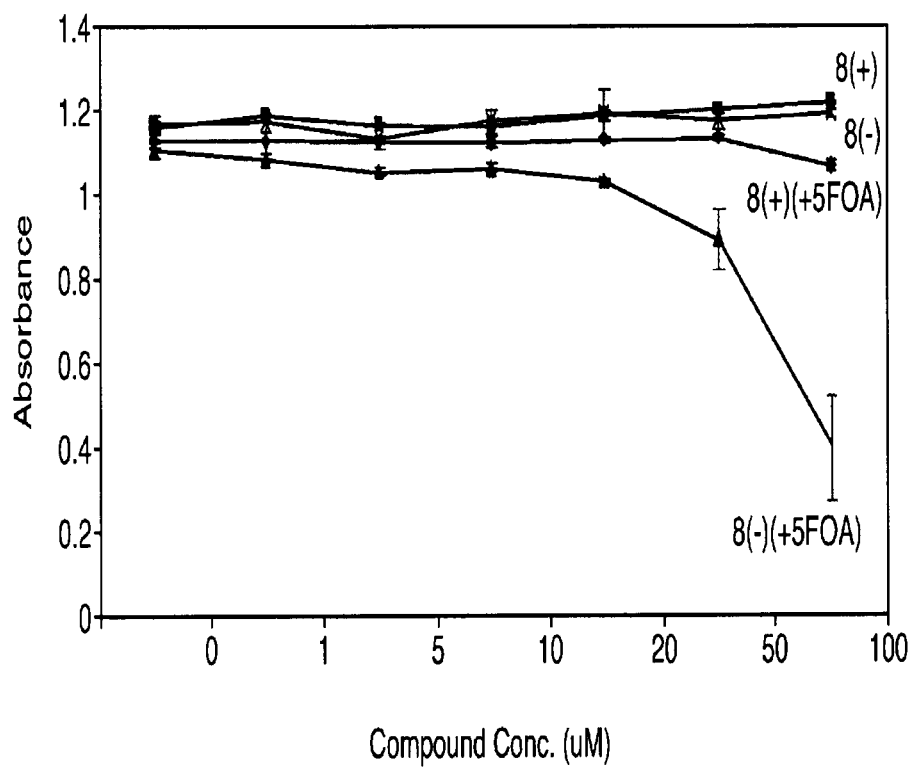
FIG. 6 is a graph depicting that enantiomer 8(−) of compound 8 preferentially inhibits yeast sir2 relative to enantiomer 8(+).

Compound 8 inhibits the SIRT1 enzyme in additional cells. Cell lines U20S and MCF7 cell lines were treated with compound 8 in the presence of 20 micromolar etoposide (TOPO) for 6 hours followed by lysis and immunoprecipitation with p53 Ab-6 conjugated to agarose beads. Samples were analyzed by SDS-PAGE and immunoblotted with an antibody that recognizes acetylated lysine 382 of p53. The results depicted in FIG. 6 demonstrate that compound 8 is competent to inhibit SIRT1 in a variety of cell lines with similar effects on P53 acetylation.

Example 8

Figure 7:
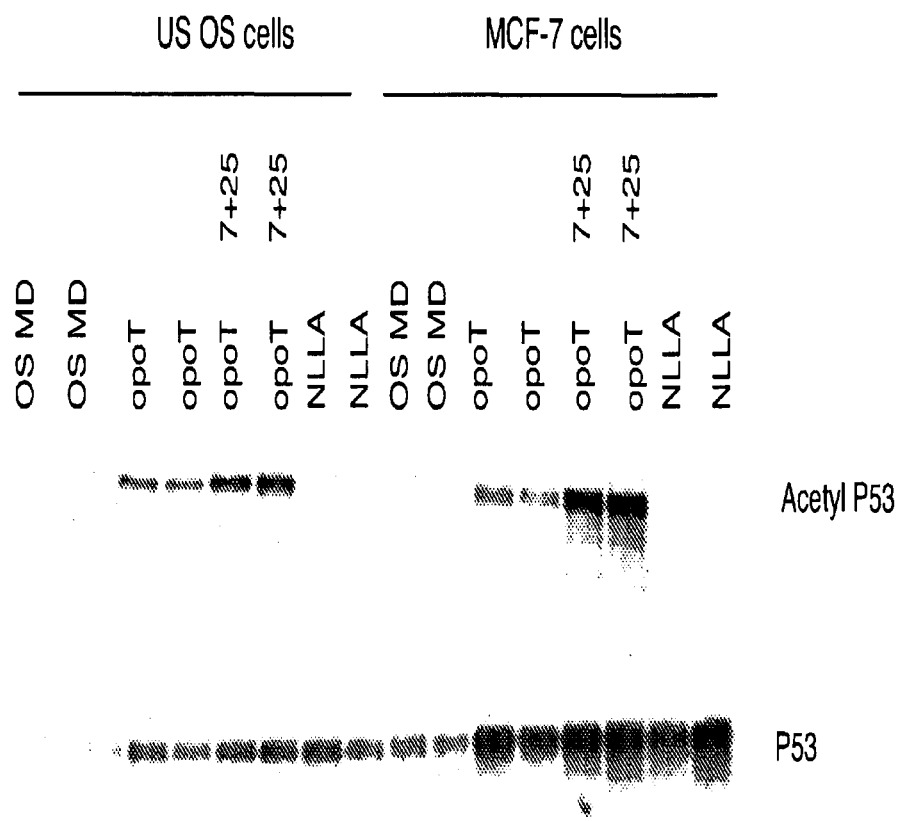
FIG. 7 is a gel assay depicting the effectiveness of compound 8 for inhibiting SirT1 in U2 OS cells and MCF-7 cells.
Figure 8:
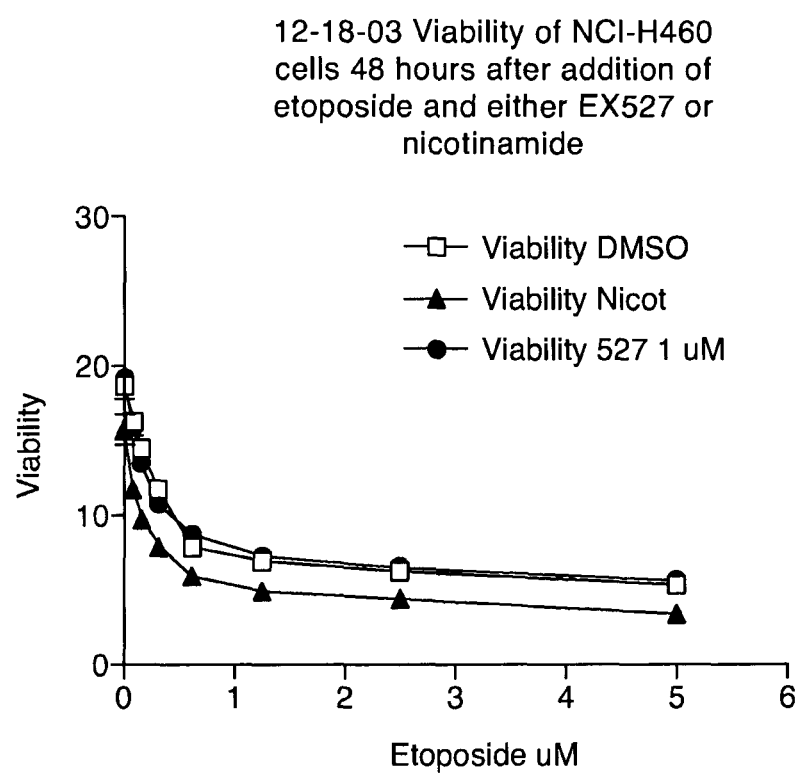
FIG. 8 is a graph depicting the effect of compound 8 on cell survival after DNA damage.

In order to assess whether the affects of compound 8 on p53 acetylation lead to changes in p53 function on experiment was performed to measure cell survival after DNA damage. NCI-H460 cells were damaged with varying concentrations of etoposide in the presence or absence of SIRT1 inhibitors. As depicted in FIG. 7, compound 8 by itself did not modulate p53 function significantly in this assay.

Example 9

Figure 9A:
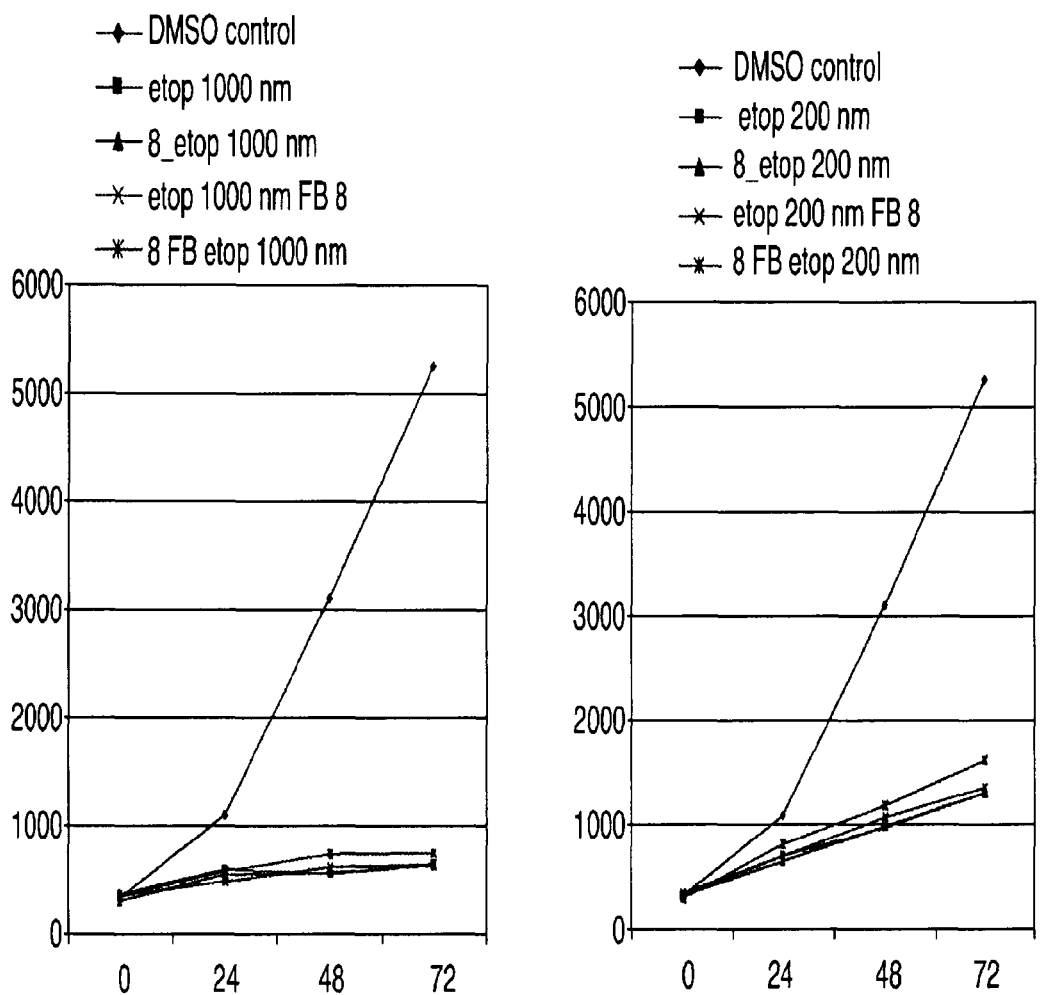
FIG. 9 are graphs depicting the effect of compound 8 on cell survival of NCI-H460 cells.
Figure 9B:
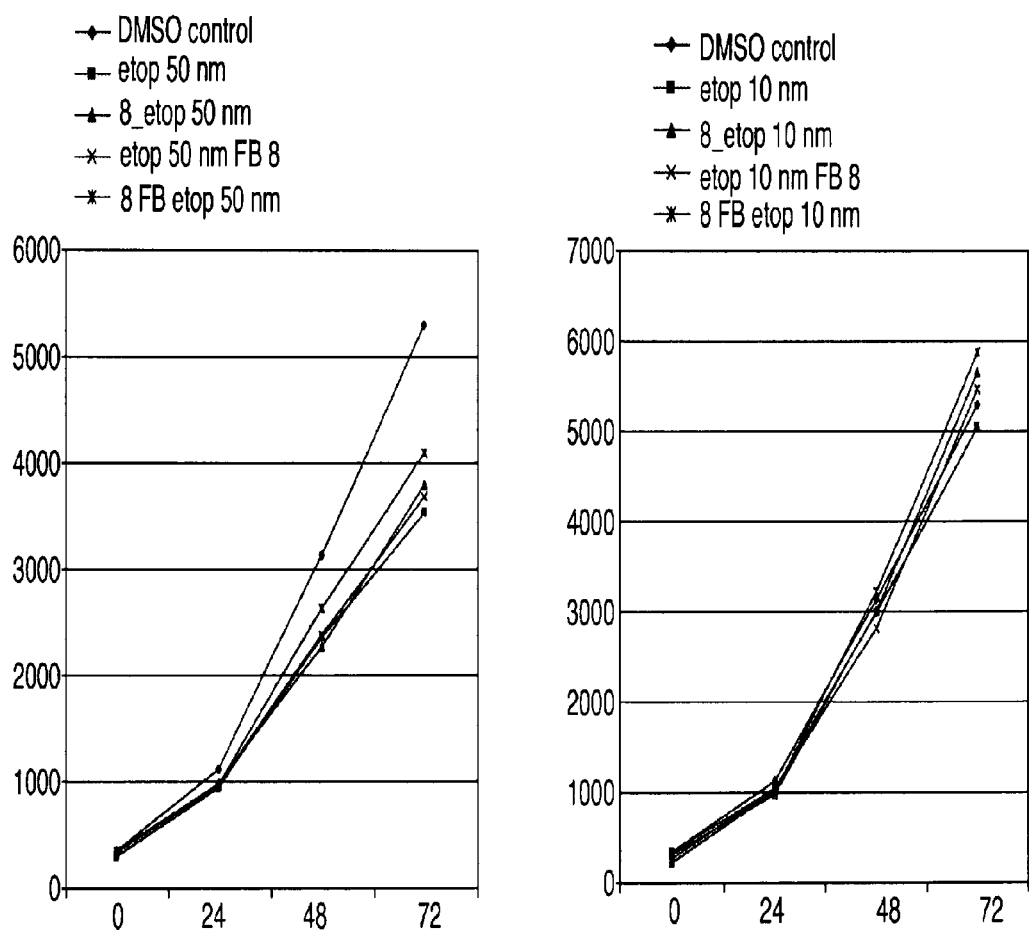
Figure 9C:
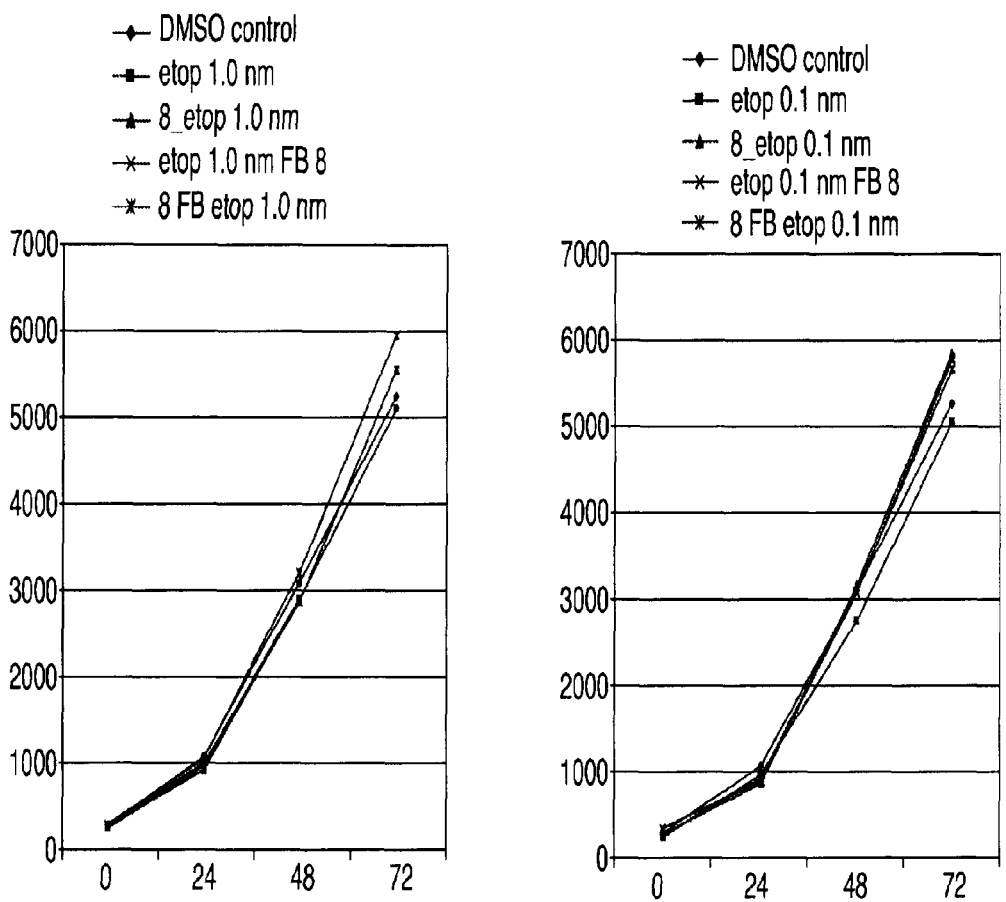
Figure 10:
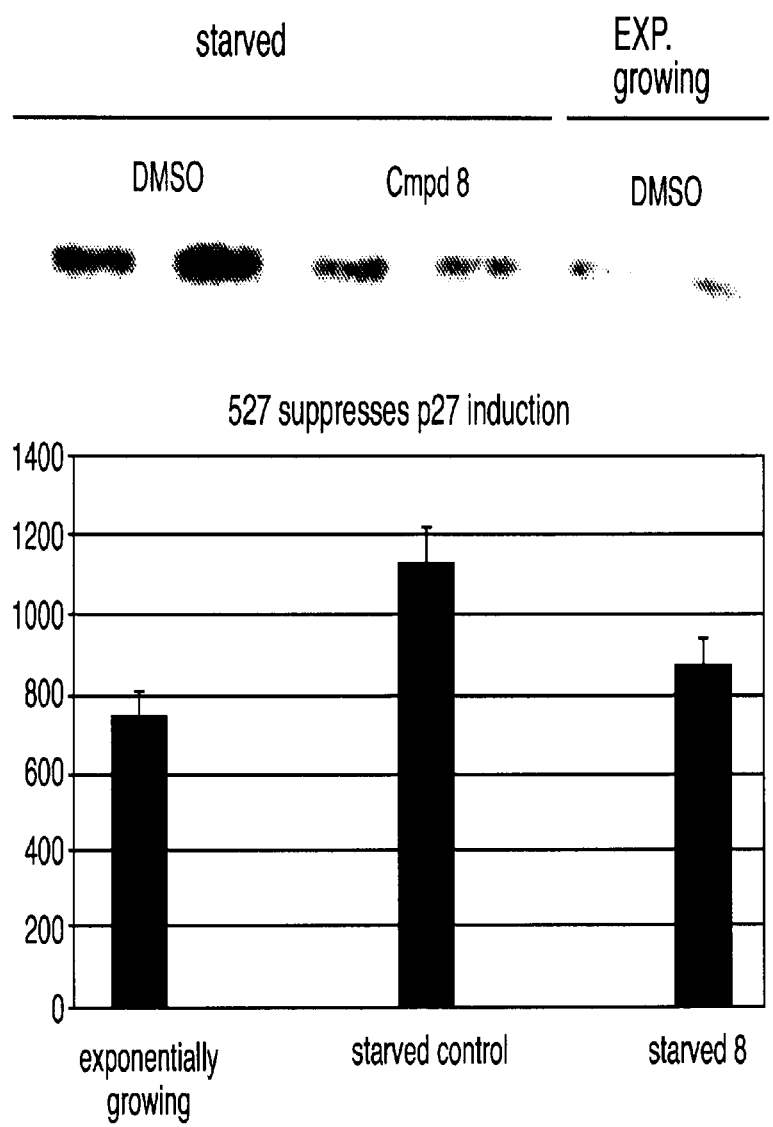
FIG. 10 is a bar graph depicting that compound 8 leads to abrogation of serum starvation-mediated upregulation of the cell cycle inhibitor p27.
Figure 11:
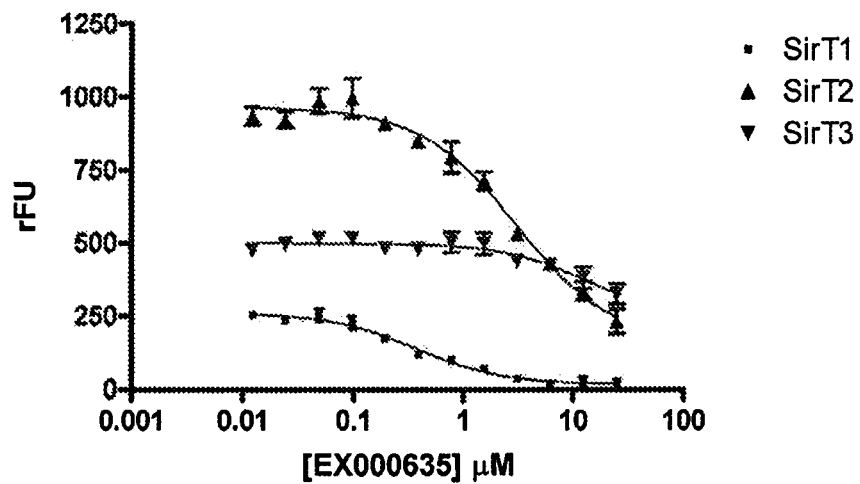
FIG. 11 is a graph depicting the inhibition of SirT enzymes by EX000635.
Figure 12:
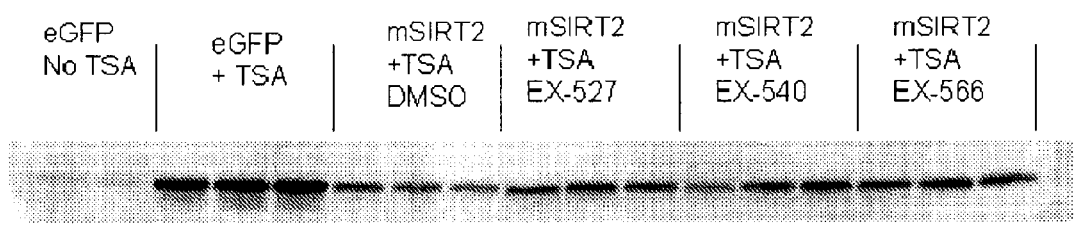
FIG. 12 is a gel assay depicting the effect of various compounds on SIRT2 in the presence of TSA.

Cells were plated at a density of 800 per well in 96 well cytostar plates in the presence of a range of etoposide concentrations and 1 micromolar compound 8. Thymidine incorporation was measured at 24 hours intervals. As depicted in FIG. 9, this experiment demonstrates that there is no synergy between etoposide and compound 8 on the growth characteristics of NCI-H460 cells under conditions in which compound was added concurrent to, prior to, and after treatment with etoposide.

Example 10

HEK293 cells were serum starved in the presence or absence of compound 8 for 24 hrs followed by lysis and immunoblotting analysis of p27 protein. As can be seen in FIG. 9, treatment of cells with compound 8 leads to abrogation of serum starvation-mediated upregulation of the cell cycle inhibitor p27. The proposed explanation for this result is that SIRT1-mediated deacetylation leads to inactivation of FOXO1-mediated transcription of p27 and the addition of compound 8 reverses this effect.

Example 11

HeLa cells were transfected with GFP-hSIRT2 isoform 1 (green). At 36 hours post transfection 1 μM of TSA and either DMSO or 50 μM of compound 8 was added. The next morning cells were fixed, permeabilized, and stained for acetylated tubulin (red). In cells treated with DMSO there was very little acetylated tubulin in cells expressing SIRT2, in cells treated with compound 8 the tubulin is more highly acetylated indicating that the effect of SIRT2 was blocked.

It was also possible to observe the effect of the compounds using Western analysis. 293T cells were transfected with either eGFP (control) or with mouse SIRT2 Isoform 1 (mSIRT2). TSA was added to increase amount of acetylated tubulin and at the same time either DMSO or the compound listed below were added to 10 μM.

Procedure Description:

Step Description

1. Prepare amount of 2× Substrates necessary for the number of wells to be assayed. 5 ul per well is needed
2. Dispense 5 ul 2× substrates to test wells
3. Dispense 1 ul of test compound to the test wells
   Dispense 1 ul of compound solvent/diluent to the positive control wells
   Dispense 1 ul of 1 mM nicotinamide to the 50% inhibition wells
   Dispense 1 ul of 10 mM nicotinamide to the 100% inhibition wells
4. Dispense 4 ul of assay buffer to negative control wells (no enzyme controls)
5. Prepare amount of enzyme necessary for number of wells to assay. 4 ul enzyme mix needed per well
6. Dispense 4 ul of enzyme mix to the test wells and positive control wells
7. Cover and incubate at 37° C. for 45 minutes
8. Less then 30 minutes before use, prepare amount of 1× developer/stop reagent for the number of wells being assayed
9. Dispense 10 ul 1× developer/stop reagent to all wells
10. Incubate at room temperature for at least 15 minutes
11. Read in fluorescence plate reader, excitation=350-380 nm, emission=440-460
12. Fluor de Lys in the substrate has an intrinsic fluorescence that needs to be subtracted as background before any calculations are to be done on the data. These values can be found in the negative control wells.
    Appendix 1: Preparation of a Standard Curve Using Fluor De Lys Deacetylated Standard
1. Determine the concentration range of deacetylated standard to use in conjunction with the above assay by making a 1 uM dilution of the standard. Mix 10 ul of the 1 uM dilution with 10 ul developer and read at the same wavelengths and sensitivity settings that the assay is read at.

Use this estimate of AFU (arbitrary fluorescence units)/uM to determine the range of concentrations to test in the standard curve.

2. Prepare, in assay buffer, a series of dilutions of the Fluor de Lys deactylated standard that span the desired concentration range
3. Pipet 10 ul assay buffer to the 'zero' wells
4. Pipet 10 ul of the standard dilutions into wells
5. Pipet 10 ul developer to the wells and incubate 15 minutes at RT
6. Read plate at above wavelengths
7. Plot fluorescence signal (y) versus concentration of the Fluor de Lys deacetylated standard (x) and determine the slope as AFU/uM Protocol for Testing for Inhibitors of the Developer Reaction 1. From the standard curve select concentration of deacetylated standard that gives a fluorescence signal equivalent to positive controls in assay (eg. 5 uM)
2. Dispense 5 ul 2× deacetylated standard (eg. 10 uM)
3. Dispense 1 ul compound, 4 ul assay buffer
4. Dispense 10 ul developer
5. Incubate at room temp 15 minutes (or equivalent time as in screen) and read at same settings as screen Example 12

Synthesis of 2-chloro-5,6,7,8,9,10-hexahydrocyclohepta[b]indole-6-carboxamide

Preparation of methyl 3-bromo-2-oxocycloheptanecarboxylate: Methyl 2-oxo-1-cycloheptanecarboxylate (50 g, 294 mmole) was dissolved in carbon tetrachloride (200 mL) and chilled to 0° C. Bromine (46.8 g, 294 mmole) was added via addition funnel over ~30 minutes. The cooling bath was then removed and the reaction was allowed to warm to rt. The reaction was stirred under nitrogen at room temperature for 4 days. After 4 days the solution was poured into a separatory funnel containing water (1 L). The organic was washed with water and dried over sodium sulfate. Removal of the solvent in vacuo gave (72.4 g, 291 mmole, 99% crude yield). The material was carried on without further purification.

Preparation of methyl 2-chloro-5,6,7,8,9,10-hexahydrocyclohepta[b]indole-6-carboxylate: Methyl 3-bromo-2-oxocycloheptanecarboxylate (16.8 g, 67.4 mmol) and 4-chloroaniline (18.4 g, 98%, 2.13 eq, 143.6 mmol) were added to flask with thermometer, nitrogen inlet and mechanical stirring machine. As the temperature of the mixture passed 140° C. a relatively rapid exotherm and vigorous evolution of gas occurred. The reaction was cooled with water immediately. The reaction mixture was dissolved in DCM (200 mL). The material was transferred into a separatory funnel and washed with water (2×50 mL), 3HCl (3×50 mL), water (2×50 mL), brine, dried over $Na_2SO_4$, and the solvent was removed by vacuo. The crude residue was applied to a Biotage and eluted with 9/1 heptane/ethyl acetate to afford product 10 g (53%) as an off white solid, which was used for next reaction without further purification.

Preparation of 2-chloro-5,6,7,8,9,10-hexahydrocyclohepta[b]indole-6-carboxamide: Methyl 2-chloro-5,6,7,8,9,10-hexahydrocyclohepta[b]indole-6-carboxylate (10 g, 36 mmol) was dissolved in 7 N ammonia in methanol (350 mL) and transferred to Parr pressure reactor. The reaction vessel was purged briefly to displace any air with Nitrogen. The reaction was then heated to 90° C. for 48 h. The reaction was cooled to r.t. and the solvent removed in vacuo, the crude residue was applied to a Biotage and eluted with grading (1/1 heptane/ethyl acetate to 0/1 heptane/ethyl acetate) to afford product as an off white foam, which was triturated with DCM to afford pure product 2 g (21%) as an off white solid.

A number of embodiments of the invention have been described. Nevertheless, it will be understood that various modifications may be made without departing from the spirit and scope of the invention. Other embodiments are in the claims.

What is claimed is:

1. A method of relieving, altering, ameliorating, improving or affecting Huntington's disease, the method comprising administering a compound of formula (XI):

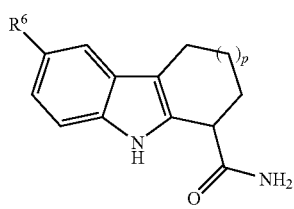

formula (XI)

wherein $R^6$ is halo, $C_1$-$C_6$ alkyl, $C_1$-$C_6$ haloalkyl, or $C_1$-$C_6$ haloalkoxy; and p is 0, 1, or 2.

2. The method of claim 1, wherein $R^6$ is halo or $C_1$-$C_6$ alkyl.

3. The method of claim 1, wherein $R^6$ is chloro or methyl.

4. The method of claim 1, wherein the compound is 6-Chloro-2,3,4,9-tetrahydro-1H-carbazole-1-carboxylic acid amide.

5. The method of claim 1, wherein the compound is present in a composition comprising a racemic mixture of a compound of formula (XI).

* * * * *